US008283517B2

(12) United States Patent
Schilling et al.

(10) Patent No.: US 8,283,517 B2
(45) Date of Patent: Oct. 9, 2012

(54) TRANSGENIC MOUSE MODELS OF Aβ OVEREXPRESSION

(75) Inventors: Stephan Schilling, Halle/Saale (DE);
Holger Cynis, Halle/Saale (DE);
Hans-Ulrich Demuth, Halle/Saale (DE);
Wolfgang Jagla, Windach (DE); Sigrid Graubner, Munich (DE)

(73) Assignee: Probiodrug AG, Halle (Saale) (DE)

( * ) Notice: Subject to any disclaimer, the term of this patent is extended or adjusted under 35 U.S.C. 154(b) by 91 days.

(21) Appl. No.: 12/209,321

(22) Filed: Sep. 12, 2008

(65) Prior Publication Data

US 2009/0098052 A1    Apr. 16, 2009

Related U.S. Application Data

(60) Provisional application No. 60/971,631, filed on Sep. 12, 2007.

(51) Int. Cl.
*G01K 33/00* (2006.01)
*A01K 67/033* (2006.01)
*A01K 67/027* (2006.01)
*C12N 5/00* (2006.01)

(52) U.S. Cl. .................. 800/18; 800/3; 800/8; 435/325

(58) Field of Classification Search .................. 800/3, 8, 800/18; 435/325
See application file for complete search history.

(56) References Cited

U.S. PATENT DOCUMENTS

| | | | |
|---|---|---|---|
| 4,873,191 A | 10/1989 | Wagner et al. | |
| 4,873,316 A | 10/1989 | Meade et al. | |
| 5,175,384 A | 12/1992 | Krimpenfort et al. | |
| 5,602,299 A | 2/1997 | Lazzarini | |
| 5,849,999 A * | 12/1998 | Neve et al. ........................ | 800/3 |
| 5,981,830 A | 11/1999 | Wu et al. | |
| 6,037,521 A * | 3/2000 | Sato et al. ........................ | 800/18 |
| 6,066,778 A | 5/2000 | Ginsburg et al. | |
| 6,673,600 B2 * | 1/2004 | Peraus et al. ............... | 435/320.1 |
| 6,900,367 B2 * | 5/2005 | Cohen et al. .................... | 800/13 |
| 7,304,086 B2 | 12/2007 | Schilling | |
| 7,371,871 B2 | 5/2008 | Schilling | |
| 7,381,537 B2 | 6/2008 | Demuth | |
| 7,462,599 B2 | 12/2008 | Schilling | |
| 2005/0137142 A1 | 6/2005 | Schulz | |
| 2005/0171112 A1 | 8/2005 | Schulz | |
| 2006/0100253 A1 | 5/2006 | Niestroj | |
| 2007/0191366 A1 | 8/2007 | Hoffmann | |
| 2008/0153892 A1 | 6/2008 | Schilling | |
| 2008/0200567 A1 | 8/2008 | Schilling et al. | |
| 2008/0207715 A1 | 8/2008 | Thormann | |
| 2008/0214620 A1 | 9/2008 | Heiser | |
| 2008/0221086 A1 | 9/2008 | Thormann | |
| 2008/0234313 A1 | 9/2008 | Ramsbeck | |
| 2008/0249083 A1 | 10/2008 | Schilling et al. | |
| 2008/0260688 A1 | 10/2008 | Buhholz | |
| 2008/0262063 A1 | 10/2008 | Buchholz | |
| 2008/0262065 A1 | 10/2008 | Buchholz | |
| 2008/0267911 A1 | 10/2008 | Buchholz | |
| 2008/0267912 A1 | 10/2008 | Buchholz | |
| 2008/0286231 A1 | 11/2008 | Buchholz | |
| 2008/0286810 A1 | 11/2008 | Demuth | |
| 2008/0292582 A1 | 11/2008 | Buchholz | |
| 2009/0018087 A1 | 1/2009 | Schilling | |
| 2009/0068699 A1 | 3/2009 | Schilling | |
| 2009/0149394 A1 | 6/2009 | Schilling | |

FOREIGN PATENT DOCUMENTS

| | | |
|---|---|---|
| EP | 0264166 | 4/1986 |
| WO | WO 90/08832 | 8/1990 |
| WO | WO 96/13513 | 5/1996 |
| WO | WO 2004/098625 | 11/2004 |
| WO | WO 2005/049027 | 6/2005 |

OTHER PUBLICATIONS

Wall (1996, Theriogenology, vol. 45, p. 57-68).*
Ebert (1988, Mol. Endocrinology, vol. 2, pp. 277-283).*
Reaume (J. Biol. Chem., Sep. 20, 1996, vol. 271, No. 38, p. 23380-23388).*
Alignment for Neve, 2011.*
Alignament for Sato, 2011.*
Alignment for Cohen, 2011.*
Arendash, Gary W., et al., "Behavioral Assessment of Alzheimer's Transgenic Mice Following Long-Term Aβ Vaccination: Task Specificity and Correlations Between Aβ Deposition and Spatial Memory", DNA and Cell Biology, 2001, 20, 737-744.
Banerji, Julian, et al., "A Lymphocyte-Specific Cellular Enhancer is Located Downstream of the Joining Region in Immunoglobulin Heavy Chain Genes", Cell, 1983, 33:729-740.
Barlow, Carrolee, et al., "Atm-Deficient Mice: A Paradigm of Ataxia Telangiectasia", Cell, 1996, 86, 159-171.
Bateman, Robert C., et al., "Evidence for Essential Histidines in Human Pituitary Glutaminyl Cyclase", Biochemistry, 2001, 40, 11246-11250.
Bateman, Robert C., "A Spectrophotometric Assay for Glutaminyl-Peptide Cyclizing Enzymes", Journal of Neuroscience Methods, 1989, 23-28.
Bhatia, Madhav, et al., "Pathopysiology of Acute Pancreatitis", Pancreatology, 2005, 5:132-144.
Binder, Elisabeth B., et al., "The Role of Neurotensin in the Pathophysiology of Schizophrenia and the Mechanism of Action of Antipsychotic Drugs", Society of Biological Psychiatry, 2001, 50, 856-872.
Bockers, Tobias M., et al., "Glutaminyl-Cyclase Expression in the Bovine/Procine Hypothalamus and Pituitary", Journal of Neuroendocrinology, 1995, 7, 445-453.
Borchelt, David R., et al., "Familial Alzheimer's Disease-Linked Presenilin 1 Variants Elevate Aβ1-42/1-40 Ratio In Vitro and In Vivo", Neuron, 1996, 17, 1005-1013.

(Continued)

Primary Examiner — Michael C. Wilson
(74) Attorney, Agent, or Firm — SNR Denton US LLP

(57) ABSTRACT

A transgenic non-human animal, in particular a transgenic mouse encoding Aβ peptide proteins, which have been implicated in Aβ peptide-related diseases. Cells and cell lines comprising transgenes encoding for Aβ peptide. Methods and compositions for evaluating agents that affect Aβ peptide, for use in compositions for the treatment of Aβ peptide-related diseases.

29 Claims, 16 Drawing Sheets

OTHER PUBLICATIONS

Bradford, Marion M., et al., "A Rapid and Sensitive Method for the Quantitation of Microgram quantities of Protein Utilizing the Principle of Protein-Dye Binding", Analytical Biochemistry, 1976, 72, 248-254.

Busby, Walker H., et al., "An Enzyme(s) that Converts Glutaminyl-Peptides Into Pyroglutamyl-Peptides Presence in Pituitary, Brain, Adrenal Medulla, and Lymphocytes", The Journal of Biological Chemistry, 1987 262, 8532-8536.

Byrne, G.W. and Ruddle, F.H., "Multiplex Gene Regulation: A Two-Tiered Apprach to Transgene Regulation in Transgenic Mice", Proc. Natl. Acad. Sci., 1989, 86:5473-5477.

Calame, Kathryn and Eaton, Suzanne, "Transcriptional Controlling Elements in the Immunoglobulin and T Cell Receptor Loci", Advances in Immunology, 1988, 43:235-275.

Casas, Caty, et al., "Massive CA1/2 Neuronal Loss with Intraneuronal and N-Terminal Truncated $A\beta_{42}$ Accumulation in a Novel Alzheimer Transgenic Model", American Journal of Pathology, 2004, 165, 1289-1300.

Ceballos-Picot, A. Nicole, et al., "Neuronal-Specific Expression of Human Copper-Zinc Superoxide Dismutase Gene in Transgenic Mice: Animal Model of Gene Dosage Effects in Down Syndrome", Brain Research, 1991, 552:198-214.

Citron, Martin, et al., "Mutant Presenilins of Alzheimer's Disease Increase Production of 42-Residue Amyloid β-Protein in Both Transfected Cells and Transgenic Mice", Nature Medicine, 1997, 3, 67-72.

Consalvo, Angelo P., et al., "A Rapid Fluorometric Assay for N-Terminal Glutaminyl Cyclase Activity Using High-Performance Liquid Chromatography", Analytical Biochemistry, 1988, 175, 131-138.

Cynis, Holger, et al., "Inhibition of Glutaminyl Cyclase Alters Pyroglutamate Formation in Mammalian Cells", Biochimica et Biophysica Acta, 2006, 1764, 1618-1625.

Dahl, Soren W., et al., "Carica Papaya Glutamine Cyclotransferase Belogns to a Novel Plant Enzyme Subfamily: Cloning and Characterization of the Recombinant Enzyme", protein Expression and Purification, 2000, 20, 27-36.

Dere, E., et al., "Connexin30-Deficient Mice Show Increased Emotionality and Decreased Rearing Activity in the Open-Field Along with Neurochemical Changes", European Journal of Neuroscience, 2003, 18, 629-638.

Edlund, Thomas, et al., "Cell-Specific Expression of the Rat Insulin Gene: Evidence for Role of Two Distrinct 5' Flanking Elements", Science, 1985, 230:912-916.

El Moussaoui, A., et al., "Revisiting the Enzymes Stored in the Laticifers of Carica Papaya in the Context of their Possible Participation in the Plant Defence Mechanism", Cell. Mol. Life Sci., 2001, 58, 556-570.

Erbel-Sieler, Claudia, et al., "Behavioral and Regulatory Abnormalities in Mice Deficient in the NPAS1 and NPAS3 Transcription Factors", PNSA, 2004, 101, 13648-13653.

Fischer, Wolfgang H. and Spiess, Joachim, "Identification of a Mammalian Glutaminyl Cyclase Converting Glutaminyl into Pyroglutamyl Peptides", Proc. Natl. Acad. Sci. USA, 1987, 84, 3628-3632.

Forss-Petter, Sonja, et al., "Transgenic Mice Expressing β-Galactosidase in Mature Neurons Under Neuron-Specific Enolase Promoter Control", Neuron 5, 1990, 187-197.

Fraser, Lynn R. and Adeoya-Osiguwa, Susan A., "Fertilization Promoting Peptide—A Possible Regulator of Sperm Function in Vivo", Vitamins and Hormones, 2001, 63, 1-28.

Frenois, Francois, et al., "Neural Correlates of the Motivational and Somatic components fo the Naloxone-Precipitated Morphine Withdrawal", European Journal of Neuroscience, 2002, 16, 1377-1389.

Funato, Hiromasa, et al., "Quantitation of Amyloid β-Protein (Aβ) in the Cortex During Aging and in Alzheimer's Disease", American Journal of Pathology, 1998, 152, 1633-1640.

Garden, Rebecca W. et al., "Formation of N-Pyroglutamyl Peptides from N-Glu and N-Gln Precursors in Aplysia Neurons", Journal of Neurochemistry, 1999, 72, 676-681.

Geddes, James W. et al., "N-terminus Truncated β-amyloid Peptides and C-Terminus Truncated Secreted Forms of Amyloid Precursor Protein: Distinct Roles in the Pathogenesis of Alzheimer's Disease", Neurobiol Aging, 1999, 20, 75-79.

Gerard, Craig and Rollins, Barrett J., "Chemokines and Disease", Nature Immunology 2, 2001, 5,108-115.

Gerlai, Robert, "A New Continuous Alternation Task in T-Maze Detects Hippocampal Dysfunction in Mice a Strain Comparison and Lesion Study", Behav Brain Res., 1998, 95, 91-101.

Ghiso, Jorge, et al., "Chromosome 13 Dementia Syndromes as Models of Neurodegeneration", Amyloid. 8, 2001, 277-284.

Gill, Stanley C. and Von Hippel, Peter H., "Calculation of Protein Extinction Coefficients from Amino Acid Sequence Data", Analytical Biochemistry, 1989, 182, 319-326.

Glenner, G.G. and Wong, C.W., "Alzeimer's Disease" Initial Report of the Purification and Characterization of a Novel Cerebrovascular Amyloid Protein, Biochem Biophys Res Comm, 1984, 120, 885-890.

Gorevic, Peter D., et al., "Isolation and Partial Characterization of Neurofibrillary Tangles and Amyloid Plaque Core in Alzheimer's Disease: Immunohistological Studies", J Neuropathol Exp Neurol, 1986, 45, 647-664.

Gossen, Manfred and Bujard, Hermann, "Tight Control of Gene Expression in Mammalian Cells by Tetracycline-Responsive Promoters", Proc. Natl. Acad. Sci., 1992, 89:5547-5551.

Guntert, A., et al., "High Sensitivity Analysis of Amyloid-Beta Peptide Composition in Amyloid Deposits from Human and PS2App Mouse Brain", Neuroscience, 2006, 143, 461-475.

Haass, Christian and Selkoe, Dennis J., "Cellular Processing and β-Amyloid Precursor Protein and the Genesis of Amyloid β-Peptide", Cell, 1993, 75, 1039-1042.

Harigaya, Yasuo, et al., "Amyloid β Protein Starting Pyroglutamate at Position 3 is a Major Component of the Amyloid Deposits in the Alzheimer's Disease Brain", Biochem Biophys Res Commun, 2000, 276, 422-427.

Haskell, R.E. and Bowen, R.A., "Efficient Production of Transgenic Cattle by Retroviral Infection of Early Embryos", Molecular Reproduction and Development, 1995, 40: 386-390.

He, Weilan and Barrow, Colin J., "The Aβ 3-Pyroglutamyl and 11-Pyroglutamyl Peptides Found in Senile Plaque Have Greater β-Sheet Forming and Aggregation Propensities in Vitro than Full-Length Aβ", Biochemistry, 1999, 38, 10871-10877.

He, Xi, et al., "Expression of a Large Family of POU-Domain Regulatory Genes in Mammalian Brain Development", Nature 1989, 340:35-42.

Hosoda, Ritsuko, et al., "Quantification of Modified Amyloid β Peptides in Alzhemer Disease and Down Syndrome Brains", Journal of Neuropathology and Experimental Neurology, 1998, 57, 1089-1095.

Huse, Jason T., et al., "β-Secretase Processing in the Trans-Golgi Network Preferentially Generates Truncated Amyloid Species that Accumulate in Alzheimer's Disease Brain", The Journal of Biological Chemistry, 2002, 277(18):16278-16284.

Itagaki, S., et al., "Relationship of Microglia and Astrocytes to Amyloid Deposits of Alzheimer Disease", Journal of Neuroimmunology, 1989, 24, 173-182.

Iwatsubo, Takeshi, et al, "Full-Length Amyloid-β(1-42(43)) and Amino-Terminally Modified and Truncated Amyloid-β42(43) Deposit in Diffuse Plaques", American Journal of Pathology, 1996, 149, 1823-1830.

Jaenisch, Rudolf, "Germ Line Integration and Mendelian Transmission of the Exogenous Moloney Leukemia Virus", Proc. Nat. Acad. Sci., 1976, 73:1260-1264.

Jaenisch, Rudolf, "Transgenic Animals", Science, 1988, 240:1468-1474.

Jahner, Detlev, et al., "De novo Methylation and Expression of Retroviral Genomes During Mouse Embryogenesis", Nature, 1982, 298:623-628.

Jahner, Detley, et al., "Insertion of the Bacterial gpt Gene into the Germ Line of Mice by Retroviral Infection", Proc. Natl. Acad. Sci, 1985, 82:6927-6931.

Kang, Jie, et al., "The Precursor of Alzheimer's Disease Amyloid A4 Protein Resembles a Cell-Surface Receptor", Nature, 1987, 325, 733-736.

Kitamoto, Shiro, et al., "Stress and Vascular Resposnes: Anti-Inflammatory Therapeutic Strategy Against Atherosclerosis and Restenosis After Coronary Intervention", J Pharmacol Sci 2003, 91, 192-196.

Klafki, Hana W., et al., "Electrophoretic Separation of βA4 Peptides (1-40) and (1-42)", Analytical Biochemistry, 1996, 237, 24-29.

Kuo, Y-Min, et al., "Isolation, Chemical Characterication, and Quantitation of Aβ 3-Pyroglutamyl Peptide from Neuritic Plaques and Vascular Amyloid Deposits", Biochemical and Biophysical Research Communications, 1997, 237, 188-191.

Kuo, Yu-Min, Comparative Analysis of Amyloid-β Chemical Structure and Amyloid Plaque Morphology of Transgenic Mouse and Alzheimer's Disease Brains:, The Journal of Biological Chemistry, 2001, 276, 12991-12998.

Kuo, Yu-Min, et al., "Irreversible Dimerization/Tetramerization and Post-Translational Modifications Inhibit Proteolytic Degradation of Aβ Peptides of Alzheimer's Disease", Biochimica et Biophysica Acta, 1998, 1406, 291-298.

Lalowski, Maciej, et al., "The "Nonamyloidogenic" p3 Fragment (Amyloid β17-42) is a Major Constituent of Down's Syndrome Cerebellar Preamyloid", The Journal of Biological Chemistry, 1996, 271, 33623-33631.

Lavitrano, Marialulsa, et al., "Sperm Cells as Vectors for Introducing Foreign DNA into Eggs: Genetic Transformation of Mice", Cell, 1989, 57:717-723.

Lee, Frank, et al., "Glucocorticoids Regulate Expression of Dihydrofolate Reductase cDNA in Mouse Mammary Tumour Virus Chimaeric Plasmids", Nature, 1981, 294:228-232.

Lee, H.J., et al., "Transgenic Mouse Model that Accumulates a Senile Human Brain-Specific Pathological Form of Amyloid-Beta Peptide, Abeta3(pE)-42", Scoeity for Neuroscience Abstracts, 2000, 26, 1-2.

Lemere, C.A., et al., "Sequence of Deposition of Heterogeneous Amyloid β-Peptides and APO E in Down Syndrome: Implications for Initial Events in Amyloid Plaque Formation", Neurobiology of Disease, 1996, 3, 16-32.

Lemere, Cynthia A., et al., "The E280A Presenilin 1 Alzheimer Mutation Produces Increased Aβ42 Deposition and Severe Cerebellar Pathology", Nature Medicine, 1996, 2, 1146-1150.

Lo, Cecilia W., "Transformation by Iontophoretic Microinjection of DNA: Multiple Integrations Without Tandem Insertions", Molecular and Cellular Biology, 1983, 3:1803-1814.

Luini, Walter, et al., "Species-Specificity of Monocyte Chemotactic Protein-1 and -3", Cytokine, 1994, 6, 28-31.

Mann, D.M.A. and Iwatsubo, T., "Diffuse Plaques in the Cerebellum and Corpus Straiatum in Down's Syndrome Contain Amyloid β Protein (Aβ) only in the form of Aβ 42(43)", Neurodegeneration, 1996, 5, 115-120.

Masters, Colin L., et al., "Amyloid Plaque Core Protein in Alzheimer Disease and Down Syndrome", Proc. Natl. Acad. Sci., 1985, 82, 4245-4249.

Maue, R.A., et al., "Neuron-Specific Expression of the Rat Brain Type II Sodium Channel Gene is Directed by Upstream Regulatory Elements", Neuron, 1990, 4:223-231.

Messer, Michael, "Iron Metabolism in Avian Erythroblastosis", Nature, 1963, 4874, 1299.

Miravalle, Leticia, et al., "Amino-Terminally Truncated Aβ Peptide Species are the Main component of Cotton Wool Plaques", Biochemistry, 2005, 44, 10810-10821.

Moran, Paula M., et al., "Age-Related Learning Deficits in Transgenic Mice Expressing the 751-Amino Acid Isoform of Human β-Amyloid Precursor Protein", Proc. Natl. Acad. Sci, 1995, 92, 5341-5345.

Mori, H., et al., "Mass Spectrometry of Purified Amyloid β Protein in Alzheimer's Disease", The Journal of Biological Chemistry, 1992, 267, 17082-17086.

Morris, Richard G., "Spatial Localization does not Require the Presence of Local Cues", Learning and Motiviation, 1981, 12:239-260.

Nguyen, Trent, et al., "Clioquinol Down-Regulates Mutant Huntingtin Expression in Vitro and Mitigates Pathology in a Huntington's Disease Mouse Model", Proc Natl Acad Sci, 2005, 102, 11840-11845.

No, David, et al., "Ecdysone-Inducible Gene Expression in Mammalian Cells and Transgenic Mice", Proc. Natl. Acad. Sci., 1996, 93:3346-3351.

Piccini, Alesandra, et al., "Association of a Presenilin 1 S170F Mutation with a Novel Alzheimer Disease Molecular Phenotype", Arch Neurol, 2007, 64, 738-745.

Piccini, Alesandra, et al., "β-Amyloid is Different in Normal Aging and in Alzheimer Disease", Journal of Biological Chemistry, 2005, 280, 34186-34192.

Pike, Christian J., et al., Amino-Terminal Deletions Enhance Aggregation of β-amyloid Peptides in Vitro, The Journal of Biological Chemistry, 1995, 270, 23895-23898.

Pinkert, Carl A., et al., "An Albumin Enhancer Located 10 kb Upstream Functions Along with its Promoter to Direct Efficient, Liver-Specific Expression in Transgenic Mice", Genes & Development, 1987, 1:268-277.

Pohl, Thomas, et al., "Primary Structure and Functional Expression of a Glutaminyl Cyclase", Proc. Natl. Acad. Sci, 1991, 88, 10059-10063.

Prokal, Laszlo, et al., "Metabolism-Based Brain-Targeting System for a Thyrotropin-Releasing Hormones Analogue", J. Med. Chem., 1999, 42, 4563-4571.

Queen, Cary and Baltimore, David, "Immunoglobulin Gene Transcription Is Activiated by Downstream Sequence Elements", Cell, 1983, 33:741-748.

Ray, Prabit, et al., "Ectopic Expression of a c-kit$^{w42}$ Minigene in Transgenic Mice: Recapitulation of $W$ Phenotypes and Evidence for c-kit Function in Melanoblast Progenitors", Genes & Development, 1991, 5:2265-2273.

Rogers, Derek, et al., "Behavioral and Functional Analysis of Mouse Phenotype: SHIRPA, a Proposed Protocol for Comprehensive Phenotype Assessment", Mammalian Genome, 1997, 8, 711-713.

Rostagno, Agueda, et al., "Complement Activation in Chromosome 13 Dementias", The Journal of Biological Company, 2002, 277, 49782-49790.

Russo, Claudio, et al, "Heterogeneity of Water-Soluble Amyloid β-Peptide in Alzheimer's Disease and Down's Syndrome Brains", FEBS Letter, 1997, 409, 411-416.

Russo, Claudio, et al., "Identification of Amino-Terminally and Phosphotyrosine-Modified Carboxy-Terminal Fragments of the Amyloid Precursor Protein in Alzheimer's Disease and Down's Syndrome Brain", Neurobiology of Disease, 2001, 8, 173-180.

Russo, Claudio, et al., "Presenilin-1 Mutations in Alzheimer's Disease", Nature, 2000, 405, 531-532.

Russo, Claudio, et al., "Pyroglutamate-Modified Amyloid β-Peptides—AβN3(pE)—Strongly Affect Cultured Neuron and Astrocyte Survival", Journal of Neurochemistry, 2002, 82, 1480-1489.

Saido, Takaomi C., "Involvement of Polyglutamine Endolysis Followed by Pyroglutamate Formation in the Pathogenesis of Triplet Repeat/Polyglutamine-Expansion Diseases", Medical Hypothesis, 2000, 54(3):427-429.

Saido, Takaomi C., et al., "Dominant and Differential Deposition of Distinct β-Amyloid Peptide Species, $Aβ_{N3(pE)}$, in Senile Plaques", Neuron, 1995, 14, 457-466.

Sasahara, Masakiyo, et al., "PDGF B-Chaim in Neurons of the Central Nervous System, Posterior Pituitary, and in a Transgenic Model", Cell, 1991, 64:217-227.

Saido, Takaomi, C. et al., "Amino- and Carboxyl-Terminal Heterogeneity of β-amyloid Peptides Deposited in Human Brain", Nerosci Lett, 1996, 215, 173-176.

Schilling, Stephan, et al., "Glutaminyl Cyclases Unfold Glutamyl Cyclase Activity Under Mild Acid Conditions", FEBS Letters, 2004, 563, 191-196.

Schilling, Stephan, et al., "On the Seeding and Oligomerization of pGlu-Amyloid Peptides (in vitro)", Biochemistry, 2006, 45, 12393-12399.

Selkoe, Dennis J., "Alzheimer's Disease: Genes, Proteins, and Therapy", Pysiol Rev, 2001, 81, 741-766.

Selkoe, Dennis J., "The Cell Biology of β-Amyloid Precursor Protein and Presenilin in Alzheimer's Disease", Cell Biology, 1998, 447-453.

Selkoe, Dennis J., et al., "Isolation of Low-Molecular-Weight Proteins from Amyloid Plaque Fibers in Alzheimer's Disease", Journal of Neurochemistry, 1986, 46, 1820-1834.

Shirotani, Keiro, et al., "Generation of Amyloid β Peptide with Pyroglutamate at Position 3 in Primary Cortical Neurons", Neuroscience Letters, 2002, 327, 25-28.

Simons, Mikael, et al., "Amyloidogenic Processing of the Human Amyloid Precursor Protein in Primary Cultures of Rat Hippocampal Neurons", The Journal of Neuroscience, 1996, 16, 899-908.

Spittaels, Kurt, et al., Proiment Axonopathy in the Brain and Spinal Cord of Transgenic Mice Overexpressing Four-Repeat Human tau Protein:, American Journal of Pathology, 1999, 155, 2153-2165.

Stewart, Colin L., et al., "Expression of Retroviral Vectors in Transgenic Mice Obtained by Embryo Infection", The EMBO Journal, 1987, 6:383-388.

Sturchler-Pierrat, Christine, et al., "Two Amyloid Precursor Protein Transgenic Mouse Models with Alzheimer Disease-Like Pathology", Proc. Natl. Acad. Sci., 1997, 94:13287-13292.

Subramaniam, Arun, et al., "Tissue-Specific Regulation of the a-Myosin Heavy Chain Gene Promoter in Transgenic Mice", The Journal of Biological Chemistry, 1991, 266:24613-24620.

Tekirian, Tina L., et al., "N-Terminal Heterogeneity of Parenchymal and Cerebrovascular Aβ Deposits", Journal of Neuropathology and Experimental Neurology, 1998, 57, 76-94.

Tekirian, Tina L., et al., "Toxicity of Pyroglutaminated Amyloid β-Peptides 3(pE)-40 and -42 is Similar to that of Aβ-40 and -42", Journal of Neurochemistry, 1999, 73, 1584-1589.

Terry, Robert D. and Katzman, Robert, "Senile Dementia of the Alzheimer Type", NAnn Neurol, 1983, 14, 497-506.

Thompson, Simon, et al., "Germ Line Transmission and Expression of a Corrected HPRT Gene Produced by Gene Targeting in Embryonic Stem Cells", Cell, 1989, 56:313-321.

Tomidokoro, Yasushi, et al., "Familial Danish Dementia: Co-Existence of Danish and Alzheimer Amyloid Subunits (ADan and Aβ) in the Absence of Compact Plaques", J. Biol. Chem, 2005, 280, 36883-36894.

Van Damme, Jo., et al., "The Role of CD26/DPP IV in Chemokine Processing", Chem Immunol., 1999, 72, 42-56.

Van Der Putten, Herman., et al., "Efficient Insertion of Genes into the Mouse Germ Line Via Retroviral Vectors", Proc. Natl. Acad. Sci., 1985, 82:6148-6152.

Vidal, Ruben., et al., A Stop-Codon Mutation in the *BRI* Gene Associated with Familial British Dementia, Nature, 1999, 399, 776-781.

Winoto, Astar and Baltimore, David, "A Novel, Inducible and T Cell-Specific Enhancer Located at the 3' End of the T Cell Receptor Locus", EMBO Journal, 1989, 8:729-733.

Wirths, Oliver, et al., "Age-Dependent Azonal Degeneration in an Alzheimer Mouse Model", Neurobiology of Aging, 2007, 28, 1689-1699.

Wirths, Oliver, et al., "Deficits in Working Memory and Motor Performance in the APP/PS1ki Mouse Model for Alzheimer's Disease", Neurobiology of Aging, 2008, 29, 891-901.

Yao, Tao-Pang, et al., "Functional Ecdysone Receptor is the Produce of EcR and *Ultraspiracle* Genes", Letters to Nature, 1993, 366:476-479.

Gololobov, Mikhail Yu, et al., "Substrate and Inhibitor Specificity of Glutamine Cyclotransferase (QC)", Biol Chem Hoppe Seyler, 1996, 377, 395-398.

Zerhouni, Samira, et al., "Purification and Characterization of Papaya Glutamine Cyclotransferase, a Plant Enzyme Highly Resistant to Chemical, Acid and Thermal Denaturation", Biochimica et Biophysics Acta, 1989, 138, 275-290.

\* cited by examiner tgN3Q-42

TgN3E-42

SEQUENCE LISTING

<160> NUMBER OF SEQ ID NOS: 44

<210> SEQ ID NO 1
<211> LENGTH: 40
<212> TYPE: PRT
<213> ORGANISM: Artificial sequence
<220> FEATURE:
<223> OTHER INFORMATION: Synthetic peptide

<400> SEQUENCE: 1

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 2
<211> LENGTH: 40
<212> TYPE: PRT
<213> ORGANISM: Artificial sequence
<220> FEATURE:
<223> OTHER INFORMATION: Synthetic peptide

<400> SEQUENCE: 2

Gln Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 3
<211> LENGTH: 38
<212> TYPE: PRT
<213> ORGANISM: Artificial sequence
<220> FEATURE:
<223> OTHER INFORMATION: Synthetic peptide

<400> SEQUENCE: 3

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 4
<211> LENGTH: 38
<212> TYPE: PRT
<213> ORGANISM: Artificial sequence
<220> FEATURE:
<223> OTHER INFORMATION: Synthetic peptide

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 5
<211> LENGTH: 7176
<212> TYPE: DNA
<213> ORGANISM: Artificial sequence
<220> FEATURE:
<223> OTHER INFORMATION: Synthetic nucleotide

<400> SEQUENCE: 5

| | | | | |
|---|---|---|---|---|
| gaattcagag | accgggaacc | aaactagcct | ttaaaaaaca | taagtacagg | agccagcaag | 60 |
| atggctcagt | gggtaaaggt | gcctaccagc | aagcctgaca | gcctgagttc | agtccccacg | 120 |
| aactacgtgg | taggagagga | ccaaccaact | ctggaaatct | gttctgcaaa | cacatgctca | 180 |
| cacacacaca | cacaaatagt | ataaacaatt | ttaaatttca | tttaaaaata | atttgtaaac | 240 |
| aaaatcatta | gcacaggttt | tagaaagagc | ctcttggtga | catcaagttg | atgctgtaga | 300 |
| tggggtatca | ttcctgagga | cccaaaaccg | ggtctcagcc | tttccccatt | ctgagagttc | 360 |
| tctcttttct | cagccactag | ctgaagagta | gagtggctca | gcactgggct | cttgagttcc | 420 |
| caagtcctac | aactggtcag | cctgactact | aaccagccat | gaagaaacaa | ggagtggatg | 480 |
| ggctgagtct | gctgggatgg | gagtggagtt | agtaagtggc | catggatgta | atgaccccag | 540 |
| caatgctggc | tagaaggcat | gcctcctttc | cttgtctgga | gacggaacgg | gatcatcttg | 600 |
| tactcacaga | agggagaaca | ttctagctgg | ttgggccaaa | atgtgcaagt | tcacctggag | 660 |
| gtggtggtgc | atgcttttaa | ctccagtact | caggaggcag | ggccaggtgg | atctctgtga | 720 |
| gttcaagacc | agcctgcact | atggagagag | ttttgggaca | gccagagtta | cacagaaaaa | 780 |
| tcctggtgga | aaatctgaaa | gaagagaga | agaaagaaa | gaaagaaaga | aagaaagaaa | 840 |
| gaaagaaaga | agaaagaaa | gaaagaaaga | aaggaagaaa | gaaagaaaga | gtggcaggca | 900 |
| ggcaggcagg | aggaaggaag | gaaggaagga | ggaaggaag | gaaggaagga | aggaaggaag | 960 |
| gaaggaagga | aggaaaatag | gtgcgacttc | aagatccgga | gttacaagca | gaatgcactg | 1020 |
| tttccctaac | agggccaagt | gttttgagta | actgaaggtg | ggcatgatgc | ctgggaagca | 1080 |
| gaaacaagcc | aggcagatgc | acccccttgcc | ttgcttccga | agggctgcag | tagcatggaa | 1140 |
| aacatggaaa | acaaccaatc | cattcccttt | gctgatataa | caggctccaa | agccaaaacc | 1200 |
| tgtcactgga | ggctcaagag | cagatctcca | gccaagaggc | aaaggaatgg | gggaagctgg | 1260 |
| agggcctccc | tctggttatc | caggcttctg | aaggttcaag | caaagaaagg | gttacaacct | 1320 |
| taaaaggaga | gcgtcccggg | gtatgggtag | aagactgctc | caccccgacc | cccagggtcc | 1380 |
| ctaaccgtct | tttccctggg | cgagtcagcc | caatcacagg | actgagagtg | cctctttagt | 1440 |
| agcagcaagc | cacttcggac | acccaaatgg | aacacctcca | gtcagccctc | gccgaccacc | 1500 |
| ccaccccctc | catcctttc | cctcagcctc | cgattggctg | aatctagagt | ccctccctgc | 1560 |
| tccccctct | ctcccacccc | ctggtgaaaa | ctgcgggctt | cagcgctggg | tgcagcaact | 1620 |
| ggaggcgttg | gcgcaccagg | aggaggctgc | agctagggga | gtccaggtga | gagcaggccg | 1680 |
| acgggaggga | cccgcacatg | caaggaccgc | cgcaggggcga | ggatgcaagc | cttcccagc | 1740 |
| tacagttttg | ggaaaggata | ccagggcgct | cctatatggg | ggcgcgggaa | ctggggaaag | 1800 |
| aaggtgctcc | caggtcgagg | tgggagagga | aggcagtgcg | gggtcacggg | ctttctccct | 1860 |
| gctaacggac | gctttcgaag | agtgggtgcc | ggaggagaac | catgaggaag | gacatcaagg | 1920 |

```
acagcctttg gtccccaagc tcaaatcgct ttagtggtgc aatagaggg aggaggtggg    1980 tggcaaactg agggagtcc ccagcgggtg acctcgtggc tggctgggtg cggggcaccg    2040
caggtaagaa aaccgcaatg ttgcgggagg ggactgggtg gcaggcgcgg gggaggggaa    2100
agctagaaag gatgcgaggg agcggagggg ggagggagcg ggagaatctc aactggtaga    2160
ggaagattaa aatgaggaaa tagcatcagg gtggggttag ccaagccggg cctcagggaa    2220
agggcgcaaa gtttgtctgg gtgtgggctt aggtgggctg ggtatgagat tcggggcgcc    2280
gaaaacactg ctgcgcctct gccaaatcac gctacccctg tatctagttc tgccaggctt    2340
ctccagcccc agcccccaatt cttttctcta gtgttccccc ttccctcccc tgaatctcaa    2400
gcccacactc cctcctccat aacccactgt tatcaaatcc aagtcatttg ccacccaaca    2460
accatcagga ggcggaagca gacgggagga gtttgagatc aacttgggct acatcacgag    2520
ttccaggctc accaaggctt cttaaggaga ccttgtctct aaaattaatt aattaattaa    2580
ttaatagtcc cctttctctg ccacagaacc ttgggatctg gctcctggtc gcagctcccc    2640
ccaccccagg ctgacattca ctgccatagc ccatccggaa atcctagtct atttccccat    2700
ggatcttgaa ctgcagagag aatggcagag tggcccgccc tgtgcaaagg atgttcctag    2760
cctaggtgga gctcgcgaac tcgcagactg tgcctctctt gggcaaggac aggctagaca    2820
gcctgccggt gtgttgagct agggcactgt ggggaaggca gagaacctgt gcagggcagc    2880
aatgaacaca ggaccagaaa actgcagccc taggaacact caagagctgg ccatttgcaa    2940
gcatctctgg cctccgtgct tctcactcat gtcccatgtc ttatacaggc ctctgtggca    3000
cctcgcttgc ctgatctcat ccctagccgt taagctttct gcatgactta tcacttgggg    3060
cataatgctg gatacctacc attttcttag accccatcaa aatcctatttt gagtgtacgg    3120 ttcggagaac ctcatttatc cggtaaatgt cttttactct gctctcaggg agctgaggca    3180
ggacatcctg agatacattg ggagaggaga tacagtttca ataaaataat aggttgggtg    3240
gaggtacatg cctataatgc caccactcag gaaatggtgg cagcttcgtg agtttgaggc    3300
caacccaaga aacatagtga aaccctgtca gtaaataagt aagcaagtat ttgagtatct    3360
actatatgct agggctgacc tggacattag gggtcatctt ctgaacaaac tagtgcttga    3420
gggaggtatt tgggggtttt gtttgtttaa tggatctgaa tgagttccag agactggcta    3480
cacagcgata tgactgagct taacacccct aaagcataca gtcagaccaa ttagacaata    3540
aaaggtatgt atagcttacc aaataaaaaa attgtatttt caagagagtg tctgtctgtg    3600
tagccctggc tgttcttgaa ctcactctgt agaccaggct ggcctggaaa tccatctgcc    3660
tgcctctgcc tctctgcctc tctgcctctc tgcctctctc tctgcctctc tctgcctctc    3720
tctgcccctc tctgcccctc tctgcccctc tctgcccctc tctgccgccc tctgccttct    3780
gccctctgcc ctctggcctc tggctctgcc cctctgccct ctggcctctg gcctctgcct    3840
ctgcctcttg agtgctggaa tcaaaggtgt gagctctgta ggtcttaagt tccagaagaa    3900
agtaatgaag tcacccagca gggaggtgct cagggacagc acagacacac acccaggaca    3960
taggctccca cttccttggc tttctctgag tggcaaagga ccttaggcag tgtcactccc    4020
taagagaagg ggataaagag aggggctgag gtattcatca tgtgctccgt ggatctcaag    4080 cccctcaaggt aaatggggac ccacctgtcc taccagctgg ctgacctgta gctttccca    4140 ccacagaatc caagtcggaa ctcttggcac ctagaggatc tcgagatgca gggaccttgg    4200
ctgatgatgg ctctggcttt gatcttcgtg ctaactggta tccccaaatc ctgcgccttg    4260
ctggaagcag cccaggagga aggtgctgtg actcctgacc ttccaggcct ggagaaagtc    4320
```

```
caggtccggc cagaacgtcg attcttgagg aaagacctcc agcgtgtgcg aggggacctt    4380
ggtgctgcct tagattcctg gatcacaaaa cgcgagttcc gacatgactc aggatatgaa    4440
gttcatcatc aaaaattggt gttctttgca gaagatgtgg gttcaaacaa aggtgcaatc    4500
attggactca tggtgggcgg tgttgtcata gcgtaactcg aggtccttcc tctgcagagg    4560
tcttgcttct cccggtcagc tgactccctc cccaagtcct tcaaatatct cagaacatgg    4620
ggagaaacgg ggaccttgtc cctcctaagg aaccccagtg ctgcatgcca tcatcccccc    4680
caccctcgcc cccaccccg ccacttctcc ctccatgcat accactagct gtcattttgt     4740
actctgtatt tattccaggg ctgcttctga ttatttagtt tgttcttcc ctggagacct     4800 gttagaacat aagggcgtat ggtgggtagg ggaggcagga tatcagtccc tggggcgagt    4860
tcctccctgc caaccaagcc agatgcctga agagatatg gatgagggaa gttggactgt     4920
gcctgtacct ggtacagtca tactctgttg aaagaatcat cggggagggg ggggggggct    4980
caagatggga gagctctgct gagcctttgt ggaccatcca atgaggatga gggcttagat    5040
tctaccaggt cattctcagc caccacacac aagcgctctg ccatcactga gaagccccc    5100 tagggctctt gggccagggc acactcagta aagatgcagg ttcagtcagg gaatgatggg    5160
gaaaggggta ggaggtgggg gagggatcac cccctcctct aaaacacgag cctgctgtct    5220
ccaaaggcct ctgcctgtag tgagggtggc agaagaagac aaggagccag aactctgact    5280
ccaggatcta agtccgtgca ggaagggat cctagaacca tccggttgga cccagcttac     5340
caagggagag cctttattct tctttccctt gccctctgt gccagcccct cttgctgtcc     5400
ctgatccccc agacagcgag agtcttgcaa cctgcctctt ccaagacctc ctaatctcag    5460
gggcaggcgg tggagtgaga tccggcgtgc acacttttg gaagatagct ttcccaagga    5520
tcctctcccc cactggcagc tctgcctgtc ccatcaccat gtataatacc accactgcta    5580
cagcatctca ccgaggaaag aaaactgcac aataaaacca agcctctgga gtgtgtcctg    5640
gtgtctgtct cttctgtgtc ctggcgtctg tctcttctgt gttcttccaa ggtcagaaac    5700
aaaaaccaca cacttcaacc tggatggctc ggctgagcac ttctgtgtgc agaaggtcca    5760
accagactct ggggtacccc ggccctccct attcccttgc ctcctgtctc ccgcttttta    5820
tagctcccta tgctgggctt ctctggagag tgaaatcttt gcccaaatca atgcgcattc    5880
tctctgctga gtcatctggc gacagcagtt gagttcaccc gccaacacat gggcccagct    5940
atgtagccga accctggctc tggaagtgcc agggactttg tgcataagta tgtaccatgc    6000
ccttttttca cagtcctagc tctgcagaag tgcagcctga aggcctgtct gctgagagga    6060
catgccctgg agcctgaaa caggcacagt gggaggagga acggaggatg acaggcatca    6120
ggccctcagt ccaaaagcaa ccacttgaga atgggctgga gtacgaaaca tggggtcccg    6180
tccctggatc cctcctcaaa gagtaataag taaaatataa acaggtaccc caggccgttc    6240
tgggtttggg ttgtaatggg atccatttgc agagaactat tgagacagcc cagccgtact    6300
gtgacaggca atgtggggga ggaggttgaa tcacttggta tttagcatga atagaataat    6360
tccctgaaca tttttcttaa acatccatat ctaaattacc accactcgct cccagtcttc    6420 ctgccttttgc gccagcctcc tgtctggcca tgcctgaaga aggctggaga agccacccac    6480
ctcaggccat gacactgcca gccacttggc aggtgcagcc aaacctgagc tgtcccagaa    6540
agggacattc tcaagaccca ggcaccctga tcagcactga cttggagcta caagtgtcat    6600
gccagaaaag tctctaagaa aaccttttca gggaaaggg ggtgactcaa caccgggcaa    6660
gtttgggaag ccccacccct cgagtgatgg aagagcagat aggaagcctc agaagagaga    6720
```

```
caccggcacc caggtaacgt tcctcatgtg gtctctgtca cactaggtgc tcttccctgg    6780
acatctccgt gaccacactc tcagttctta gggagatgcg ggtgctctct gaggctatct    6840
cagagttgca gattctgagg cctagagtga ctacagtcag cctaggaagc cacagaggac    6900
tgtggaccag gagggcagaa gaggagaagg gaagaaaaac catcagatag gacttgcaat    6960
gaaactaacc caagacaatc ataatgcaga caggaatgtt aaaggcgttc agcagctggc    7020
catgacaccc atctgtccct ctggccaagt cagcaagcct ggaagacctg ggactcctgc    7080
ccatatgtcc taagctccca cccacccact cgttcactgt ccttattctc tctctacctt    7140
cagccactta gtttcctacc ttaagtccta gaattc                              7176

<210> SEQ ID NO 6
<211> LENGTH: 363
<212> TYPE: DNA
<213> ORGANISM: Artificial sequence
<220> FEATURE:
<223> OTHER INFORMATION: Synthetic nucleotide

<400> SEQUENCE: 6
ctcgagatgc agggaccttg gctgatgatg gctctggctt tgatcttcgt gctaactggt     60
atccccaaat cctgcgcctt gctggaagca gcccaggagg aagGtgctgt gactcctgac    120
cttccaggcc tggagaaagt ccaggtccgg ccagaacgtc gattcttgag gaagaccctc    180
cagcgtgtgc gagggggacct tggtgctgcc ttagattcct ggatcacaaa acgcgagttc    240
cgacatgact caggatatga agttcatcat caaaaattgg tgttctttgc agaagatgtg    300
ggttcaaaca aggtgcaat cattggactc atggtgggcg gtgttgtcat agcgtaactc     360
gag                                                                  363

<210> SEQ ID NO 7
<211> LENGTH: 7176
<212> TYPE: DNA
<213> ORGANISM: Artificial sequence
<220> FEATURE:
<223> OTHER INFORMATION: Synthetic nucleotide

<400> SEQUENCE: 7
gaattcagag accgggaacc aaactagcct ttaaaaaaca taagtacagg agccagcaag     60
atggctcagt gggtaaaggt gcctaccagc aagcctgaca gcctgagttc agtccccacg    120
aactacgtgg taggagagga ccaaccaact ctggaaatct gttctgcaaa cacatgctca    180
cacacacaca cacaaatagt ataaacaatt ttaaatttca tttaaaaata atttgtaaac    240
aaaatcatta gcacaggttt tagaaagagc tccttggtga catcaagttg atgctgtaga    300
tggggtatca ttcctgagga cccaaaaccg ggtctcagcc tttccccatt ctgagagttc    360
tctcttttct cagccactag ctgaagagta gagtggctca gcactgggct cttgagttcc    420
caagtcctac aactggtcag cctgactact aaccagccat gaagaaacaa ggagtggatg    480
ggctgagtct gctgggatgg gagtggagtt agtaagtggc catggatgta atgaccccag    540
caatgctggc tagaaggcat gcctcctttc cttgtctgga gacggaacgg gatcatcttg    600
tactcacaga agggagaaca ttctagctgg ttgggccaaa atgtgcaagt tcacctggag    660
gtggtggtgc atgcttttaa ctccagtact caggaggcag ggcaggtgg atctctgtga     720 gttcaagacc agcctgcact atggagagag ttttgggaca gccagagtta cacagaaaaa    780
tcctggtgga aaatctgaaa gaagagagag aagaagaaa gaaagaaaga aagaaagaaa    840
gaaagaaaga aagaaagaaa gaagaaaga aaggaagaaa gaaagaaaga gtggcaggca    900
```

```
ggcaggcagg aggaaggaag gaaggaagga aggaaggaag gaaggaagga aggaaggaag    960
gaaggaagga aggaaaatag gtgcgacttc aagatccgga gttacaagca gaatgcactg   1020
tttccctaac agggccaagt gttttgagta actgaaggtg ggcatgatgc ctgggaagca   1080
gaaacaagcc aggcagatgc acccctggcc ttgcttccga agggctgcag tagcatggaa   1140
aacatggaaa acaaccaatc cattcccttt gctgatataa caggctccaa agccaaaacc   1200
tgtcactgga ggctcaagag cagatctcca gccaagaggc aaaggaatgg gggaagctgg   1260
agggcctccc tctggttatc caggcttctg aaggttcaag caaagaaagg gttacaacct   1320
taaaaggaga gcgtcccggg gtatgggtag aagactgctc caccccgacc cccagggtcc   1380
ctaaccgtct tttccctggg cgagtcagcc caatcacagg actgagagtg cctctttagt   1440
agcagcaagc cacttcggac acccaaatgg aacacctcca gtcagccctc gccgaccacc   1500 ccacccctc catccttttc cctcagcctc cgattggctg aatctagagt ccctccctgc   1560
tcccccctct ctccccaccc ctggtgaaaa ctgcgggctt cagcgctggg tgcagcaact   1620
ggaggcgttg gcgcaccagg aggaggctgc agctagggga gtccaggtga gagcaggccg   1680
acgggaggga cccgcacatg caaggaccgc cgcagggcga ggatgcaagc cttccccagc   1740
tacagttttg ggaaaggata ccagggcgct cctatatggg ggcgcgggaa ctggggaaag   1800
aaggtgctcc caggtcgagg tgggagagga aggcagtgcg gggtcacggg ctttctccct   1860
gctaacggac gctttcgaag agtgggtgcc ggaggagaac catgaggaag gacatcaagg   1920
acagcctttg gtccccaagc tcaaatcgct ttagtggtgc gaatagaggg aggaggtggg   1980
tggcaaactg gagggagtcc ccagcgggtg acctcgtggc tggctgggtg cggggcaccg   2040
caggtaagaa aaccgcaatg ttgcgggagg ggactgggtg gcaggcgcgg gggaggggaa   2100
agctagaaag gatgcgaggg agcggagggg ggagggagcg ggagaatctc aactggtaga   2160
ggaagattaa aatgaggaaa tagcatcagg gtggggttag ccaagccggg cctcagggaa   2220
agggcgcaaa gtttgtctgg gtgtgggctt aggtgggctg ggtatgagat tcggggcgcc   2280
gaaaacactg ctgcgcctct gccaaatcac gctaccctg tatctagttc tgccaggctt   2340
ctccagcccc agccccaatt cttttctcta gtgttccccc ttccctcccc tgaatctcaa   2400
gcccacactc cctcctccat aacccactgt tatcaaatcc aagtcatttg ccacccaaca   2460
accatcagga ggcggaagca gacgggagga gtttgagatc aacttgggct acatcacgag   2520
ttccaggctc accaaggctt cttaaggaga ccttgtctct aaaattaatt aattaattaa   2580
ttaatagtcc cctttctctg ccacagaacc ttgggatctg gctcctggtc gcagctcccc   2640
ccaccccagg ctgacattca ctgccatagc ccatccggaa atcctagtct atttccccat   2700
ggatcttgaa ctgcagagag aatggcagag tggcccgccc tgtgcaaagg atgttcctag   2760
cctaggtgga gctcgcgaac tcgcagactg tgcctctctt gggcaaggac aggctagaca   2820
gcctgccggt gtgttgagct agggcactgt ggggaaggca gagaacctgt gcagggcagc   2880
aatgaacaca ggaccagaaa actgcagccc taggaacact caagagctgg ccatttgcaa   2940
gcatctctgg cctccgtgct tctcactcat gtcccatgtc ttatacaggc ctctgtggca   3000
cctcgcttgc ctgatctcat ccctagccgt taagctttct gcatgactta tcacttgggg   3060
cataatgctg ataccctacc attttcttag accccatcaa aatcctattt gagtgtacgg   3120
ttcggagaac ctcatttatc cggtaaatgt cttttactct gctctcaggg agctgaggca   3180
ggacatcctg agatacattg ggagaggaga tacagtttca ataaaataat aggttgggtg   3240
gaggtacatg cctataatgc caccactcag gaaatggtgg cagcttcgtg agtttgaggc   3300
```

```
caacccaaga acatagtga aaccctgtca gtaaataagt aagcaagtat ttgagtatct   3360
actatatgct agggctgacc tggacattag gggtcatctt ctgaacaaac tagtgcttga   3420
gggaggtatt tggggttttt gtttgtttaa tggatctgaa tgagttccag agactggcta   3480
cacagcgata tgactgagct taacacccct aaagcataca gtcagaccaa ttagacaata   3540
aaaggtatgt atagcttacc aaataaaaaa attgtatttt caagagagtg tctgtctgtg   3600
tagccctggc tgttcttgaa ctcactctgt agaccaggct ggcctggaaa tccatctgcc   3660
tgcctctgcc tctctgcctc tctgcctctc tgcctctctc tctgcctctc tctgcctctc   3720
tctgcccctc tctgcccctc tctgcccctc tctgcccctc tctgccgccc tctgccttct   3780
gccctctgcc ctctgcctc tggcctctgc cctctgccct ctggcctctg gcctctgcct   3840
ctgcctcttg agtgctggaa tcaaaggtgt gagctctgta ggtcttaagt tccagaagaa   3900
agtaatgaag tcacccagca gggaggtgct cagggacagc acagacacac acccaggaca   3960
taggctccca cttccttggc tttctctgag tggcaaagga ccttaggcag tgtcactccc   4020
taagagaagg ggataaagag aggggctgag gtattcatca tgtgctccgt ggatctcaag   4080
ccctcaaggt aaatggggac ccacctgtcc taccagctgg ctgacctgta gctttcccca   4140
ccacagaatc caagtcggaa ctcttggcac ctagaggatc tcgagatgca gggaccttgg   4200
ctgatgatgc ctctggcttt gatcttcgtg ctaactggta tccccaaatc ctgcgccttg   4260
ctggaagcag cccaggagga aggtgctgtg actcctgacc ttccaggcct ggagaaagtc   4320
caggtccggc cagaacgtcg attcttgagg aaagacctcc agcgtgtgcg aggggacctt   4380
ggtgctgcct tagattcctg gatcacaaaa cgccaattcc gacatgactc aggatatgaa   4440
gttcatcatc aaaaattggt gttctttgca gaagatgtgg gttcaaacaa aggtgcaatc   4500
attggactca tggtgggcgg tgttgtcata gcgtaactcg aggtccttcc tctgcagagg   4560
tcttgcttct cccggtcagc tgactccctc cccaagtcct tcaaatatct cagaacatgg   4620
ggagaaacgg ggaccttgtc cctcctaagg aaccccagtg ctgcatgcca tcatccccccc  4680
caccctcgcc cccacccccg ccacttctcc ctccatgcat accactagct gtcatttgt   4740
actctgtatt tattccaggg ctgcttctga ttatttagtt tgttctttcc ctggagacct   4800
gttagaacat aagggcgtat ggtgggtagg ggaggcagga tatcagtccc tggggcgagt   4860
tcctccctgc caaccaagcc agatgcctga agagatatg gatgagggaa gttggactgt   4920
gcctgtacct ggtacagtca tactctgttg aaagaatcat cggggagggg gggggggct   4980
caagatggga gagctctgct gagcctttgt ggaccatcca atgaggatga gggcttagat   5040
tctaccaggt cattctcagc caccacacac aagcgctctg ccatcactga agaagccccc   5100
tagggctctt gggccagggc acactcagta aagatgcagg ttcagtcagg gaatgatggg   5160
gaaaggggta ggaggtgggg gagggatcac ccccctcctct aaaacacgag cctgctgtct   5220
ccaaaggcct ctgcctgtag tgagggtggc agaagaagac aaggagccag aactctgact   5280
ccaggatcta agtccgtgca ggaaggggat cctagaacca tccggttgga cccagcttac   5340
caagggagag cctttattct tctttccctt gcccctctgt gccagcccct cttgctgtcc   5400
ctgatccccc agacagcgag agtcttgcaa cctgcctctt ccaagacctc ctaatctcag   5460
gggcaggcgg tggagtgaga tccggcgtgc acacttttg gaagatagct ttcccaagga   5520
tcctctcccc cactggcagc tctgcctgtc ccatcaccat gtataatacc accactgcta   5580
cagcatctca ccgaggaaag aaaactgcac aataaaacca agcctctgga gtgtgtcctg   5640
gtgtctgtct cttctgtgtc ctggcgtctg tctcttctgt gttcttccaa ggtcagaaac   5700
```

```
aaaaaccaca cacttcaacc tggatggctc ggctgagcac ttctgtgtgc agaaggtcca      5760
accagactct gggqtacccc ggccctccct attcccttgc ctcctgtctc ccgcttttta      5820
tagctcccta tgctgggctt ctctggagag tgaaatcttt gcccaaatca atgcgcattc      5880
tctctgctga gtcatctggc acagcagtt gagttcaccc gccaacacat gggcccagct       5940
atgtagccga accctggctc tggaagtgcc agggactttg tgcataagta tgtaccatgc      6000 cctttttca  cagtcctagc tctgcagaag tgcagcctga aggcctgtct gctgagagga      6060
catgccctgg agccctgaaa caggcacagt gggaggagga acggaggatg acaggcatca     6120
ggccctcagt ccaaaagcaa ccacttgaga atgggctgga gtacgaaaca tggggtcccg     6180
tccctggatc cctcctcaaa gagtaataag taaaatataa acaggtaccc caggccgttc     6240
tgggtttggg ttgtaatggg atccatttgc agagaactat tgagacagcc cagccgtact     6300
gtgacaggca atgtggggga ggaggttgaa tcacttggta tttagcatga atagaataat     6360
tccctgaaca ttttcttaa acatccatat ctaaattacc accactcgct cccagtcttc      6420
ctgcctttgc gccagcctcc tgtctggcca tgcctgaaga aggctggaga agccacccac     6480
ctcaggccat gacactgcca gccacttggc aggtgcagcc aaacctgagc tgtcccagaa     6540
agggacattc tcaagaccca ggcaccctga tcagcactga cttggagcta caagtgtcat     6600
gccagaaaag tctctaagaa aacctttca gggaaaaggg ggtgactcaa cacccgggcaa     6660 gtttgggaag ccccacccctt cgagtgatgg aagagcagat aggaagcctc agaagagaga    6720
caccggcacc caggtaacgt tcctcatgtg gtctctgtca cactaggtgc tcttccctgg     6780
acatctccgt gaccacactc tcagttctta gggagatgcg ggtgctctct gaggctatct     6840
cagagttgca gattctgagg cctagagtga ctacagtcag cctaggaagc cacagaggac     6900
tgtggaccag gagggcagaa gaggagaagg gaagaaaaac catcagatag gacttgcaat     6960
gaaactaacc caagacaatc ataatgcaga caggaatgtt aaaggcgttc agcagctggc     7020
catgacaccc atctgtccct ctggccaagt cagcaagcct ggaagacctg ggactcctgc     7080
ccatatgtcc taagctccca cccacccact cgttcactgt ccttattctc tctctacctt     7140
cagccactta gtttcctacc ttaagtccta gaattc                               7176

<210> SEQ ID NO 8
<211> LENGTH: 363
<212> TYPE: DNA
<213> ORGANISM: Artificial Sequence
<220> FEATURE:
<223> OTHER INFORMATION: synthetic nucleotide

<400> SEQUENCE: 8
ctcgagatgc agggaccttg gctgatgatg gctctggctt tgatcttcgt gctaactggt       60
atccccaaat cctgcgcctt gctggaagca gcccaggagg aagtgctgt gactcctgac       120 cttccaggcc tggagaaagt ccaggtccgg ccagaacgtc gattcttgag gaaagacctc      180
cagcgtgtgc gagggacct tggtgctgcc ttagattcct ggatcacaaa acgccaattc       240
cgacatgact caggatatga agttcatcat caaaaattgg tgttctttgc agaagatgtg      300
ggttcaaaca aaggtgcaat cattggactc atggtgggcg tgttgtcat agcgtaactc      360 gag                                                                    363

<210> SEQ ID NO 9
<211> LENGTH: 120
<212> TYPE: DNA
<213> ORGANISM: Artificial sequence
```

<220> FEATURE:
<223> OTHER INFORMATION: Synthetic peptide

<400> SEQUENCE: 9
gagttccgac atgactcagg atatgaagtt catcatcaaa aattggtgtt ctttgcagaa    60
gatgtgggtt caaacaaagg tgcaatcatt ggactcatgg tgggcggtgt tgtcatagcg   120

<210> SEQ ID NO 10
<211> LENGTH: 120
<212> TYPE: DNA
<213> ORGANISM: Artificial sequence
<220> FEATURE:
<223> OTHER INFORMATION: Synthetic nucloetide

<400> SEQUENCE: 10
caattccgac atgactcagg atatgaagtt catcatcaaa aattggtgtt ctttgcagaa    60
gatgtgggtt caaacaaagg tgcaatcatt ggactcatgg tgggcggtgt tgtcatagcg   120

<210> SEQ ID NO 11
<211> LENGTH: 114
<212> TYPE: DNA
<213> ORGANISM: Artificial sequence
<220> FEATURE:
<223> OTHER INFORMATION: Synthetic nucleotide

<400> SEQUENCE: 11
gagttccgac atgactcagg atatgaagtt catcatcaaa aattggtgtt ctttgcagaa    60
gatgtgggtt caaacaaagg tgcaatcatt ggactcatgg tgggcggtgt tgtc         114

<210> SEQ ID NO 12
<211> LENGTH: 114
<212> TYPE: DNA
<213> ORGANISM: Artificial sequence
<220> FEATURE:
<223> OTHER INFORMATION: Synthetic nucloetide

<400> SEQUENCE: 12
caattccgac atgactcagg atatgaagtt catcatcaaa aattggtgtt ctttgcagaa    60
gatgtgggtt caaacaaagg tgcaatcatt ggactcatgg tgggcggtgt tgtc         114

<210> SEQ ID NO 13
<211> LENGTH: 361
<212> TYPE: PRT
<213> ORGANISM: human

<400> SEQUENCE: 13

Met Ala Gly Gly Arg His Arg Val Val Gly Thr Leu His Leu Leu
1               5                   10                  15

Leu Leu Val Ala Ala Leu Pro Trp Ala Ser Arg Gly Val Ser Pro Ser
                20                  25                  30

Ala Ser Ala Trp Pro Glu Glu Lys Asn Tyr His Gln Pro Ala Ile Leu
            35                  40                  45

Asn Ser Ser Ala Leu Arg Gln Ile Ala Glu Gly Thr Ser Ile Ser Glu
        50                  55                  60

Met Trp Gln Asn Asp Leu Gln Pro Leu Leu Ile Glu Arg Tyr Pro Gly
65                  70                  75                  80

Ser Pro Gly Ser Tyr Ala Ala Arg Gln His Ile Met Gln Arg Ile Gln
                85                  90                  95

Arg Leu Gln Ala Asp Trp Val Leu Glu Ile Asp Thr Phe Leu Ser Gln
                100                 105                 110

```
Thr Pro Tyr Gly Tyr Arg Ser Phe Ser Asn Ile Ile Ser Thr Leu Asn
        115                 120                 125

Pro Thr Ala Lys Arg His Leu Val Leu Ala Cys His Tyr Asp Ser Lys
130                 135                 140

Tyr Phe Ser His Trp Asn Asn Arg Val Phe Val Gly Ala Thr Asp Ser
145                 150                 155                 160

Ala Val Pro Cys Ala Met Met Leu Glu Leu Ala Arg Ala Leu Asp Lys
                165                 170                 175

Lys Leu Leu Ser Leu Lys Thr Val Ser Asp Ser Lys Pro Asp Leu Ser
                180                 185                 190

Leu Gln Leu Ile Phe Phe Asp Gly Glu Glu Ala Phe Leu His Trp Ser
            195                 200                 205

Pro Gln Asp Ser Leu Tyr Gly Ser Arg His Leu Ala Ala Lys Met Ala
        210                 215                 220

Ser Thr Pro His Pro Pro Gly Ala Arg Gly Thr Ser Gln Leu His Gly
225                 230                 235                 240

Met Asp Leu Leu Val Leu Leu Asp Leu Ile Gly Ala Pro Asn Pro Thr
                245                 250                 255

Phe Pro Asn Phe Phe Pro Asn Ser Ala Arg Trp Phe Gly Arg Leu Gln
                260                 265                 270

Ala Ile Glu His Glu Leu His Glu Leu Gly Leu Leu Lys Asp His Ser
            275                 280                 285

Leu Glu Gly Arg Tyr Phe Gln Asn Tyr Ser Tyr Gly Gly Val Ile Gln
        290                 295                 300

Asp Asp His Ile Pro Phe Leu Arg Arg Gly Val Pro Val Leu His Leu
305                 310                 315                 320

Ile Pro Ser Pro Phe Pro Glu Val Trp His Thr Met Asp Asp Asn Glu
                325                 330                 335

Glu Asn Leu Asp Glu Ser Thr Ile Asp Asn Leu Asn Lys Ile Leu Gln
                340                 345                 350

Val Phe Val Leu Glu Tyr Leu His Leu
                355                 360

<210> SEQ ID NO 14
<211> LENGTH: 382
<212> TYPE: PRT
<213> ORGANISM: human

<400> SEQUENCE: 14

Met Arg Ser Gly Gly Arg Gly Arg Pro Arg Leu Arg Leu Gly Glu Arg
1               5                   10                  15

Gly Leu Met Glu Pro Leu Leu Pro Pro Lys Arg Arg Leu Leu Pro Arg
                20                  25                  30

Val Arg Leu Leu Pro Leu Leu Leu Ala Leu Ala Val Gly Ser Ala Phe
            35                  40                  45

Tyr Thr Ile Trp Ser Gly Trp His Arg Arg Thr Glu Glu Leu Pro Leu
        50                  55                  60

Gly Arg Glu Leu Arg Val Pro Leu Ile Gly Ser Leu Pro Glu Ala Arg
65                  70                  75                  80

Leu Arg Arg Val Val Gly Gln Leu Asp Pro Gln Arg Leu Trp Ser Thr
                85                  90                  95

Tyr Leu Arg Pro Leu Leu Val Val Arg Thr Pro Gly Ser Pro Gly Asn
                100                 105                 110

Leu Gln Val Arg Lys Phe Leu Glu Ala Thr Leu Arg Ser Leu Thr Ala
            115                 120                 125
```

Gly Trp His Val Glu Leu Asp Pro Phe Thr Ala Ser Thr Pro Leu Gly
            130                 135                 140

Pro Val Asp Phe Gly Asn Val Val Ala Thr Leu Asp Pro Arg Ala Ala
145                 150                 155                 160

Arg His Leu Thr Leu Ala Cys His Tyr Asp Ser Lys Leu Phe Pro Pro
                165                 170                 175

Gly Ser Thr Pro Phe Val Gly Ala Thr Asp Ser Ala Val Pro Cys Ala
            180                 185                 190

Leu Leu Leu Glu Leu Ala Gln Ala Leu Asp Leu Glu Leu Ser Arg Ala
        195                 200                 205

Lys Lys Gln Ala Ala Pro Val Thr Leu Gln Leu Phe Leu Asp Gly
    210                 215                 220

Glu Glu Ala Leu Lys Glu Trp Gly Pro Lys Asp Ser Leu Tyr Gly Ser
225                 230                 235                 240

Arg His Leu Ala Gln Leu Met Glu Ser Ile Pro His Ser Pro Gly Pro
                245                 250                 255

Thr Arg Ile Gln Ala Ile Glu Leu Phe Met Leu Leu Asp Leu Leu Gly
            260                 265                 270

Ala Pro Asn Pro Thr Phe Tyr Ser His Phe Pro Arg Thr Val Arg Trp
        275                 280                 285

Phe His Arg Leu Arg Ser Ile Glu Lys Arg Leu His Arg Leu Asn Leu
    290                 295                 300

Leu Gln Ser His Pro Gln Glu Val Met Tyr Phe Gln Pro Gly Glu Pro
305                 310                 315                 320

Phe Gly Ser Val Glu Asp Asp His Ile Pro Leu Arg Arg Gly Val
                325                 330                 335

Pro Val Leu His Leu Ile Ser Thr Pro Phe Pro Ala Val Trp His Thr
            340                 345                 350

Pro Ala Asp Thr Glu Val Asn Leu His Pro Pro Thr Val His Asn Leu
        355                 360                 365

Cys Arg Ile Leu Ala Val Phe Leu Ala Glu Tyr Leu Gly Leu
    370                 375                 380

<210> SEQ ID NO 15
<211> LENGTH: 364
<212> TYPE: PRT
<213> ORGANISM: human

<400> SEQUENCE: 15

Met Glu Pro Leu Leu Pro Pro Lys Arg Arg Leu Leu Pro Arg Val Arg
1               5                   10                  15

Leu Leu Pro Leu Leu Leu Ala Leu Ala Val Gly Ser Ala Phe Tyr Thr
            20                  25                  30

Ile Trp Ser Gly Trp His Arg Arg Thr Glu Glu Leu Pro Leu Gly Arg
        35                  40                  45

Glu Leu Arg Val Pro Leu Ile Gly Ser Leu Pro Glu Ala Arg Leu Arg
    50                  55                  60

Arg Val Val Gly Gln Leu Asp Pro Gln Arg Leu Trp Ser Thr Tyr Leu
65                  70                  75                  80

Arg Pro Leu Leu Val Val Arg Thr Pro Gly Ser Pro Gly Asn Leu Gln
                85                  90                  95

Val Arg Lys Phe Leu Glu Ala Thr Leu Arg Ser Leu Thr Ala Gly Trp
            100                 105                 110

His Val Glu Leu Asp Pro Phe Thr Ala Ser Thr Pro Leu Gly Pro Val
        115                 120                 125

```
Asp Phe Gly Asn Val Val Ala Thr Leu Asp Pro Arg Ala Ala Arg His
            130                 135                 140

Leu Thr Leu Ala Cys His Tyr Asp Ser Lys Leu Phe Pro Pro Gly Ser
145                 150                 155                 160

Thr Pro Phe Val Gly Ala Thr Asp Ser Ala Val Pro Cys Ala Leu Leu
                165                 170                 175

Leu Glu Leu Ala Gln Ala Leu Asp Leu Glu Leu Ser Arg Ala Lys Lys
            180                 185                 190

Gln Ala Ala Pro Val Thr Leu Gln Leu Leu Phe Leu Asp Gly Glu Glu
        195                 200                 205

Ala Leu Lys Glu Trp Gly Pro Lys Asp Ser Leu Tyr Gly Ser Arg His
    210                 215                 220

Leu Ala Gln Leu Met Glu Ser Ile Pro His Ser Pro Gly Pro Thr Arg
225                 230                 235                 240

Ile Gln Ala Ile Glu Leu Phe Met Leu Leu Asp Leu Leu Gly Ala Pro
                245                 250                 255

Asn Pro Thr Phe Tyr Ser His Phe Pro Arg Thr Val Arg Trp Phe His
            260                 265                 270

Arg Leu Arg Ser Ile Glu Lys Arg Leu His Arg Leu Asn Leu Leu Gln
        275                 280                 285

Ser His Pro Gln Glu Val Met Tyr Phe Gln Pro Gly Glu Pro Phe Gly
    290                 295                 300

Ser Val Glu Asp Asp His Ile Pro Phe Leu Arg Arg Gly Val Pro Val
305                 310                 315                 320

Leu His Leu Ile Ser Thr Pro Phe Pro Ala Val Trp His Thr Pro Ala
                325                 330                 335

Asp Thr Glu Val Asn Leu His Pro Pro Thr Val His Asn Leu Cys Arg
            340                 345                 350

Ile Leu Ala Val Phe Leu Ala Glu Tyr Leu Gly Leu
        355                 360

<210> SEQ ID NO 16
<211> LENGTH: 382
<212> TYPE: PRT
<213> ORGANISM: Macaca fascicularis

<400> SEQUENCE: 16

Met Arg Ser Gly Gly Arg Gly Arg Pro Arg Leu Arg Leu Gly Glu Arg
1               5                   10                  15

Gly Val Met Glu Pro Leu Leu Pro Pro Lys Arg Arg Leu Leu Pro Arg
            20                  25                  30

Val Arg Leu Leu Pro Leu Leu Leu Ala Leu Ala Val Gly Ser Ala Phe
        35                  40                  45

Tyr Thr Ile Trp Ser Gly Trp His Arg Arg Thr Glu Glu Leu Pro Leu
    50                  55                  60

Gly Arg Glu Leu Arg Val Pro Leu Ile Gly Ser Leu Pro Glu Ala Arg
65                  70                  75                  80

Leu Arg Arg Val Val Gly Gln Leu Asp Pro Gln Arg Leu Trp Gly Thr
                85                  90                  95

Tyr Leu Arg Pro Leu Leu Val Val Arg Thr Pro Gly Ser Pro Gly Asn
            100                 105                 110

Leu Gln Val Arg Lys Phe Leu Glu Ala Thr Leu Arg Ser Leu Thr Ala
        115                 120                 125

Gly Trp His Val Glu Leu Asp Pro Phe Thr Ala Ser Thr Pro Leu Gly
    130                 135                 140
```

```
Pro Val Asp Phe Gly Asn Val Val Ala Thr Leu Asp Pro Gly Ala Ala
145                 150                 155                 160

Arg His Leu Thr Leu Ala Cys His Tyr Asp Ser Lys Leu Phe Pro Pro
            165                 170                 175

Gly Ser Thr Pro Phe Val Gly Ala Thr Asp Ser Ala Val Pro Cys Ala
            180                 185                 190

Leu Leu Leu Glu Leu Ala Gln Ala Leu Asp Leu Glu Leu Ser Arg Ala
            195                 200                 205

Lys Glu Gln Ala Ala Pro Val Thr Leu Gln Leu Leu Phe Leu Asp Gly
            210                 215                 220

Glu Glu Ala Leu Lys Glu Trp Gly Pro Lys Asp Ser Leu Tyr Gly Ser
225                 230                 235                 240

Arg His Leu Ala Gln Leu Met Glu Ser Ile Pro His Ser Pro Gly Pro
            245                 250                 255

Thr Arg Ile Gln Ala Ile Glu Leu Phe Met Leu Leu Asp Leu Leu Gly
            260                 265                 270

Ala Pro Asn Pro Thr Phe Tyr Ser His Phe Pro Arg Thr Val Arg Trp
            275                 280                 285

Phe His Arg Leu Arg Ser Ile Glu Lys Arg Leu His Arg Leu Asn Leu
            290                 295                 300

Leu Gln Ser His Pro Gln Glu Val Met Tyr Phe Gln Pro Gly Glu Pro
305                 310                 315                 320

Phe Gly Ser Val Glu Asp Asp His Ile Pro Phe Leu Arg Arg Gly Val
            325                 330                 335

Pro Val Leu His Leu Ile Ser Thr Pro Phe Pro Ala Val Trp His Thr
            340                 345                 350

Pro Ala Asp Thr Glu Ala Asn Leu His Pro Pro Thr Val His Asn Leu
            355                 360                 365

Ser Arg Ile Leu Ala Val Phe Leu Ala Glu Tyr Leu Gly Leu
            370                 375                 380

<210> SEQ ID NO 17
<211> LENGTH: 382
<212> TYPE: PRT
<213> ORGANISM: Macaca mulatta

<400> SEQUENCE: 17

Met Arg Ser Gly Gly Arg Gly Arg Pro Arg Leu Arg Leu Gly Glu Arg
1               5                   10                  15

Gly Val Met Glu Pro Leu Leu Pro Pro Lys Arg Arg Leu Leu Pro Arg
            20                  25                  30

Val Arg Leu Leu Pro Leu Leu Leu Ala Leu Ala Val Gly Ser Ala Phe
            35                  40                  45

Tyr Thr Ile Trp Ser Gly Trp His Arg Arg Thr Glu Glu Leu Pro Leu
50                  55                  60

Gly Arg Glu Leu Arg Val Pro Leu Ile Gly Ser Leu Pro Glu Ala Arg
65                  70                  75                  80

Leu Arg Arg Val Val Gly Gln Leu Asp Pro Gln Arg Leu Trp Gly Thr
            85                  90                  95

Tyr Leu Arg Pro Leu Leu Val Val Arg Thr Pro Gly Ser Pro Gly Asn
            100                 105                 110

Leu Gln Val Arg Lys Phe Leu Glu Ala Thr Leu Arg Ser Leu Thr Ala
            115                 120                 125

Gly Trp His Val Glu Leu Asp Pro Phe Thr Ala Ser Thr Pro Leu Gly
            130                 135                 140
```

```
Pro Val Asp Phe Gly Asn Val Val Ala Thr Leu Asp Pro Gly Ala Ala
145                 150                 155                 160

Arg His Leu Thr Leu Ala Cys His Tyr Asp Ser Lys Leu Phe Pro Pro
                165                 170                 175

Gly Ser Thr Pro Phe Val Gly Ala Thr Asp Ser Ala Val Pro Cys Ala
            180                 185                 190

Leu Leu Leu Glu Leu Ala Gln Ala Leu Asp Leu Glu Leu Ser Arg Ala
        195                 200                 205

Lys Glu Gln Ala Ala Pro Val Thr Leu Gln Leu Leu Phe Leu Asp Gly
210                 215                 220

Glu Glu Ala Leu Lys Glu Trp Gly Pro Lys Asp Ser Leu Tyr Gly Ser
225                 230                 235                 240

Arg His Leu Ala Gln Leu Met Glu Ser Ile Pro His Ser Pro Gly Pro
                245                 250                 255

Thr Arg Ile Gln Ala Ile Glu Leu Phe Met Leu Leu Asp Leu Leu Gly
            260                 265                 270

Ala Pro Asn Pro Thr Phe Tyr Ser His Phe Pro Arg Thr Val Arg Trp
        275                 280                 285

Phe His Arg Leu Arg Ser Ile Glu Lys Arg Leu His Arg Leu Asn Leu
290                 295                 300

Leu Gln Ser His Pro Gln Glu Val Met Tyr Phe Gln Pro Gly Glu Pro
305                 310                 315                 320

Phe Gly Ser Val Glu Asp Asp His Ile Pro Phe Leu Arg Arg Gly Val
                325                 330                 335

Pro Val Leu His Leu Ile Ser Thr Pro Phe Pro Ala Val Trp His Thr
            340                 345                 350

Pro Ala Asp Thr Glu Ala Asn Leu His Pro Pro Thr Val His Asn Leu
        355                 360                 365

Ser Arg Ile Leu Ala Val Phe Leu Ala Glu Tyr Leu Gly Leu
370                 375                 380

<210> SEQ ID NO 18
<211> LENGTH: 383
<212> TYPE: PRT
<213> ORGANISM: Canis familiaris

<400> SEQUENCE: 18

Met Pro Ser Gly Gly Arg Gly Arg Ser Arg Leu Arg Leu Gly Glu Arg
1               5                   10                  15

Gly Leu Leu Glu Pro Pro Ser Pro Pro Lys Arg Arg Leu Leu Pro Arg
            20                  25                  30

Ala His Phe Leu Pro Leu Leu Leu Ala Leu Ala Leu Ala Ser Ala
        35                  40                  45

Thr Tyr Thr Ile Trp Ser Gly Trp His His Gln Thr Glu Glu Leu Pro
50                  55                  60

Arg Gly Arg Glu Leu Arg Gly Arg Leu Ile Gly Ser Leu Ser Glu Ala
65                  70                  75                  80

Arg Leu Arg Arg Val Val Gly Gln Leu Asp Pro His Arg Leu Trp Asn
                85                  90                  95

Thr Tyr Leu Arg Pro Leu Leu Val Val Arg Thr Pro Gly Ser Pro Gly
            100                 105                 110

Asn Leu Gln Val Arg Lys Phe Leu Glu Ala Thr Leu Arg Thr Leu Thr
        115                 120                 125

Ala Gly Trp His Val Glu Leu Asp Pro Phe Thr Ala Leu Thr Pro Leu
130                 135                 140
```

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Leu Phe Ala
                165                 170                 175

Ser Glu Ser Val Pro Phe Val Gly Ala Thr Asp Ser Ala Val Pro Cys
            180                 185                 190

Ala Leu Leu Leu Glu Leu Ala Gln Ala Leu Asp Arg Glu Leu Ser Arg
        195                 200                 205

Ala Lys Glu Gln Glu Ala Pro Val Thr Leu Gln Leu Leu Phe Leu Asp
    210                 215                 220

Gly Glu Glu Ala Leu Lys Glu Trp Gly Pro Thr Asp Ser Leu Tyr Gly
225                 230                 235                 240

Ser Arg His Leu Ala Gln Leu Met Glu Ser Ala Pro His Ser Pro Gly
                245                 250                 255

Pro Thr Arg Ile Gln Ala Ile Glu Leu Phe Met Leu Leu Asp Leu Leu
            260                 265                 270

Gly Ala Pro Asn Pro Asn Phe Tyr Ser His Phe Pro His Thr Ala Arg
        275                 280                 285

Trp Phe His Arg Leu Arg Ser Ile Glu Lys Arg Leu His Arg Met Asn
    290                 295                 300

Leu Leu Gln Ser His Pro Gln Glu Val Met Tyr Phe Gln Pro Gly Glu
305                 310                 315                 320

Pro Pro Gly Ser Val Glu Asp Asp His Ile Pro Phe Leu Arg Arg Gly
                325                 330                 335

Val Pro Val Leu His Leu Ile Ser Met Pro Phe Pro Ser Val Trp His
            340                 345                 350

Thr Pro Asp Asp Ser Glu Ala Asn Leu His Pro Pro Thr Val His Asn
        355                 360                 365

Leu Ser Arg Ile Leu Ala Val Phe Leu Ala Glu Tyr Leu Gly Leu
    370                 375                 380

<210> SEQ ID NO 19
<211> LENGTH: 383
<212> TYPE: PRT
<213> ORGANISM: Rattus norvegicus

<400> SEQUENCE: 19

Met Ser Pro Ala Ser Arg Gly Arg Ser Arg Gln Arg Leu Gly Asp Arg
1               5                   10                  15

Gly Leu Met Lys Pro Pro Ser Leu Ser Lys Arg Arg Leu Leu Pro Arg
            20                  25                  30

Val Gln Leu Leu Pro Leu Leu Leu Ala Leu Ala Leu Gly Leu Ala
        35                  40                  45

Phe Tyr Ile Val Trp Asn Ser Trp His Pro Gly Val Glu Glu Val Ser
 50                 55                  60

Arg Ser Arg Asp Leu Arg Val Pro Leu Ile Gly Ser Leu Ser Glu Ala
65                  70                  75                  80

Lys Leu Arg Leu Val Val Gly Gln Leu Asp Pro Gln Arg Leu Trp Gly
                85                  90                  95

Thr Phe Leu Arg Pro Leu Leu Ile Val Arg Pro Pro Gly Ser Pro Gly
            100                 105                 110

Asn Leu Gln Val Arg Lys Phe Leu Glu Ala Thr Leu Gln Ser Leu Ser
        115                 120                 125

Ala Gly Trp His Val Glu Leu Asp Pro Phe Thr Ala Ser Thr Pro Leu
    130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Phe Phe Pro
            165                 170                 175

Pro Gly Leu Pro Pro Phe Val Gly Ala Thr Asp Ser Ala Val Pro Cys
        180                 185                 190

Ala Leu Leu Leu Glu Leu Val Gln Ala Leu Asp Val Met Leu Ser Arg
    195                 200                 205

Ile Lys Gln Gln Ala Ala Pro Val Thr Leu Gln Leu Leu Phe Leu Asp
210                 215                 220

Gly Glu Glu Ala Leu Lys Glu Trp Gly Pro Lys Asp Ser Leu Tyr Gly
225                 230                 235                 240

Ser Arg His Leu Ala Gln Ile Met Glu Ser Ile Pro His Ser Pro Gly
            245                 250                 255

Pro Thr Arg Ile Gln Ala Ile Glu Leu Phe Val Leu Leu Asp Leu Leu
        260                 265                 270

Gly Ala Pro Ser Pro Ile Phe Phe Ser His Phe Pro Arg Thr Ala Arg
    275                 280                 285

Trp Phe Gln Arg Leu Arg Ser Ile Glu Lys Arg Leu His Arg Leu Asn
290                 295                 300

Leu Leu Gln Ser His Pro Gln Glu Val Met Tyr Phe Gln Pro Gly Glu
305                 310                 315                 320

Pro Pro Gly Pro Val Glu Asp Asp His Ile Pro Phe Leu Arg Arg Gly
            325                 330                 335

Val Pro Val Leu His Leu Ile Ala Met Pro Phe Pro Ala Val Trp His
        340                 345                 350

Thr Pro Ala Asp Thr Glu Ala Asn Leu His Pro Thr Val His Asn
    355                 360                 365

Leu Ser Arg Ile Leu Ala Val Phe Leu Ala Glu Tyr Leu Gly Leu
370                 375                 380

<210> SEQ ID NO 20
<211> LENGTH: 383
<212> TYPE: PRT
<213> ORGANISM: Mus musculus

<400> SEQUENCE: 20

Met Ser Pro Gly Ser Arg Gly Arg Pro Arg Gln Arg Leu Glu Asp Arg
1               5                   10                  15

Gly Leu Met Thr Lys Pro Pro Ser Leu Ser Lys Arg Arg Leu Leu Pro Arg
            20                  25                  30

Val Gln Phe Leu Pro Leu Leu Leu Ala Leu Ala Met Gly Leu Ala
        35                  40                  45

Phe Tyr Ile Val Trp Asn Ser Trp His Pro Gly Val Glu Glu Met Ser
50                  55                  60

Arg Ser Arg Asp Leu Arg Val Pro Leu Ile Gly Ser Leu Ser Glu Ala
65                  70                  75                  80

Lys Leu Arg Leu Val Val Gly Gln Leu Asp Pro Gln Arg Leu Trp Gly
            85                  90                  95

Thr Phe Leu Arg Pro Leu Leu Ile Val Arg Pro Pro Gly Ser Ser Gly
        100                 105                 110

Asn Leu Gln Val Arg Lys Phe Leu Glu Ala Thr Leu Gln Ser Leu Ser
    115                 120                 125

Ala Gly Trp His Val Glu Leu Asp Pro Phe Thr Ala Ser Thr Pro Leu
130                 135                 140

```
Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Phe Phe Pro
            165                 170                 175

Pro Gly Leu Pro Pro Phe Val Gly Ala Thr Asp Ser Ala Val Pro Cys
        180                 185                 190

Ala Leu Leu Leu Glu Leu Val Gln Ala Leu Asp Ala Met Leu Ser Arg
    195                 200                 205

Ile Lys Gln Gln Ala Ala Pro Val Thr Leu Gln Leu Leu Phe Leu Asp
210                 215                 220

Gly Glu Glu Ala Leu Lys Glu Trp Gly Pro Lys Asp Ser Leu Tyr Gly
225                 230                 235                 240

Ser Arg His Leu Ala Gln Ile Met Glu Ser Ile Pro His Ser Pro Gly
                245                 250                 255

Pro Thr Arg Ile Gln Ala Ile Glu Leu Phe Val Leu Leu Asp Leu Leu
            260                 265                 270

Gly Ala Ser Ser Pro Ile Phe Phe Ser His Phe Pro Arg Thr Ala Arg
                275                 280                 285

Trp Phe Gln Arg Leu Arg Ser Ile Glu Lys Arg Leu His Arg Leu Asn
290                 295                 300

Leu Leu Gln Ser His Pro Gln Glu Val Met Tyr Phe Gln Pro Gly Glu
305                 310                 315                 320

Pro Pro Gly Pro Val Glu Asp Asp His Ile Pro Phe Leu Arg Arg Gly
                325                 330                 335

Val Pro Val Leu His Leu Ile Ala Thr Pro Phe Pro Ala Val Trp His
            340                 345                 350

Thr Pro Ala Asp Thr Glu Ala Asn Leu His Pro Pro Thr Val His Asn
        355                 360                 365

Leu Ser Arg Ile Leu Ala Val Phe Leu Ala Glu Tyr Leu Gly Leu
        370                 375                 380

<210> SEQ ID NO 21
<211> LENGTH: 383
<212> TYPE: PRT
<213> ORGANISM: Bos taurus

<400> SEQUENCE: 21

Met Pro Ser Gly Gly Arg Gly Arg Pro Arg Leu Gln Val Gly Glu Arg
1               5                   10                  15

Ser Leu Leu Glu Arg Pro Ser Pro Pro Lys Arg Arg Leu Ile Pro Arg
            20                  25                  30

Ala Gln Leu Leu Pro Gln Leu Leu Ala Leu Thr Val Ala Ser Val
        35                  40                  45

Phe Tyr Thr Ile Trp Arg Ile Trp His Ser Gln Thr Glu Glu Leu Pro
50                  55                  60

Leu Gly Arg Glu Leu Arg Gly Pro Leu Ile Gly Ser Leu Pro Glu Ala
65                  70                  75                  80

Arg Val Arg Arg Val Val Gly Gln Leu Asp Pro His Arg Leu Trp Asn
                85                  90                  95

Thr Phe Leu Arg Pro Leu Leu Val Val Arg Thr Pro Gly Ser Pro Gly
            100                 105                 110

Asn Leu Gln Val Arg Lys Phe Leu Glu Ala Thr Leu Arg Thr Leu Ser
        115                 120                 125

Ala Gly Trp His Ile Glu Leu Asp Ser Phe Thr Ala Ser Thr Pro Val
    130                 135                 140
```

Gly Pro Leu Asp Phe Ser Asn Val Val Ala Thr Leu Asp Pro Gly Ala
145                 150                 155                 160

Ala Arg His Leu Thr Leu Ala Cys His Tyr Asp Ser Lys Leu Phe Pro
            165                 170                 175

Ser Asp Ser Ala Pro Phe Val Gly Ala Thr Asp Ser Ala Val Pro Cys
            180                 185                 190

Ser Leu Leu Leu Glu Leu Ala Gln Ala Leu Asp Gln Glu Leu Gly Lys
            195                 200                 205

Ala Lys Glu Arg Ala Ala Pro Met Thr Leu Gln Leu Ile Phe Leu Asp
210                 215                 220

Gly Glu Glu Ala Leu Lys Gln Trp Gly Pro Lys Asp Ser Leu Tyr Gly
225                 230                 235                 240

Ser Arg His Leu Ala Gln Leu Met Glu Ser Thr Pro His Gly Leu Gly
            245                 250                 255

Ser Thr Arg Ile Gln Ala Ile Glu Leu Phe Met Leu Leu Asp Leu Leu
            260                 265                 270

Gly Ala Pro Asn Pro Thr Phe Tyr Ser His Phe Pro Arg Thr Ala Arg
            275                 280                 285

Trp Phe His Arg Leu Arg Ser Ile Glu Lys Arg Leu His Arg Leu Asn
290                 295                 300

Leu Leu Gln Ser His Pro Trp Glu Val Met Tyr Phe Gln Thr Gly Glu
305                 310                 315                 320

Pro Pro Gly Ser Val Glu Asp Asp His Ile Pro Phe Leu Arg Gly
            325                 330                 335

Val Pro Val Leu His Leu Ile Ala Thr Pro Phe Pro Ser Val Trp His
            340                 345                 350

Thr Ser Asp Asp Ser Glu Ala Asn Leu His Pro Pro Thr Val His Asn
            355                 360                 365

Leu Ser Arg Ile Leu Ala Val Phe Leu Ala Glu Tyr Leu Gly Leu
            370                 375                 380

<210> SEQ ID NO 22
<211> LENGTH: 481
<212> TYPE: PRT
<213> ORGANISM: human

<400> SEQUENCE: 22

Val Trp Tyr Arg Phe Gln Gly Lys Ala Ala Met Arg Ser Gly Gly Arg
1               5                   10                  15

Gly Arg Pro Arg Leu Arg Leu Gly Glu Arg Gly Leu Met Glu Pro Leu
            20                  25                  30

Leu Pro Pro Lys Arg Arg Leu Leu Pro Arg Val Arg Leu Leu Pro Leu
            35                  40                  45

Leu Leu Ala Leu Ala Val Gly Ser Ala Phe Tyr Thr Ile Trp Ser Gly
50                  55                  60

Trp His Arg Arg Thr Glu Glu Leu Pro Leu Gly Arg Glu Leu Arg Val
65                  70                  75                  80

Pro Leu Ile Gly Ser Leu Pro Glu Ala Arg Leu Arg Arg Val Val Gly
            85                  90                  95

Gln Leu Asp Pro Gln Arg Leu Trp Ser Thr Tyr Leu Arg Pro Leu Leu
            100                 105                 110

Val Val Arg Thr Pro Gly Ser Pro Gly Asn Leu Gln Val Arg Lys Phe
            115                 120                 125

Leu Glu Ala Thr Leu Arg Ser Leu Thr Ala Gly Trp His Val Glu Leu
            130                 135                 140

```
Asp Pro Phe Thr Ala Ser Thr Pro Leu Gly Pro Val Asp Phe Gly Asn
145                 150                 155                 160

Val Val Ala Thr Leu Asp Pro Arg Ala Arg His Leu Thr Leu Ala
                165                 170                 175

Cys His Tyr Asp Ser Lys Leu Phe Pro Pro Gly Ser Thr Pro Phe Val
                180                 185                 190

Gly Ala Thr Asp Ser Ala Val Pro Cys Ala Leu Leu Glu Leu Ala
            195                 200                 205

Gln Ala Leu Asp Leu Glu Leu Ser Arg Ala Lys Lys Gln Ala Ala Pro
            210                 215                 220

Val Thr Leu Gln Leu Leu Phe Leu Asp Gly Glu Ala Leu Lys Glu
225                 230                 235                 240

Trp Gly Pro Lys Asp Ser Leu Tyr Gly Ser Arg His Leu Ala Gln Leu
                245                 250                 255

Met Glu Ser Ile Pro His Ser Pro Gly Pro Thr Arg Ile Gln Ala Ile
            260                 265                 270

Glu Leu Phe Met Leu Leu Asp Leu Gly Ala Pro Asn Pro Thr Phe
            275                 280                 285

Tyr Ser His Phe Pro Arg Thr Val Arg Trp Phe His Arg Leu Arg Ser
290                 295                 300

Ile Glu Lys Arg Leu His Arg Leu Asn Leu Leu Gln Ser His Pro Gln
305                 310                 315                 320

Glu Val Met Tyr Phe Gln Pro Gly Glu Pro Phe Gly Ser Val Glu Asp
                325                 330                 335

Asp His Ile Pro Phe Leu Arg Arg Gly Val Pro Val Leu His Leu Ile
            340                 345                 350

Ser Thr Pro Phe Pro Ala Val Trp His Thr Pro Ala Asp Thr Glu Val
            355                 360                 365

Asn Leu His Pro Pro Thr Val His Asn Leu Cys Arg Ile Leu Ala Val
            370                 375                 380

Phe Leu Ala Glu Tyr Leu Gly Leu Arg Ala Trp Pro Met Thr Val Glu
385                 390                 395                 400

Arg Thr Val Arg Glu Lys Val Pro Ala Gly Ala Ser Glu Ala Gln Ala
                405                 410                 415

Gly Ser Ala Gly Val Leu Val Cys Pro Phe His Thr Phe Val Ser Leu
            420                 425                 430

Cys Tyr Asn Trp Lys Thr Phe Phe Leu Leu Ile Val Ser Ser Cys His
            435                 440                 445

Pro Ser Arg Thr Gly Lys Arg Pro Leu Trp Asp Asp Ser Gln Arg Asn
            450                 455                 460

Lys Asn Leu Leu Pro Pro Gln Arg Thr Leu Gly Pro Lys Val Cys Arg
465                 470                 475                 480

Asp

<210> SEQ ID NO 23
<211> LENGTH: 359
<212> TYPE: PRT
<213> ORGANISM: human

<400> SEQUENCE: 23

Ala Ala Met Arg Ser Gly Gly Arg Gly Arg Pro Arg Leu Arg Leu Gly
1               5                   10                  15

Glu Arg Gly Leu Met Glu Pro Leu Leu Pro Lys Arg Arg Leu Leu
            20                  25                  30

Pro Arg Val Arg Leu Leu Pro Leu Leu Leu Ala Leu Ala Val Gly Ser
```

|  | 35 |  |  |  | 40 |  |  |  | 45 |  |  |  |
|---|---|---|---|---|---|---|---|---|---|---|---|---|
| Ala | Phe | Tyr | Thr | Ile | Trp | Ser | Gly | Trp | His | Arg | Thr | Glu | Glu | Leu |
| 50 |  |  |  |  | 55 |  |  |  | 60 |  |  |  |  |

Ala Phe Tyr Thr Ile Trp Ser Gly Trp His Arg Thr Glu Glu Leu
 50                  55                  60

Pro Leu Gly Arg Glu Leu Arg Val Pro Leu Ile Gly Ser Leu Pro Glu
 65                  70                  75                  80

Ala Arg Leu Arg Arg Val Val Gly Gln Leu Asp Pro Gln Arg Leu Trp
             85                  90                  95

Ser Thr Tyr Leu Arg Pro Leu Leu Val Val Arg Thr Pro Gly Ser Pro
            100                 105                 110

Gly Asn Leu Gln Val Arg Lys Ala Ala Pro Val Thr Leu Gln Leu Leu
            115                 120                 125

Phe Leu Asp Gly Glu Glu Ala Leu Lys Glu Trp Gly Pro Lys Asp Ser
130                 135                 140

Leu Tyr Gly Ser Arg His Leu Ala Gln Leu Met Glu Ser Ile Pro His
145                 150                 155                 160

Ser Pro Gly Pro Thr Arg Ile Gln Ala Ile Glu Leu Phe Met Leu Leu
                165                 170                 175

Asp Leu Leu Gly Ala Pro Asn Pro Thr Phe Tyr Ser His Phe Pro Arg
                180                 185                 190

Thr Val Arg Trp Phe His Arg Leu Arg Ser Ile Glu Lys Arg Leu His
            195                 200                 205

Arg Leu Asn Leu Leu Gln Ser His Pro Gln Glu Val Met Tyr Phe Gln
210                 215                 220

Pro Gly Glu Pro Phe Gly Ser Val Glu Asp Asp His Ile Pro Phe Leu
225                 230                 235                 240

Arg Arg Gly Val Pro Val Leu His Leu Ile Ser Thr Pro Phe Pro Ala
                245                 250                 255

Val Trp His Thr Pro Ala Asp Thr Glu Val Asn Leu His Pro Pro Thr
            260                 265                 270

Val His Asn Leu Cys Arg Ile Leu Ala Val Phe Leu Ala Glu Tyr Leu
            275                 280                 285

Gly Leu Arg Ala Trp Pro Met Thr Val Glu Arg Thr Val Arg Glu Lys
290                 295                 300

Val Pro Ala Gly Ala Ser Glu Ala Gln Ala Gly Ser Ala Gly Val Leu
305                 310                 315                 320

Val Cys Pro Phe His Thr Phe Val Ser Leu Cys Tyr Asn Trp Lys Thr
                325                 330                 335

Phe Phe Leu Leu Ile Val Ser Ser Cys His Pro Ser Arg Thr Gly Lys
                340                 345                 350

Arg Pro Leu Trp Asp Asp Ser
        355

<210> SEQ ID NO 24
<211> LENGTH: 1086
<212> TYPE: DNA
<213> ORGANISM: human

<400> SEQUENCE: 24
atggcaggcg aagacaccg gcgcgtcgtg ggcaccctcc acctgctgct gctggtggcc      60
gccctgccct gggcatccag gggggtcagt ccgagtgcct cagcctggcc agaggagaag    120
aattaccacc agccagccat tttgaattca tcggctcttc ggcaaattgc agaaggcacc    180
agtatctctg aaatgtggca aaatgactta cagccattgc tgatagagcg atacccggga    240
tcccctggaa gctatgctgc tcgtcagcac atcatgcagc gaattcagag gcttcaggct    300

```
gactgggtct tggaaataga caccttcttg agtcagacac cctatgggta ccggtctttc    360
tcaaatatca tcagcaccct caatcccact gctaaacgac atttggtcct cgcctgccac    420
tatgactcca agtattttc ccactggaac aacagagtgt ttgtaggagc cactgattca     480
gccgtgccat gtgcaatgat gttggaactt gctcgtgcct tagacaagaa actcctttcc    540
ttaaagactg tttcagactc caagccagat ttgtcactcc agctgatctt ctttgatggt    600
gaagaggctt ttcttcactg gtctcctcaa gattctctct atgggtctcg acacttagct    660
gcaaagatgg catcgacccc gcacccacct ggagcgagag gcaccagcca actgcatggc    720
atggatttat tggtcttatt ggatttgatt ggagctccaa acccaacgtt cccaattttt    780
tttccaaact cagccaggtg gttcgaaaga cttcaagcaa ttgaacatga acttcatgaa    840
ttgggtttgc tcaaggatca ctcttttggag ggcggtatt tccagaatta cagttatgga    900
ggtgtgattc aggatgacca tattccattt ttaagaagag gtgttccagt tctgcatctg    960
ataccgtctc ctttccctga agtctggcac accatggatg acaatgaaga aaatttggat   1020
gaatcaacca ttgacaatct aaacaaaatc ctacaagtct ttgtgttgga atatcttcat   1080
ttgtaa                                                              1086

<210> SEQ ID NO 25
<211> LENGTH: 1149
<212> TYPE: DNA
<213> ORGANISM: human

<400> SEQUENCE: 25
atgcgttccg ggggccgcgg gcgaccccgc ctgcggctgg gggaacgtgg cctcatggag     60
ccactcttgc cgccgaagcg ccgcctgcta ccgcgggttc ggctcttgcc tctgttgctg    120
gcgctggccg tgggctcggc gttctacacc atttggagcg gctggcaccg caggactgag    180
gagctgccgc tgggccggga gctgcgggtc ccattgatcg gaagcctccc cgaagcccgg    240
ctgcggaggg tggtgggaca actggatcca cagcgtctct ggagcactta tctgcgcccc    300
ctgctggttg tgcgaacccc gggcagcccg ggaaatctcc aagtcagaaa gttcctggag    360
gccacgctgc ggtccctgac agcaggttgg cacgtgagc tggatccctt cacagcctca    420 acaccctgg ggccagtgga cttggcaat gtggtggcca cactggaccc aagggctgcc    480
cgtcacctca cccttgcctg ccattatgac tcgaagctct tcccacccgg atcgaccccc    540
tttgtagggg ccacggattc ggctgtgccc tgtgccctgc tgctggagct ggcccaagca    600
cttgacctgg agctgagcag ggccaaaaaa caggcagccc cggtgaccct gcaactgctc    660
ttcttggatg gtgaagaggc gctgaaggag tggggaccca aggactccct ttacggttcc    720
cggcacctgg cccagctcat ggagtctata cctcacagcc ccggcccac caggatccag    780 gctattgagc tctttatgct tcttgatctc ctgggagccc ccaatcccac cttctacagc    840 cacttcccctc gcacggtccg ctggttccat cggctgagga gcattgagaa gcgtctgcac    900
cgtttgaacc tgctgcagtc tcatccccag gaagtgatgt acttccaacc cggggagccc    960
tttggctctg tggaagacga ccacatcccc ttcctccgca gaggggtacc cgtgctccat   1020
ctcatctcca cgcccttccc tgctgtctgg cacaccctg cggacaccga ggtcaatctc    1080
cacccaccca cggtacacaa cttgtgccgc attctcgctg tgttcctggc tgaatacctg   1140
gggctctag                                                           1149

<210> SEQ ID NO 26
<211> LENGTH: 1145
<212> TYPE: DNA
```

<213> ORGANISM: human

<400> SEQUENCE: 26

| | | | | | |
|---|---|---|---|---|---|
| atgcgttccg | ggggccgcgg | gcgaccccgc | ctgcggctgg | gggaacgtgg | atggagccac | 60 |
| tcttgccgcc | gaagcgccgc | ctgctaccgc | gggttcggct | cttgcctctg | ttgctggcgc | 120 |
| tggccgtggg | ctcggcgttc | tacaccattt | ggagcggctg | gcaccgcagg | actgaggagc | 180 |
| tgccgctggg | ccgggagctg | cgggtcccat | tgatcggaag | cctccccgaa | gcccggctgc | 240 |
| ggagggtggt | gggacaactg | gatccacagc | gtctctggag | cacttatctg | cgcccctgc | 300 |
| tggttgtgcg | aacccggggc | agcccgggaa | atctccaagt | cagaaagttc | ctggaggcca | 360 |
| cgctgcggtc | cctgacagca | ggttggcacg | tggagctgga | tcccttcaca | gcctcaacac | 420 |
| ccctggggcc | agtggacttt | ggcaatgtgg | tggccacact | ggacccaagg | gctgcccgtc | 480 |
| acctcacccct | tgcctgccat | tatgactcga | agctcttccc | acccggatcg | accccctttg | 540 |
| tagggggccac | ggattcggct | gtgccctgtg | ccctgctgct | ggagctggcc | caagcacttg | 600 |
| acctggagct | gagcagggcc | aaaaaacagg | cagccccggt | gaccctgcaa | ctgctcttct | 660 |
| tggatggtga | agaggcgctg | aaggagtggg | gacccaagga | ctcccttac | ggttcccggc | 720 |
| acctggccca | gctcatggag | tctataccte | acagccccgg | cccaccagg | atccaggcta | 780 |
| ttgagctctt | tatgcttctt | gatctcctgg | gagcccccaa | tcccaccttc | tacagccact | 840 |
| tccctcgcac | ggtccgctgg | ttccatcggc | tgaggagcat | tgagaagcgt | ctgcaccgtt | 900 |
| tgaacctgct | gcagtctcat | ccccaggaag | tgatgtactt | caacccggg | agcccttg | 960 |
| gctctgtgga | agacgaccac | atccccttcc | tccgcagagg | ggtacccgtg | ctccatctca | 1020 |
| tctccacgcc | cttccctgct | gtctggcaca | cccctgcgga | caccgaggtc | aatctccacc | 1080 |
| cacccacggt | acacaacttg | tgccgcattc | tcgctgtgtt | cctggctgaa | tacctggggc | 1140 |
| tctag | | | | | 1145 |

<210> SEQ ID NO 27
<211> LENGTH: 1149
<212> TYPE: DNA
<213> ORGANISM: Macaca fascicularis

<400> SEQUENCE: 27

| | | | | | |
|---|---|---|---|---|---|
| atgcgttccg | ggggccgcgg | gcggccccgc | ctgcggctag | gggaacgtgg | cgttatggag | 60 |
| ccactcttgc | ccccgaagcg | ccgcctgcta | ccgcgggttc | ggctcttgcc | cctgttgctg | 120 |
| gcgctggccg | tgggctcggc | gttctacacc | atttggagcg | gctggcaccg | caggactgag | 180 |
| gagctgccgc | tgggccggga | gctgcgggtc | ccgttgatcg | gaagccttcc | gaagcccgg | 240 |
| ctgcggaggg | tggtgggaca | actggaccca | cagcgtctct | ggggcactta | tctgcgcccc | 300 |
| ctgctggttg | tgcgaacccc | aggcagcccg | ggaaatctcc | aagtcagaaa | gttcctggag | 360 |
| gccacgctgc | ggtccctgac | agcaggttgg | cacgtggagc | tggatccctt | cacagcctcg | 420 |
| acgcccctgg | ggccagtgga | ctttggcaat | gtggtggcca | cgctggaccc | ggggctgcc | 480 |
| cgtcacctca | cccttgcctg | ccattatgac | tcgaagctct | tcccacccgg | atcgaccccg | 540 |
| tttgtagggg | ccacggactc | ggctgtgccc | tgtgccctgc | tgctggagct | ggcccaggca | 600 |
| cttgacctgg | agctgagcag | ggccaaagaa | caggcagccc | cggtgaccct | gcaactgctc | 660 |
| ttcctggatg | gtgaagaggc | gctgaaggag | tggggaccca | aggactccct | ttacggttcc | 720 |
| cggcacctgg | cccagctcat | ggagtctata | cctcatagcc | ccggcccac | caggatccag | 780 |
| gctattgagc | tctttatgct | tcttgatctc | ctgggagccc | ccaatcccac | cttctacagc | 840 |

```
cacttccctc gcacggtccg ctggttccat cggctgagaa gcattgagaa gcgtctgcac    900
cgtttgaacc tgctgcagtc tcatcccag gaagtgatgt acttccaacc cggggagccc    960
ttcggctctg tggaagacga ccacatcccc ttcctccgca gaggggtccc cgtgctccat   1020
ctcatctcta cgcccttccc tgctgtctgg cacacccctg cggacacaga ggccaatctc   1080
cacccgccca cggtacacaa cttaagccgc attctggccg tgttcctggc tgaatacctg   1140
gggctctag                                                           1149
```

<210> SEQ ID NO 28
<211> LENGTH: 1149
<212> TYPE: DNA
<213> ORGANISM: Macaca mulatta

<400> SEQUENCE: 28

```
atgcgttccg ggggccgcgg gcggccccgc ctgcggctag ggaacgtgg cgttatggag     60 ccactcttgc ccccgaagcg ccgcctgcta ccgcgggttc ggctcttgcc cctgttgctg    120
gcgctggccg tgggctcggc gttctacacc atttggagcg gctggcaccg caggactgag    180
gagctgccgc tgggccggga gctgcgggtc ccgttgatcg gaagccttcc cgaagcccgg    240
ctgcggaggg tggtgggaca actggaccca cagcgtctct ggggcactta tctgcgcccc    300
ctgctggttg tgcgaacccc aggcagcccg gaaatctcc aagtcagaaa gttcctggag    360
gccacgctgc ggtccctgac agcaggttgg cacgtggagc tggatcccct cacagcctcg    420
acgcccctgg gccagtggga ctttggcaat gtggtggcca cgctggaccc ggggctgcc    480 cgtcacctca cccttgcctg ccattatgac tcgaagctct ccccaccgg atcgaccccg    540 tttgtagggg ccacagactc ggctgtgccc tgtgccctgc tgctggagct ggcccaggca    600
cttgacctgg agctgagcag ggccaaagaa caggcagccc cggtgaccct gcaactgctc    660
ttcctggatg gtgaagaggc gctgaaggag tggggaccca aggactccct ttacggttcc    720
cggcacctgg cccagctcat ggagtctata cctcatagcc ccggcccccac caggatccag    780 gctattgagc tctttatgct tcttgatctc ctgggagccc ccaatcccac cttctacagc    840
cacttccctc gcacggtccg ctggttccat cggctgagaa gcattgagaa gcgtctgcac    900
cgtttgaacc tgctgcagtc tcatcccag gaagtgatgt acttccaacc cggggagccc    960
tttggctctg tggaagacga ccacatcccc ttcctccgca gaggggtccc cgtgctccat   1020
ctcatctcta cgcccttccc tgctgtctgg cacacccctg cggacacaga ggccaatctc   1080
cacccgccca cggtacacaa cttaagccgc attctggccg tgttcctggc tgaatacctg   1140
gggctctag                                                           1149
```

<210> SEQ ID NO 29
<211> LENGTH: 1152
<212> TYPE: DNA
<213> ORGANISM: Canis familiaris

<400> SEQUENCE: 29

```
atgccttccg ggggccgcgg gcggtcccgg ctacggctcg ggaacgtgg cctcttggag     60 ccgccctccc cgcccaagcg ccgcctgctc ccgcgggcgc acttcttgcc tctgcttctg    120
ctggccctgg ccctggcttc ggcgacctac accatctgga gcggctggca ccaccagact    180
gaggagctgc cgcggggccg ggagctgcgg ggccgcttga tcggaagcct ctccgaagcc    240
cggctgcggc gggtggtggg gcaactggac ccacaccgtc tctggaacac ttatctgcgc    300
cccctgctgg ttgtgcggac cccgggcagc cccggcaatc tccaagtcag aaagttcctg    360
```

| | |
|---|---|
| gaggctacac tacggacctt gacagcaggc tggcatgtgg aactggaccc cttcacagcc | 420 |
| ttgacacccc tggggccact ggactttggc aatgtggtgg ccacgctgga cccaggggct | 480 |
| gcccgtcacc tcacccttgc ctgccattat gactccaagc tcttcgcatc tgagtcggtt | 540 |
| cccttgtgg gggcaacaga ttcggctgta ccttgcgccc tgctgctgga gctggctcag | 600 |
| gccctcgaca gggagttgag tagggccaag gagcaggaag ccccggtgac tctgcagctg | 660 |
| ctcttttgg atggtgaaga agcactgaag gagtggggac ccacagactc cctctatggc | 720 |
| tcccggcacc tggcccagct catggagtct gcaccccaca gcccgggccc caccaggatc | 780 |
| caggctatcg agctcttcat gctccttgat ctcctgggtg cccgaatcc aaacttctac | 840 |
| agtcacttcc ctcatacagc ccgctggttc catcggctga ggagcatcga gaagcgcctt | 900 |
| caccgcatga acctgctgca gtctcatccc caggaagtga tgtacttcca gcccggggag | 960 |
| cccctggtt ctgtggaaga tgaccacatc cccttcctcc gccgaggggt ccctgtgctc | 1020 |
| cacctcatct ccatgccctt cccctccgtc tggcacaccc ccgatgactc tgaggccaac | 1080 |
| ctgcacccac ccaccgtaca caatctgagc cgcatcctcg ccgtgttcct ggccgaatat | 1140 |
| ctggggctct ag | 1152 |

<210> SEQ ID NO 30
<211> LENGTH: 1152
<212> TYPE: DNA
<213> ORGANISM: Rattus norvegicus

<400> SEQUENCE: 30

| | |
|---|---|
| atgagtccgg ccagccgcgg gcggtctcgg cagcggctcg gggatcgcgg cctcatgaaa | 60 |
| ccacccctcac tttccaagcg ccgtcttctg ccgcgggtgc agctcctgcc cctgctgctg | 120 |
| ctggcgctgg ccctgggctt ggcttttat atcgtctgga atagctggca ccctgggtt | 180 |
| gaggaggtat cacggagccg ggatctgcgg gtcccgctga tcggaagcct ttcagaagcc | 240 |
| aagctgcggc ttgtggtagg gcagctggat ccacagcgtc tctggggaac tttctgcgt | 300 |
| cccttgttga ttgtacgacc cccaggtagt cctggcaatc tccaagtgag aaagttcctg | 360 |
| gaggctacgt tgcagtccct atcggcaggc tggcacgtgg aactggaccc attcacagcc | 420 |
| tcaacccct tggggccact ggacttcggg aacgtggtgg ccaccttga cccaggagct | 480 |
| gcccgtcacc tcaccctcgc ctgccattat gactctaagt tcttccctcc tgggttaccc | 540 |
| cccttgtgg gggccacaga ttcagccgtg cctgtgccc tgcttctgga gttagtccag | 600 |
| gcccttgatg tcatgctgag cagaatcaag cagcaggcag caccagtgac cctgcagctg | 660 |
| ctcttcttgg acggggagga ggcactgaag gagtggggac caaaggactc cctctatggt | 720 |
| tcccggcacc tagctcagat catggagtct ataccgcaca gccctggccc caccaggatc | 780 |
| caggctattg agctctttgt ccttcttgac cttctgggag cgcccagtcc aatcttcttc | 840 |
| agtcacttcc ccgcacagc ccgctggttc caacgactgc ggagcatcga gaagcgcctt | 900 |
| caccgtctga acctactgca gtctcacccc caggaagtga tgtacttcca acccggggag | 960 |
| cccctggcc ctgtggaaga tgaccacatc cccttccttc gcagagggt cccgtgctc | 1020 |
| cacctcattg cgatgcccctt cccctgccgtg tggcacacac ctgctgacac tgaggctaac | 1080 |
| ctccacccgc ccacggtgca caacctgagc cgcatcctcg ccgtgttcct ggctgagtac | 1140 |
| ctgggtctct ag | 1152 |

<210> SEQ ID NO 31
<211> LENGTH: 1152
<212> TYPE: DNA

<213> ORGANISM: Mus musculus

<400> SEQUENCE: 31

| | |
|---|---|
| atgagtcccg ggagccgcgg gcggccccgg cagcggctcg aggatcgtgg cctcatgaaa | 60 |
| ccaccctcac tttccaagcg ccgtcttctg ccgcgagtgc agttcctgcc cctgctgctg | 120 |
| ctggcgctgg ctatgggctt ggctttctat atcgtctgga acagctggca ccctggggtt | 180 |
| gaggagatgt cacggagccg ggatctgcgg gtcccgctga tcggaagcct ttcagaagcc | 240 |
| aagctgcggc tggtggtagg gcagctggat ccgcagcgtc tctggggaac tttcctgcgt | 300 |
| cccttattga ttgtgcgacc cccgggtagt tctggcaatc tccaagtgag aaagttcctg | 360 |
| gaggctacgt tgcagtccct gtcggcaggc tggcatgttg aactggaccc attcacggcc | 420 |
| tcaacccccT tggggccact ggacttcggg aacgtggtgg ccacacttga cccaggagct | 480 |
| gcccgtcacc tcaccctcgc ctgccattat gactctaagt tcttccctcc ggggttgccc | 540 |
| ccctttgtgg gggccacaga ttcagctgtg ccctgtgccc tgcttctgga gttggtccag | 600 |
| gcccttgatg ccatgctgag cagaatcaag cagcaggcag caccggtgac cctgcagctg | 660 |
| cttttcttgg atggggagga ggcactgaag gagtggggac caaaggactc cctctatggc | 720 |
| tcccggcacc tagctcagat catggagtct ataccacaca gccctggccc caccaggatc | 780 |
| caggctattg agctctttgt cctcctcgac cttctgggag catccagtcc gatcttcttc | 840 |
| agtcacttcc ctcgcacagc ccgctggttc cagcgactga ggagcattga aagcgcctt | 900 |
| caccggctga acctactgca gtctcacccc caggaagtga tgtacttcca acccggggag | 960 |
| cccccggcc ctgtggaaga tgaccacatc cccttccttc gcagaggggt cccggtgctc | 1020 |
| cacctcattg ccacgccctt ccctgctgtg tggcacacac ctgctgacac cgaggccaac | 1080 |
| ctccacccac ccactgtgca taacctgagc cgcatccttg ctgtgttcct ggccgagtac | 1140 |
| ctgggactct ag | 1152 |

<210> SEQ ID NO 32
<211> LENGTH: 1152
<212> TYPE: DNA
<213> ORGANISM: Bos taurus

<400> SEQUENCE: 32

| | |
|---|---|
| atgccttccg ggggccgcgg gcggccccgg ctccaggtcg gggaacgcag cctttggag | 60 |
| cgaccctcac cgcccaagcg ccgcctgata ccgcgggcac agctgttgcc ccagctgctg | 120 |
| ctggctctga cggtagcctc ggtgttctat accatttgga ggatctggca tagccagact | 180 |
| gaagagctac cgctggggcg ggagctgcgg ggcccttga tcggaagcct ccccgaagct | 240 |
| cgggtgcgga gggtagtggg gcaactggac cctcaccgtc tctggaacac tttcctgcgc | 300 |
| cctctgctgg ttgtacggac tccgggcagc ccgggcaatc tccaagtgag aaagttcctg | 360 |
| gaggctacgc tgcggacact ttcagcaggc tggcatatag aactcgactc cttcactgcc | 420 |
| tccacacccg tggggccatt ggacttcagc aatgtggtgg ccacgctgga cccaggggct | 480 |
| gcccgccacc ttaccccttgc ctgccattat gactccaagc tcttcccatc tgactcagcc | 540 |
| ccctttgtgg gggccacgga ttcggcagtg ccttgctccc tgctactgga gctggcccaa | 600 |
| gcccttgacc aggagctggg caaagccaag gagagggcag cgccaatgac cttgcagctg | 660 |
| atcttcctgg atggtgaaga ggcactgaag cagtggggac ccaaggactc gctttatggc | 720 |
| tcccggcacc tggcccagct catggagtct acacccacg gctgggctc caccaggatc | 780 |
| caggctattg agctctttat gcttcttgat ctcctgggag ccccaacccc gaccttctac | 840 |

```
agtcacttcc ctcgcacggc ccgctggttc catcggctca ggagcattga gaagcgcctg     900
caccgtctga acctcctgca gtctcatcct tgggaagtga tgtacttcca gaccggggag     960
ccccccggct ccgtggaaga cgaccacatc ccgttcctcc gccgaggagt tcccgtgctc    1020
cacctcatcg ccacacccct tcccctctgtc tggcacacgt ccgatgactc cgaggccaac    1080
ctgcacccac ccacggtaca aacctgagc cgcatcctgg ccgtgttcct ggctgagtac    1140
ctggggctct ag                                                         1152

<210> SEQ ID NO 33
<211> LENGTH: 1457
<212> TYPE: DNA
<213> ORGANISM: human

<400> SEQUENCE: 33
gtctggtaca ggtttcaggg caaagcggcc atgcgttccg ggggccgcgg gcgaccccgc      60
ctgcggctgg gggaacgtgg cctcatggag ccactcttgc cgccgaagcg ccgcctgcta     120 ccgcggggttc ggctcttgcc tctgttgctg gcgctggccg tgggctcggc gttctacacc    180
atttggagcg gctggcaccg caggactgag gagctgccgc tgggccggga gctgcgggtc    240
ccattgatcg gaagcctccc cgaagcccgg ctgcggaggg tggtgggaca actggatcca    300
cagcgtctct ggagcactta tctgcgcccc tgctggttg tgcgaacccc gggcagcccg     360
ggaaatctcc aagtcagaaa gttcctggag gccacgctgc ggtccctgac agcaggttgg    420
cacgtggagc tggatccctt cacagcctca acacccctgg ggccagtgga ctttggcaat    480
gtggtggcca cactggaccc aagggctgcc cgtcacctca cccttgcctg ccattatgac    540
tcgaagctct ccccacccgg atcgaccccc tttgtagggg ccacggattc ggctgtgccc    600
tgtgccctgc tgctggagct ggcccaagca cttgacctgg agctgagcag gccaaaaaa    660 caggcagccc cggtgaccct gcaactgctc ttcttggatg gtgaagaggc gctgaaggag    720
tggggaccca aggactccct ttacggttcc cggcacctgg cccagctcat ggagtctata    780
cctcacagcc ccggccccac caggatccag gctattgagc tctttatgct tcttgatctc    840
ctgggagccc caatcccac cttctacagc cacttccctc gcacggtccg ctggttccat    900
cggctgagga gcattgagaa gcgtctgcac cgtttgaacc tgctgcagtc tcatccccag    960
gaagtgatgt acttccaacc cggggagccc tttggctctg tggaagacga ccacatcccc   1020
ttcctccgca gaggggtacc cgtgctccat ctcatctcca cgcccttccc tgctgtctgg    1080
cacacccctg cggacaccga ggtcaatctc caccccaccca cggtacacaa cttgtgccgc    1140
attctcgctg tgttcctggc tgaatacctg gggctctagc gtgcttggcc aatgactgtg    1200
gagaggactg tgagagagaa ggtcccagcg ggggccagtg aagctcaggc aggatctgcc    1260
tagggtgtgc tggtttgtcc ttttcatacc tttgtctcct aattgtgcta caattggaag    1320
accttctttc ttttgattgt ctcaagctgc caccttcaa ggacaggaa gagaccactg    1380 tgggatgaca gccagaggaa taagaacttg ctccctcccc agaggtaaac acttggtcca    1440
aaggtttgca gggacca                                                   1457

<210> SEQ ID NO 34
<211> LENGTH: 1088
<212> TYPE: DNA
<213> ORGANISM: human

<400> SEQUENCE: 34
agcggccatg cgttccgggg gccgcgggcg accccgcctg cggctggggg aacgtggcct      60
```

```
catggagcca ctcttgccgc cgaagcgccg cctgctaccg cgggttcggc tcttgcctct      120
gttgctggcg ctggccgtgg gctcggcgtt ctacaccatt tggagcggct ggcaccgcag      180
gactgaggag ctgccgctgg gccgggagct gcgggtccca ttgatcggaa gcctccccga      240
agcccggctg cggagggtgg tgggacaact ggatccacag cgtctctgga gcacttatct      300 gcgcccctg ctggttgtgc gaaccccggg cagcccggga aatctccaag tcagaaaggc       360
agccccggtg accctgcaac tgctcttctt ggatggtgaa gaggcgctga aggagtgggg      420
acccaaggac tcccttacg gttcccggca cctggcccag ctcatggagt ctatacctca      480
cagccccggc cccaccagga tccaggctat tgagctcttt atgcttcttg atctcctggg      540 agccccccaat cccaccttct acagccactt ccctcgcacg gtccgctggt tccatcggct      600
gaggagcatt gagaagcgtc tgcaccgttt gaacctgctg cagtctcatc ccaggaagt      660 gatgtacttc caacccgggg agccctttgg ctctgtggaa gacgaccaca tccccttcct      720
ccgcagaggg gtaccgtgc tccatctcat ctccacgccc ttccctgctg tctggcacac       780
ccctgcggac accgaggtca atctccaccc acccacggta cacaacttgt gccgcattct      840
cgctgtgttc ctggctgaat acctggggct ctagcgtgct tggccaatga ctgtggagag      900
gactgtgaga gagaaggtcc cagcgggggc cagtgaagct caggcaggat ctgcctaggg      960
tgtgctggtt tgtcctttc atacctttgt ctcctaattg tgctacaatt ggaagaccctt     1020 cttcttttg attgtctcaa gctgccaccc ttcaaggaca gggaagagac cactgtggga     1080
tgacagcc                                                             1088

<210> SEQ ID NO 35
<211> LENGTH: 32
<212> TYPE: DNA
<213> ORGANISM: Artificial sequence
<220> FEATURE:
<223> OTHER INFORMATION: DNA Primer

<400> SEQUENCE: 35
atatgcatgc atggcaggca gcgaagacaa gc                                     32

<210> SEQ ID NO 36
<211> LENGTH: 40
<212> TYPE: DNA
<213> ORGANISM: Artificial sequence
<220> FEATURE:
<223> OTHER INFORMATION: DNA Primer

<400> SEQUENCE: 36
atataagctt ttacaagtga agatattcca acacaaagac                             40

<210> SEQ ID NO 37
<211> LENGTH: 33
<212> TYPE: DNA
<213> ORGANISM: Artificial sequence
<220> FEATURE:
<223> OTHER INFORMATION: DNA Primer

<400> SEQUENCE: 37
atactcgaga aaagagcctg gacgcaggag aag                                    33

<210> SEQ ID NO 38
<211> LENGTH: 31
<212> TYPE: DNA
<213> ORGANISM: Artificial sequence
<220> FEATURE:
<223> OTHER INFORMATION: DNA Primer
```

```
<400> SEQUENCE: 38
atatctagat tacaagtgaa gatattccaa c                              31

<210> SEQ ID NO 39
<211> LENGTH: 26
<212> TYPE: DNA
<213> ORGANISM: Artificial sequence
<220> FEATURE:
<223> OTHER INFORMATION: PCR primer

<400> SEQUENCE: 39
agtaatgaag tcacccagca gggagg                                    26

<210> SEQ ID NO 40
<211> LENGTH: 25
<212> TYPE: DNA
<213> ORGANISM: Artificial sequence
<220> FEATURE:
<223> OTHER INFORMATION: PCR primer

<400> SEQUENCE: 40
tgatccagga atctaaggca gcacc                                     25

<210> SEQ ID NO 41
<211> LENGTH: 19
<212> TYPE: DNA
<213> ORGANISM: Artificial sequence
<220> FEATURE:
<223> OTHER INFORMATION: PCR primer

<400> SEQUENCE: 41
gccacggatt cagctgtgc                                            19

<210> SEQ ID NO 42
<211> LENGTH: 20
<212> TYPE: DNA
<213> ORGANISM: Artificial sequence
<220> FEATURE:
<223> OTHER INFORMATION: Synthetic peptide

<400> SEQUENCE: 42
gaatgttgga tttgctgctc                                           20

<210> SEQ ID NO 43
<211> LENGTH: 19
<212> TYPE: DNA
<213> ORGANISM: Artificial sequence
<220> FEATURE:
<223> OTHER INFORMATION: Synthetic nucleotide

<400> SEQUENCE: 43
ttgaggaaag acctccagc                                            19

<210> SEQ ID NO 44
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 44
catgagtcca atgattgcac c                                         21
```

TRANSGENIC MOUSE MODELS OF Aβ OVEREXPRESSION

CROSS-REFERENCE TO RELATED APPLICATIONS

This application claims priority from U.S. Provisional Application Ser. No. 60/971,631 filed on Sep. 12, 2007, which is incorporated herein by reference in its entirety to the extent permitted by law.

INCORPORATION-BY-REFERENCE OF SEQUENCE LISTING

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present invention relates generally to transgenic animals as well as methods and compositions for screening and treating diseases, especially in relation to Aβ-peptides.

In particular the invention relates to Aβ peptides and QPCT (i.e. glutaminyl peptide cyclotransferase), and QPCT-like enzymes (QPCTL) also named glutaminyl cyclase (QC, EC 2.3.2.5) that catalyze the intramolecular cyclization of N-terminal glutamine residues into pyroglutamic acid (5-oxo-proline, pGlu*) under liberation of ammonia and the intramolecular cyclization of N-terminal glutamate residues into pyroglutamic acid under liberation of water.

BACKGROUND OF THE INVENTION

In plaques, found in Alzheimer's disease (AD), only a small proportion of Aβ peptides begin with an N-terminal aspartate (AβN1D). The majority starts at position 3 with pyroglutamate (AβN3(pGlu))(Kuo, Y. M., Emmerling, M. R., Woods, A. S., Cotter, R. J. & Roher, A. E. Isolation, chemical characterization, and quantitation of Abeta 3-pyroglutamyl peptide from neuritic plaques and vascular amyloid deposits. Biochem Biophys Res Commun 237, 188-191. (1997); Saido, T. C., et al. Dominant and differential deposition of distinct beta-amyloid peptide species, AbetaN3(pE), in senile plaques. Neuron 14, 457-466 (1995)), and ends at position 42. Aβ starting with N-terminal glutamine (AβN3Q) is a better substrate for cyclization by glutaminyl cyclase (QC) than Aβ starting with N-terminal glutamate (AβN3E), (Schilling, S., Hoffmann, T., Manhart, S., Hoffmann, M. & Demuth, H. U. Glutaminyl cyclases unfold glutamyl cyclase activity under mild acid conditions. FEBS Lett 563, 191-196 (2004); Cynis, H., et al. Inhibition of glutaminyl cyclase alters pyroglutamate formation in mammalian cells. Biochim Biophys Acta 1764, 1618-1625 (2006)).

Aβ(N3pGlu) has a higher aggregation propensity (He, W. & Barrow, C. J. The Abeta 3-pyroglutamyl and 11-pyroglutamyl peptides found in senile plaque have greater beta-sheet forming and aggregation propensities in vitro than full-length Abeta Biochemistry, 38, 10871-10877 (1999); Schilling, S., et al., On the seeding and oligomerization of pGlu-amyloid peptides (in vitro), Biochemistry, 45, 12393-12399 (2006)) and stability (Kuo, Y. M., Webster, S., Emmerling, M. R., De Lima, N. & Roher, A. E. Irreversible dimerization/tetramerization and post-translational modifications inhibit proteolytic degradation of Abeta peptides of Alzheimer's disease. Biochim Biophys Acta 1406, 291-298 (1998)), and shows an increased toxicity compared to full-length Aβ (Russo, C., et al. Pyroglutamate-modified amyloid-peptides—A N3(pE)—strongly affect cultured neuron and astrocyte survival, Journal of Neurochemistry 82, 1480-1489 (2002)). However, other studies reported that the toxicity of Aβ(N3pGlu-40) and Aβ(N3pGlu-42) is similar to that of Aβ(N1D-40) and AβN1D-42)(Tekirian, T. L., Yang, A. Y., Glabe, C. & Geddes, J. W. Toxicity of pyroglutaminated amyloid beta-peptides 3(pE)-40 and -42 is similar to that of Abeta1-40 and -42, J Neurochem 73, 1584-1589 (1999)), and that Aβ(N3pGlu) is not the major variant in Aβ brain (Lernere, C. A., et al. Sequence of deposition of heterogeneous amyloid beta-peptides and APO E in Down syndrome: implications for initial events in amyloid plaque formation, Neurobiol Dis 3, 16-32 (1996)). Schilling et al. have demonstrated that pyroglutamate-modified peptides display an up to 250-fold acceleration in the initial formation of Aβ aggregates (Schilling, S., et al., On the seeding and oligomerization of pGlu-amyloid peptides (in vitro), Biochemistry, 45, 12393-12399 (2006)), and presented in vitro evidence that the cyclization of glutamate at position 3 of Aβ is driven enzymatically by glutaminyl cyclase (QC) (Schilling, S., Hoffmann, T., Manhart, S., Hoffmann, M. & Demuth, H. U. Glutaminyl cyclases unfold glutamyl cyclase activity under mild acid conditions, FEBS Lett 563, 191-196 (2004); Cynis, H., et al. Inhibition of glutaminyl cyclase alters pyroglutamate formation in mammalian cells, Biochim Biophys Acta, 1764, 1618-1625 (2006)). QC inhibition leads to significantly reduced Aβ(N3pGlu) formation, showing the importance of QC-activity during cellular maturation of pyroglutamate-containing peptides (Cynis, H., et al. Inhibition of glutaminyl cyclase alters pyroglutamate formation in mammalian cells, Biochim Biophys Acta 1764, 1618-1625 (2006)). APP transgenic mouse models have been reported to show no (Kuo, Y. M., et al. Comparative analysis of amyloid-beta chemical structure and amyloid plaque morphology of transgenic mouse and Alzheimer's disease brains. J Biol Chem 276, 12991-12998 (2001)) or low Aβ(N3pGlu) levels (Guntert, A., Dobeli, H. & Bohrmann, B. High sensitivity analysis of amyloid-beta peptide composition in amyloid deposits from human and PS2APP mouse brain. Neuroscience. 143, 461-475 (2006)), in contrast to the APP/PS1KI mouse, which harbours considerable amounts of Aβ(N3pGlu) detected by 2D-gel electrophoresis of whole brain lysates (Casas, C., et al. Massive CA1/2 Neuronal Loss with Intraneuronal and N-Terminal Truncated A{beta}42 Accumulation in a Novel Alzheimer Transgenic Model. Am J Pathol 165, 1289-1300 (2004)) and by immunohistochemistry within neurons and plaques (Wirths, O., Weis, J., Kayed, R., Saido, T. C. & Bayer, T. A. Age-dependent axonal degeneration in an Alzheimer mouse model, Neurobiol Aging 8, online version (2006)). The APP/PS1KI mice develop age-dependent axonal degeneration in brain and spinal cord (Wirths, O., Weis, J., Kayed, R., Saido, T. C. & Bayer, T. A. Age-dependent axonal degeneration in an Alzheimer mouse model, Neurobiol Aging 8, online version (2006)), a 50% neuron loss in CA1 at 10 months of age (Casas, C., et al. Massive CA1/2 Neuronal Loss with Intraneuronal and N-Terminal Truncated A {beta}42 Accumulation in a Novel Alzheimer Transgenic Model. Am J Pathol 165, 1289-1300 (2004)), and deficits in working memory and motor performance at 6 months of age (Wirths, O., Breyhan, H., Schafer, S., Roth, C. & Bayer, T. A. Deficits in working memory and motor performance in the APP/PS Iki mouse model for Alzheimer's disease, Neurobiol Aging 8, 8 (2007)). Between 2 and 6 months of age, the rate of Aβ(N3pGlu) aggregation was higher than the rate of unmodified Aβ(N1D).

Although suggestive, it is difficult to correlate between Aβ(N3pGlu) deposition and the observed CA1 neuron loss in this model, due to the larger heterogeneity of N-truncated Aβ peptides (Casas, C., et al. Massive CA1/2 Neuronal Loss with Intraneuronal and N-Terminal Truncated A {beta}42 Accumulation in a Novel Alzheimer Transgenic Model. Am J Pathol 165, 1289-1300. (2004)).

Glutaminyl cyclase (QC, EC 2.3.2.5) catalyzes the intramolecular cyclization of N-terminal glutamine residues into pyroglutamic acid (pGlu*) under concomitant liberation of ammonia. A QC was first isolated by Messer from the Latex of the tropical plant Carica papaya in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QCs, the conversion of N-terminal Gln into pGlu by QC has been shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In case of the enzyme from C. papaya, a role in the plant defence against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from C. papaya and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

EP 02 011 349.4 discloses polynucleotides encoding insect glutaminyl cyclase, as well as polypeptides encoded thereby. This application further provides host cells comprising expression vectors comprising polynucleotides of the invention. Isolated polypeptides and host cells comprising insect QC are useful in methods of screening for agents that reduce glutaminyl cyclase activity. Such agents are described as useful as pesticides.

The subject matter of the present invention is particularly useful in the field of Aβ-related diseases, one example of those being Alzheimer's Disease. Alzheimer's disease (AD) is characterized by abnormal accumulation of extracellular amyloidotic plaques closely associated with dystrophic neurones, reactive astrocytes and microglia (Terry, R. D. and Katzman, R. 1983 Ann Neurol 14, 497-506; Glenner, G. G. and Wong, C. W. 1984 Biochem Biophys Res Comm 120, 885-890; Intagaki, S. et al. 1989 J Neuroimmunol 24, 173-182; Funato, H. et al. 1998 Am J Pathol 152, 983-992; Selkoe, D. J. 2001 Physiol Rev 81, 741-766). Amyloid-beta (abbreviated as Aβ) peptides are the primary components of senile plaques and are considered to be directly involved in the pathogenesis and progression of AD, a hypothesis supported by genetic studies (Glenner, G. G. and Wong, C. W. 1984 Biochem Biophys Res Comm 120, 885-890; Borchelt, D. R. et al. 1996 Neuron 17, 1005-1013; Lernere, C. A. et al. 1996 Nat Med 2, 1146-1150; Mann, D. M. and Iwatsubo, T. 1996 Neurodegeneration 5, 115-120; Citron, M. et al. 1997 Nat Med 3, 67-72; Selkoe, D. J. 2001 Physiol Rev 81, 741-766). Aβ is generated by proteolytic processing of the β-amyloid precursor protein (APP) (Kang, J. et al. 1987 Nature 325, 733-736; Selkoe, D. J. 1998 Trends Cell Biol 8, 447-453), which is sequentially cleaved by β-secretase at the N-terminus and by γ-secretase at the C-terminus of Aβ (Haass, C. and Selkoe, D. J. 1993 Cell 75, 1039-1042; Simons, M. et al. 1996 J Neurosci 16 899-908). In addition to the dominant Aβ peptides starting with L-Asp at the N-terminus (Aβ1-42/40), a great heterogeneity of N-terminally truncated forms occurs in senile plaques. Such shortened peptides are reported to be more neurotoxic in vitro and to aggregate more rapidly than the full-length isoforms (Pike, C. J. et al. 1995 J Biol Chem 270, 23895-23898). N-truncated peptides are known to be overproduced in early onset familial AD (FAD) subjects (Saido, T. C. et al. 1995 Neuron 14, 457-466; Russo, C, et al. 2000 Nature 405, 531-532), to appear early and to increase with age in Down's syndrome (DS) brains (Russo, C. et al. 1997 FEBS Lett 409, 411-416, Russo, C. et al. 2001 Neurobiol Dis 8, 173-180; Tekirian, T. L. et al. 1998 J Neuropathol Exp Neurol 57, 76-94). Finally, their amount reflects the progressive severity of the disease (Russo, C. et al. 1997 FEBS Lett 409, 411-416; Guntert, A. et al. 2006 Neuroscience 143, 461-475). Additional post-translational processes may further modify the N-terminus by isomerization or racemization of the aspartate at position 1 and 7 and by cyclization of glutamate at residues 3 and 11. Pyroglutamate-containing isoforms at position 3 [AβN3(pGlu)-40/42] represent the prominent forms—approximately 50% of the total Aβ amount—of the N-truncated species in senile plaques (Mori, H. et al. 1992 J Biol Chem 267, 17082-17086, Saido, T. C. et al. 1995 Neuron 14, 457-466; Russo, C. et al. 1997 FEBS Lett 409, 411-416; Tekirian, T. L. et al. 1998 J Neuropathol Exp Neurol 57, 76-94; Geddes, J. W. et al. 1999 Neurobiol Aging 20, 75-79; Harigaya, Y. et al. 2000 Biochem Biophys Res Commun 276, 422-427) and they are also present in pre-amyloid lesions (Lalowski, M. et al. 1996 J Biol Chem 271, 33623-33631). The accumulation of AβN3 (pE) peptides is likely due to the structural modification that enhances aggregation and confers resistance to most aminopeptidases (Saido, T. C. et al. 1995 Neuron 14, 457-466; Tekirian, T. L. et al. 1999 J Neurochem 73, 1584-1589). This evidence provides clues for a pivotal role of AβN3(pE) peptides in Aβ pathogenesis. However, little is known about their neurotoxicity and aggregation properties (He, W. and Barrow, C. J. 1999 Biochemistry 38, 10871-10877; Tekirian, T. L. et al. 1999 J Neurochem 73, 1584-1589). Moreover, the action of these isoforms on glial cells and the glial response to these peptides are completely unknown, although activated glia cells are strictly associated to senile plaques and might actively contribute to the accumulation of amyloid deposits. In recent studies the toxicity, aggregation properties and catabolism of Aβ1-42, Aβ1-40, [pGlu$^3$]Aβ3-42, [pGlu$^3$]Aβ3-40, [pGlu$^{11}$]Aβ11-42 and [pGlu$^{11}$]Aβ11-40 peptides were investigated in neuronal and glial cell cultures, and it was shown that pyroglutamate modification exacerbates the toxic properties of Aβ-peptides and also inhibits their degradation by cultured astrocytes. Shirotani et al. investigated the generation of [pGlu³]Aβ peptides in primary cortical neurons infected by Sindbis virus in vitro. They constructed amyloid precursor protein complementary DNAs, which encoded a potential precursor of [pGlu³]Aβ by amino acid substitution and deletion. For one artificial precursor starting with an N-terminal glutamine residue instead of glutamate in the natural precursor, a spontaneous conversion or an enzymatic conversion by glutaminyl cyclase to pyroglutamate was suggested. The cyclization mechanism of N-terminal glutamate at position 3 in the natural precursor of [pGlu³]Aβ was neither determined in vitro, in situ nor in vivo (Shirotani, K. et al. 2002 NeuroSci Lett 327, 25-28).

SUMMARY OF THE INVENTION

The present invention comprises methods and compositions for non-human transgenic, in particular mammal, models for Aβ-peptide-related diseases. Specifically, the present invention comprises non-human transgenic animal models that overexpress Aβ-peptide.

The present inventors generated transgenic mouse lines expressing either Aβ3E-42 of SEQ ID No: 1 (tgN3E-42) or AβN3Q-42 of SEQ ID No: 2 (tgN3Q-42). The highest AβN3 (pGlu) levels were observed in tgN3Q-42 mouse brain. Strong expression was observed in a variety of brain areas including hippocampal CA1 neurons and for tgN3Q-42 in cerebellar Purkinje cells. TgN3Q-42 mice developed massive Purkinje cell degeneration, astro- and microglial activation and a severe neurological phenotype, which resulted in premature death. Young (up to 4 weeks of age)tgN3E-42 homozygous mice show no obvious neuropathology, however in tgN3E-42 homozygous mice (age 3 months) strong expression of Aβ was observed in a variety of brain areas, via immunohistochemistry using two different antibodies. These areas included the hippocampal CA1 region, as well various brain stem regions. Purkinje cell staining was found in homozygous and wild type animals using Aβ-directed antibody 4G8, whereas sections labelled with Aβ-directed antibody 6E10 did not show any immunoreactivity here. Immunohistochemical analysis of Aβ(N3pGlu-42) revealed similar staining patterns in CA1 and brain stem, but additionally showed labelling in CA3. These data corroborate an apparent alteration in CA1 morphology.

Double immunofluorescence staining of glia and Aβ(N3pGlu-42) revealed highly elevated numbers of glia within the CA1 region of tgN3E-42 mice (FIG. 3). Homozygous tgN3E-42 mice show a progressive phenotype with neurodegeneration combined with emotional changes (FIG. 8), cognitive decline (FIG. 9A, FIG. 9B and FIG. 9C) and impaired weight gain caused by motor deficitss (FIG. 10). These findings clearly show a relationship of formation of Aβ(N3pGlu-42) and histopathology. Most importantly, the models described here are the first with significant accumulation of Aβ(N3pGlu-42) at an age of several weeks, which is accompanied by neuronal loss. These unique results promote the transgenic strategy applied in the transgenic mice to a superior approach to investigate the neurotoxic properties of distinct amyloid peptides. The prepro-strategy described here might therefore be applied for other peptides like ADan, Abri or also Aβ-related peptides.

The levels of Aβ(N3pGlu-42) in heterozygous tgN3E-42 mice were significantly elevated after cross-breeding with mice transgenic for murine glutaminyl cyclase (QC), showing that QC, in principle, can catalyze the conversion of glutamate to pyroglutamate in vivo. These data indicate that increased intraneuronal accumulation of Aβ(N3pGlu-42) is sufficient to produce degeneration and ataxia and demonstrate that a mouse model can be established for neurodegeneration caused by pyroglutamate formation.

The present invention further comprises compositions and methods for screening of biologically active agents that modulate Aβ-peptide-related diseases including, but not limited to, Mild Cognitive Impairment (MCI), Alzheimer's Disease (Aβ), cerebral amyloid angiopathy, Lewy body dementia, neurodegeneration in Down Syndrome, hereditary cerebral hemorrhage with amyloidosis (Dutch type), Familial Danish Dementia, Familial British Dementia, ulcer disease and gastric cancer with or w/o *Helicobacter pylori* infections, pathogenic psychotic conditions, schizophrenia, infertility, neoplasia, inflammatory host responses, cancer, psoriasis, rheumatoid arthritis, atherosclerosis, restenosis, lung fibrosis, liver fibrosis, renal fibrosis, Acquired Immune Deficiency Syndrome, graft rejection, Chorea Huntington (HD), impaired humoral and cell-mediated immune responses, leukocyte adhesion and migration processes in the endothelium, impaired food intake, sleep-wakefulness, impaired homeostatic regulation of energy metabolism, impaired autonomic function, impaired hormonal balance and impaired regulation of body fluids and the Guam Parkinson-Dementia complex. Another aspect of the present invention comprises methods and compositions for screening for QC and/or QPCTL inhibitors.

Additionally, the present invention comprises methods and compositions for the treatment and/or prevention of Aβ-peptide-related diseases, particularly methods and compositions that inhibit Aβ-peptide-related toxicity and/or aggregation propensity.

Accordingly, it is an object of the invention to provide a transgenic animal, which overexpresses a certain Aβ-peptide.

It is another object of the invention to provide DNA constructs encoding a certain Aβ-peptide.

It is an additional object of the invention to provide DNA constructs encoding Aβ-peptides linked to a promoter.

It is a further object of the invention to provide a non-human transgenic animal model system.

It is an additional object of the invention to provide a non-human transgenic animal model system to study the in vivo and in vitro regulation and effects of Aβ-peptides in specific tissue types.

It is a further object of the invention to provide the methodology for a generation of a transgenic animal, which overexpresses the amyloid peptides ADan and ABri.

In addition, it was shown earlier by inhibition studies that human and murine QC are metal-dependent transferases. QC apoenzyme could be reactivated most efficiently by zinc ions, and the metal-binding motif of zinc-dependent aminopeptidases is also present in human QC. Compounds interacting with the active-site bound metal are potent inhibitors.

In was shown earlier that recombinant human QC as well as QC-activity from brain extracts catalyze both, the N-terminal glutaminyl as well as glutamyl cyclization. Most striking is the finding, that QC-catalyzed $Glu^1$-conversion is favored around pH 6.0 while $Gln^1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of e.g. Alzheimer's disease.

By administering effectors of Aβ-peptide activity to a mammal it can be possible to prevent or alleviate or treat conditions selected from Mild Cognitive Impairment (MCI), Alzheimer's Disease (AD), cerebral amyloid angiopathy, Lewy body dementia, neurodegeneration in Down Syndrome, hereditary cerebral hemorrhage with amyloidosis (Dutch type), Familial Danish Dementia, Familial British Dementia, ulcer disease and gastric cancer with or w/o *Helicobacter pylori* infections, pathogenic psychotic conditions, schizophrenia, infertility, neoplasia, inflammatory host responses, cancer, psoriasis, rheumatoid arthritis, atherosclerosis, restenosis, lung fibrosis, liver fibrosis, renal fibrosis, Acquired Immune Deficiency Syndrome, graft rejection, Chorea Huntington (HD), impaired humoral and cell-mediated immune responses, leukocyte adhesion and migration processes in the endothelium, impaired food intake, sleep-wakefulness, impaired homeostatic regulation of energy metabolism, impaired autonomic function, impaired hormonal balance and impaired regulation of body fluids.

Further, by administration of effectors of Aβ-peptide activity to a mammal it can be possible to stimulate gastrointestinal tract cell proliferation, preferably proliferation of gastric mucosal cells, epithelial cells, acute acid secretion and the differentiation of acid producing parietal cells and histamine-secreting enterochromaffin-like cells.

Furthermore, by administration of effectors of Aβ-peptide activity to a mammal it can be possible to suppress the proliferation of myeloid progenitor cells.

In addition, administration of Aβ-peptide inhibitors can lead to suppression of male fertility.

The present invention provides pharmaceutical compositions for parenteral, enteral or oral administration, comprising at least one effector of Aβ-peptide optionally in combination with customary carriers and/or excipients.

Other objects and features will be in part apparent and in part pointed out hereinafter.

BRIEF DESCRIPTION OF THE DRAWINGS

Further understanding of these and other aspects of the present invention will be gained by reference to the figures described below. Those of skill in the art will understand that the drawings, described below, are for illustrative purposes only. The drawings are not intended to limit the scope of the present teachings in any way.

Figure 1:
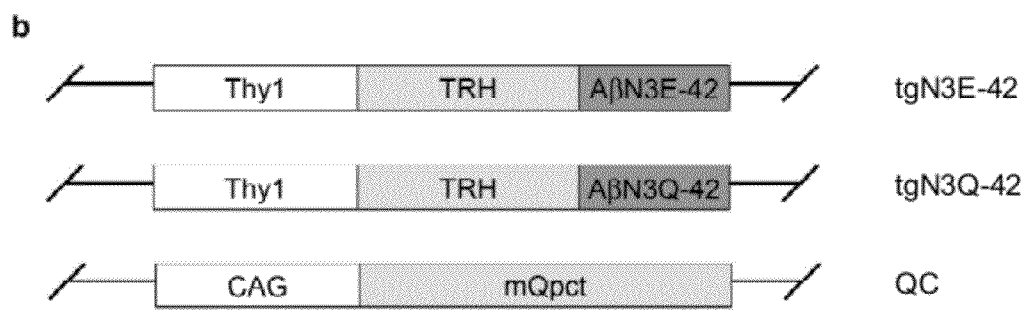
FIG. 1 Constructs to generate the transgenic mice and expression profile in brain at 2 months of age. (a). AβN1-42 starts at position 1 with aspartate (D), AβN3E-42 at position 3 with glutamate (E), and AβN3Q-42 with glutamine (Q). Both N-truncated AβN3E-42 and AβN3Q-42 peptides can be converted by QC activity to generate AβN3(pE)-42. (b) Schematic drawing of the transgenic vectors. TgN3E-42 and tgN3Q-42 transgenic mice expressing either Aβ(N3E-42) or Aβ(N3Q-42) under the control of the Thy1 promoter and are fused to the prepro-peptide of murine TRH (amino acids: methionine1-arginine-76). QC transgenic mice express the murine QC minigene (mQPCT) under the control of the CAG promoter. ELISA analysis of Aβ(x-42) and Aβ(N3pGlu-42) in brain hemisphere lysates of WT (N=6), QC(N=6), tgN3E-42 (N=9), tgN3E-42/QC(N=9), and tgN3Q-42 (N=4) mice (c-e). (c) Significant increase in Aβ (x-42) levels was found in tgN3E-42 mice, compared to WT controls (P<0.0001). TgN3Q-42 showed the highest levels of Aβ(x-42) compared to tgN3E-42 (P<0.00001, unpaired t-test) and tgN3E-42-QC double-transgenic mice (P<0.00001, unpaired t-test). (d) tgN3E-42-QC double-transgenic mice had increased levels compared to tgN3E-42 expression alone. tgN3Q-42 mice showed the highest levels of Aβ(N3pGlu-42) compared to tgN3E-42 (P<0.00001, unpaired t-test) and tgN3E-42-QC double-transgenic (P<0.00001, unpaired t-test) mice. (e) The same was true for the ratios of Aβ(N3pGlu-42) to total Aβ(x-42). All mice were 2 months of age. Values are given as means±s.e.m., *P<0.05. ***P<0.001.
Figure 1:
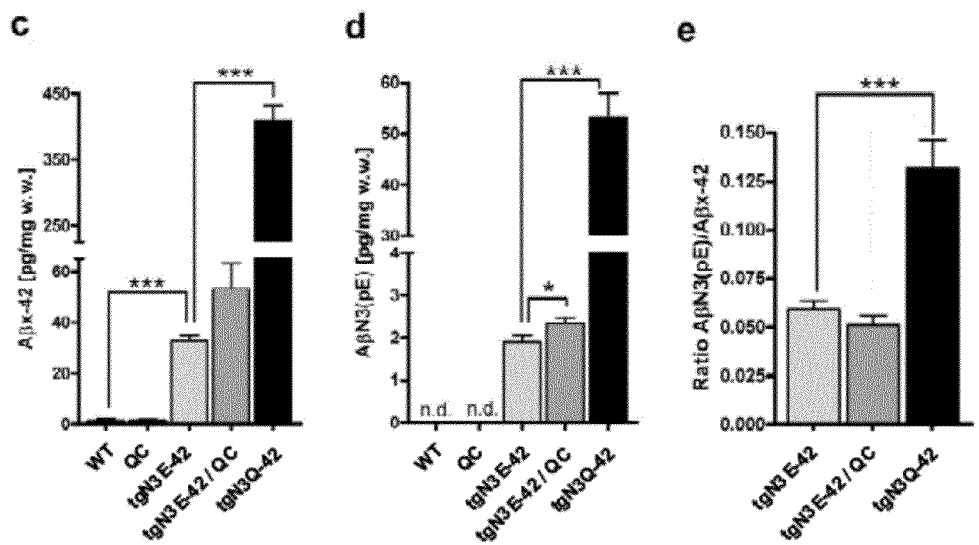

Other objects, advantages and features of the invention will become apparent upon consideration of the following detailed description.

DETAILED DESCRIPTION OF THE PRESENTLY PREFERRED EMBODIMENTS

The present invention comprises methods and compositions for the generation of a transgenic animal model for the study of Aβ-peptide-related diseases and the transgenic non-human animal per se. The present invention specifically comprises methods and compositions for generating transgenic animal models that overexpress Aβ-peptides and the transgenic non-human animal per se. The present invention further comprises methods and compositions for testing Aβ-peptide inhibitors and methods of prevention/treatment and pharmaceutical compositions with Aβ-peptide inhibitors.

The present invention also provides a new method for the treatment of Mild Cognitive Impairment (MCI), Alzheimer's disease, Familial Danish Dementia (FDD), Familial British Dementia (FBD) and neurodegeneration in Down Syndrome. The N-termini of the amyloid β-peptides deposited in Alzheimer's disease and Down syndrome brain as well as the amyloid peptides ADan and ABri deposited in Familial Danish Dementia and Familial British Dementia, bear pyroglutamic acid. The pGlu formation at the N-termini of ADan in FDD and ABri in FBD and Aβ in Alzheimer's disease and Down's Syndrome has been shown to be an important event in the development and progression of the respective disease, since the modified amyloid β-peptides, ADan and ABri show an enhanced tendency to amyloid aggregation and toxicity, likely worsening the onset and progression of the diseases. (Russo, C. et al. 2002 J Neurochem 82, 1480-1489; Ghiso, J. et al. 2001 Amyloid 8, 277-284).

DEFINITIONS

The following definitions and methods are provided to better define the present invention and to guide those of ordinary skill in the art in the practice of the present invention. Unless otherwise noted, terms are to be understood according to conventional usage by those of ordinary skill in the relevant art.

The term "transgene" means a segment of DNA that has been incorporated into a host genome or is capable of autonomous replication in a host cell and is capable of causing the expression of one or more cellular products. Exemplary transgenes will provide the host cell, or animals developed therefrom, with a novel phenotype relative to the corresponding non-transformed cell or animal.

The term "transgenic animal" means a non-human animal, usually a mammal, having a non-endogenous nucleic acid sequence present as an extrachromosomal element in a portion of its cells or stably integrated into its germ line DNA.

The term "construct" means a recombinant nucleic acid, generally recombinant DNA, that has been generated for the purpose of the expression of a specific nucleotide sequence(s), or is to be used in the construction of other recombinant nucleotide sequences. The recombinant nucleic acid can encode e.g. a chimeric or humanized polypeptide.

Polypeptide here pertains to all possible amino acid sequences comprising more than 10 amino acids.

The term "operably linked" means that a DNA sequence and a regulatory sequence(s) are connected in such a way as to permit gene expression when the appropriate molecules (e.g., transcriptional activator proteins) are bound to the regulatory sequence(s).

The term "operatively inserted" means that a nucleotide sequence of interest is positioned adjacent a nucleotide sequence that directs transcription and translation of the introduced nucleotide sequence of interest.

Transgenes

The Aβ-peptide polynucleotides comprising the transgene of the present invention include Aβ-peptide cDNA and shall also include modified Aβ-peptide cDNA. As used herein, a "modification" of a nucleic acid can include one or several nucleotide additions, deletions, or substitutions with respect to a reference sequence. A modification of a nucleic acid can include substitutions that do not change the encoded amino acid sequence due to the degeneracy of the genetic code, or which result in a conservative substitution. Such modifications can correspond to variations that are made deliberately, such as the addition of a Poly A tail, or variations which occur as mutations during nucleic acid replication.

As employed herein, the term "substantially the same nucleotide sequence" refers to DNA having sufficient identity to the reference polynucleotide, such that it will hybridize to the reference nucleotide under moderately stringent, or higher stringency, hybridization conditions. DNA having "substantially the same nucleotide sequence" as the reference nucleotide sequence, can have an identity ranging from at least 60% to at least 95% with respect to the reference nucleotide sequence.

The phrase "moderately stringent hybridization" refers to conditions that permit a target-nucleic acid to bind a complementary nucleic acid. The hybridized nucleic acids will generally have an identity within a range of at least about 60% to at least about 95%. Moderately stringent conditions are conditions equivalent to hybridization in 50% formamide, 5×Denhart's solution, 5× saline sodium phosphate EDTA buffer (SSPE), 0.2% SDS (Aldrich) at about 42° C., followed by washing in 0.2×SSPE, 0.2% SDS (Aldrich), at about 42° C.

High stringency hybridization refers to conditions that permit hybridization of only those nucleic acid sequences that form stable hybrids in 0.018M NaCl at about 65° C., for example, if a hybrid is not stable in 0.018M NaCl at about 65° C., it will not be stable under high stringency conditions, as contemplated herein. High stringency conditions can be provided, for example, by hybridization in 50% formamide, 5× Denhart's solution, 5×SSPE, 0.2% SDS at about 42° C., followed by washing in 0.1×SSPE, and 0.1% SDS at about 65° C.

Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al. (Current Protocols in Molecular Biology (Supplement 47), John Wiley & Sons, New York (1999)).

The amino acid sequence encoded by the transgene of the present invention can be an Aβ-peptide sequence from a human or the Aβ-peptide homologue from any species, preferably from a murine species. The amino acid sequence encoded by the transgene of the present invention can also be a fragment of the Aβ-peptide amino acid sequence so long as the fragment retains some or all of the function of the full-length Aβ-peptide sequence. The sequence may also be a modified Aβ-peptide sequence. Individual substitutions, deletions or additions, which alter, add or delete a single amino acid or a small percentage of amino acids (typically less than 10%, more typically less than 5%, and still more typically less than 1%.) A "modification" of the amino acid sequence encompasses conservative substitutions of the amino acid sequence. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Other minor modifications are included within the sequence so long as the polypeptide retains some or all of the structural and/or functional characteristics of an Aβ-peptide polypeptide. Exemplary structural or functional characteristics include sequence identity or substantial similarity, antibody reactivity, the presence of conserved structural domains such as RNA binding domains or acidic domains.

DNA Constructs and Vectors

The invention further provides a DNA construct comprising the Aβ-peptide transgene as described above. As used herein, the term "DNA construct" refers to a specific arrangement of genetic elements in a DNA molecule. In addition to human Aβ-peptide, or mutant forms thereof, the invention also provides a DNA construct using polypeptides from other species as well as mutant Aβ-peptide from non-human mammals.

If desired, the DNA constructs can be engineered to be operatively linked to appropriate expression elements such as promoters or enhancers to allow expression of a genetic element in the DNA construct in an appropriate cell or tissue. The use of the expression control mechanisms allows for the targeted delivery and expression of the gene of interest. For example, the constructs of the present invention may be constructed using an expression cassette which includes in the 5'-3' direction of transcription, a transcriptional and translational initiation region associated with gene expression in brain tissue, DNA encoding a mutant or wild-type Aβ-peptide and a transcriptional and translational termination region functional in the host animal. One or more introns also can be present. The transcriptional initiation region can be endogenous to the host animal or foreign or exogenous to the host animal.

The DNA constructs described herein may be incorporated into vectors for propagation or transfection into appropriate cells to generate Aβ-peptide overexpressing mutant non-human mammals and are also comprised by the present invention. One skilled in the art can select a vector based on desired properties, for example, for production of a vector in a particular cell such as a mammalian cell or a bacterial cell.

Vectors can contain a regulatory element that provides tissue specific or inducible expression of an operatively linked nucleic acid. One skilled in the art can readily determine an appropriate tissue-specific promoter or enhancer that allows expression of Aβ-peptides in a desired tissue. It should be noted that tissue-specific expression as described herein does not require a complete absence of expression in tissues other than the preferred tissue. Instead, "cell-specific" or "tissue-specific" expression refers to a majority of the expression of a particular gene of interest in the preferred cell type or tissue.

Any of a variety of inducible promoters or enhancers can also be included in the vector for expression of a Aβ-peptide or nucleic acid that can be regulated. Such inducible systems, include, for example, tetracycline inducible System (Gossen & Bizard, Proc. Natl. Acad. Sci. USA, 89:5547-5551 (1992); Gossen et al., Science, 268:17664769 (1995); Clontech, Palo Alto, Calif.); metallothionein promoter induced by heavy metals; insect steroid hormone responsive to ecdysone or related steroids such as muristerone (No et al., Proc. Natl. Acad. Sci. USA, 93:3346-3351 (1996); Yao et al., Nature, 366:476-479 (1993); Invitrogen, Carlsbad, Calif.); mouse mammary tumor virus (MMTV) induced by steroids such as glucocorticoid and estrogen (Lee et al., Nature, 294:228-232 (1981); and heat shock promoters inducible by temperature changes; the rat neuron specific enolase gene promoter (Forss-Petter, et al., Neuron 5; 197-197 (1990)); the human β-actin gene promoter (Ray, et al., Genes and Development (1991) 5:2265-2273); the human platelet derived growth factor B (PDGF-B) chain gene promoter (Sasahara, et al., Cell (1991) 64:217-227); the rat sodium channel gene promoter (Maue, et al., Neuron (1990) 4:223-231); the human copper-zinc superoxide dismutase gene promoter (Ceballos-Picot, et al., Brain Res. (1991) 552:198-214); and promoters for members of the mammalian POU-domain regulatory gene family (Xi et al., (1989) Nature 340:35-42).

Regulatory elements, including promoters or enhancers, can be constitutive or regulated, depending upon the nature of the regulation, and can be regulated in a variety of tissues, or one or a few specific tissues. The regulatory sequences or regulatory elements are operatively linked to one of the polynucleotide sequences of the invention such that the physical and functional relationship between the polynucleotide sequence and the regulatory sequence allows transcription of the polynucleotide sequence. Vectors useful for expression in eukaryotic cells can include, for example, regulatory elements including the CAG promoter, the SV40 early promoter, the cytomegalovirus (CMV) promoter, the mouse mammary tumor virus (MMTV) steroid-inducible promoter, Pgtf, Moloney marine leukemia virus (MMLV) promoter, thy-1 promoter and the like.

If desired, the vector can contain a selectable marker. As used herein, a "selectable marker" refers to a genetic element that provides a selectable phenotype to a cell in which the selectable marker has been introduced. A selectable marker is generally a gene whose gene product provides resistance to an agent that inhibits cell growth or kills a cell. A variety of selectable markers can be used in the DNA constructs of the invention, including, for example, Neo, Hyg, hisD, Gpt and Ble genes, as described, for example in Ausubel et al. (Current Protocols in Molecular Biology (Supplement 47), John Wiley & Sons, New York (1999)) and U.S. Pat. No. 5,981,830. Drugs useful for selecting for the presence of a selectable marker include, for example, G418 for Neo, hygromycin for Hyg, histidinol for hisD, xanthine for Gpt, and bleomycin for Ble (see Ausubel et al, supra, (1999); U.S. Pat. No. 5,981, 830). DNA constructs of the invention can incorporate a positive selectable marker, a negative selectable marker, or both (see, for example, U.S. Pat. No. 5,981,830).

Preferred according to the present invention are the following DNA constructs and fusion proteins: mTRH-Aβ(N3E-42), mTRH-Aβ(N3Q-42).

A preferred cloning vector is pUC18 containing the Thy-1 sequence.

Non-Human Transgenic Animals

The invention primarily provides a non-human transgenic animal whose genome comprises a transgene encoding an Aβ-peptide. The DNA fragment can be integrated into the genome of a transgenic animal by any method known to those skilled in the art. The DNA molecule containing the desired gene sequence can be introduced into pluripotent cells, such as ES cells, by any method that will permit the introduced molecule to undergo recombination at its regions of homology. Techniques that can be used include, but are not limited to, calcium phosphate/DNA co-precipitates, microinjection of DNA into the nucleus, electroporation, bacterial protoplast fusion with intact cells, transfection, and polycations, (e.g., polybrene, polyornithine, etc.) The DNA can be single or double stranded DNA, linear or circular. (See for example, Hogan et al., Manipulating the Mouse Embryo: A Laboratory Manual Cold Spring Harbor Laboratory (1986); Hogan et al., Manipulating the Mouse Embryo: A Laboratory Manual, second ed., Cold Spring Harbor Laboratory (1994), U.S. Pat. Nos. 5,602,299; 5,175,384; 6,066,778; 4,873,191 and 6,037, 521; retrovirus mediated gene transfer into germ lines (Van der Putten et al., Proc. Natl. Acad. Sci. USA 82:6148-6152 (1985)); gene targeting in embryonic stem cells (Thompson et al., Cell 56:313-321 (1989)); electroporation of embryos (Lo, Mol Cell. Biol. 3:1803-1814 (1983)); and sperm-mediated gene transfer (Lavitrano et al., Cell 57:717-723 (1989)).

For example, the zygote is a good target for microinjection, and methods of microinjecting zygotes are well known (see U.S. Pat. No. 4,873,191).

Embryonal cells at various developmental stages can also be used to introduce transgenes for the production of transgenic animals. Different methods are used depending on the stage of development of the embryonal cell. Such transfected embryonic stem (ES) cells can thereafter colonize an embryo following their introduction into the blastocoele of a blastocyst-stage embryo and contribute to the germ line of the resulting chimeric animal (reviewed in Jaenisch, Science 240:1468-1474 (1988)). Prior to the introduction of transfected ES cells into the blastocoele, the transfected ES cells can be subjected to various selection protocols to enrich the proportion of ES cells that have integrated the transgene if the transgene provides a means for such selection. Alternatively, PCR can be used to screen for ES cells that have integrated the transgene.

In addition, retroviral infection can also be used to introduce transgenes into a non-human animal. The developing non-human embryo can be cultured in vitro to the blastocyst stage. During this time, the blastomeres can be targets for retroviral infection (Jaenisch, Proc. Natl. Acad. Sci. USA 73: 1260-1264 (1976)). Efficient infection of the blastomeres is obtained by enzymatic treatment to remove the zona pellucida (Hogan et al., supra, 1986). The viral vector system used to introduce the transgene is typically a replication-defective retrovirus carrying the transgene (Jahner et al., Proc. Natl. Acad. Sci. USA 82:6927-6931 (1985); Van der Putten et al., Proc. Natl. Acad. Sci. USA 82:6148-6152 (1985)). Transfection is easily and +efficiently obtained by culturing the blastomeres on a monolayer of virus-producing cells (Van der Putten, supra, 1985; Stewart et al., EMBO J. 6:383-388 (1987)). Alternatively, infection can be performed at a later stage. Virus or virus-producing cells can be injected into the blastocoele (Jahner D. et al., Nature 298:623-628 (1982)). Most of the founders will be mosaic for the transgene since incorporation occurs only in a subset of cells, which form the transgenic animal. Further, the founder can contain various retroviral insertions of the transgene at different positions in the genome, which generally will segregate in the offspring. In addition, transgenes may be introduced into the germline by intrauterine retroviral infection of the mid-gestation embryo (Jahner et al., supra, 1982). Additional means of using retroviruses or retroviral vectors to create transgenic animals known to those of skill in the art involves the microinjection of retroviral particles or mitomycin C-treated cells producing retrovirus into the perivitelline space of fertilized eggs or early embryos (WO 90/08832 (1990); Haskell and Bowen, Mal. Reprod. Dev. 40: 386 (1995)).

Any other technology to introduce transgenes into a non-human animal, e.g. the knock-in or the rescue technologies can also be used to solve the problem of the present invention. The knock-in technology is well known in the art as described e.g. in Casas et al. (2004) Am J Pathol 165, 1289-1300.

Once the founder animals are produced, they can be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic mice to produce mice homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene and the effects of expression.

The transgenic animals are screened and evaluated to select those animals having the phenotype of interest. Initial screening can be performed using, for example, Southern blot analysis or PCR techniques to analyze animal tissues to verify that integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and reverse transcriptase-PCR (rt-PCR). Samples of the suitable tissues can be evaluated immunocytochemically using antibodies specific for the transgene. The transgenic non-human mammals can be further characterized to identify those animals having a phenotype useful in methods of the invention. In particular, transgenic non-human mammals overexpressing the transgene (e.g. QPCT or QPCTL) can be screened using the methods disclosed herein. For example, tissue sections can be viewed under a fluorescent microscope for die present of fluorescence, indicating the presence of the reporter gene.

Another method to affect tissue specific expression of the Aβ-peptide is through the use of tissue-specific promoters. Non-limiting examples of suitable tissue-specific promoters include the albumin promoter (liver-specific; Pinkert et al., (1987) Genes Dev. 1:268-277); lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al., (1983) Cell 33:729-740; Queen and Baltimore (1983) Cell 33:741-748), neuron-specific promoters (e.g., the neurofilament promoter, the Thy-1 promoter or the Bri-protein promoter; Sturchler-Pierrat et al., (1997) Proc. Natl. Acad. Sci. USA 94:13287-13292, Byrne and Ruddle (1989) PNAS 86:5473-5477), pancreas-specific promoters (Edlund et al., (1985) Science 230:912-916), cardiac specific expression (alpha myosin heavy chain promoter, Subramaniam, A, Jones W K, Gulick J, Wert S, Neumann J, and Robbins J. Tissue-specific regulation of the alpha-myosin heavy chain gene promoter in transgenic mice. J Biol Chem 266: 24613-24620, 1991.), and mammary gland-specific promoters (e.g., milk whey promoter; U.S. Pat. No. 4,873,316 and European Application Publication No. 264, 166).

The invention further provides an isolated cell containing a DNA construct of the invention. The DNA construct can be introduced into a cell by any of the well-known transfection methods (Sambrook et al., Molecular Cloning: A Laboratory Manual, 2nd ed., Cold Spring Harbor Press, Plainview, N.Y. (1989); Ausubel et al., supra, (1999)). Alternatively, the cell can be obtained by isolating a cell from a mutant non-human mammal created as described herein. Thus, the invention provides a cell isolated from an Aβ-peptide mutant non-human mammal of the invention, in particular, an Aβ-peptide mutant mouse. The cells can be obtained from a homozygous Aβ-peptide mutant non-human mammal such as a mouse or a heterozygous Aβ-peptide mutant non-human mammal such as a mouse.

Effectors

Effectors, as that term is used herein, are defined as molecules that bind to enzymes and increase (promote) or decrease (inhibit) their activity in vitro and/or in vivo. Some enzymes have binding sites for molecules that affect their catalytic activity; a stimulator molecule is called an activator. Enzymes may even have multiple sites for recognizing more than one activator or inhibitor. Enzymes can detect concentrations of a variety of molecules and use that information to vary their own activities.

Effectors can modulate enzymatic activity because enzymes can assume both active and inactive conformations: activators are positive effectors, inhibitors are negative effectors. Effectors act not only at the active sites of enzymes, but also at regulatory sites, or allosteric sites, terms used to emphasize that the regulatory site is an element of the enzyme distinct from the catalytic site and to differentiate this form of regulation from competition between substrates and inhibitors at the catalytic site (Darnell, J., Lodish, H. and Baltimore, D. 1990, Molecular Cell Biology 2"d Edition, Scientific American Books, New York, page 63).

Enzyme Inhibitors

Reversible enzyme inhibitors: comprise competitive inhibitors, non-competitive reversible inhibitors, slow-binding or tight-binding inhibitors, transition state analogs and multisubstrate analogs.

Competitive inhibitors show non-covalent interactions with the enzyme and competition with substrate for the enzyme active site.

The principal mechanism of action of a reversible enzyme inhibitor and the definition of the dissociation constant can be visualized as follows:

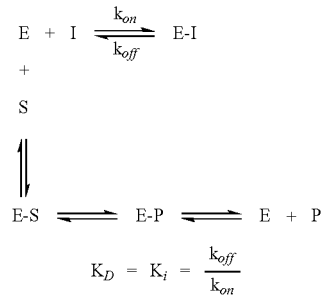

The formation of the enzyme-inhibitor [E-I] complex prevents binding of substrates, therefore the reaction cannot proceed to the normal physiological product, P. A larger inhibitor concentration [I] leads to larger [E-I], leaving less free enzyme to which the substrate can bind.

Non-competitive reversible inhibitors bind at a site other than active site (allosteric binding site) and cause a conformational change in the enzyme which decreases or stops catalytic activity.

Slow-binding or tight-binding inhibitors are competitive inhibitors where the equilibrium between inhibitor and enzyme is reached slowly, ($k_{on}$ is slow), possibly due to conformational changes that must occur in the enzyme or inhibitor; are often transition state analogs; and are effective at concentrations similar to the enzyme conc. (subnanomolar $K_D$ values) due to $k_{off}$ values being so low these types of inhibitors are "almost" irreversible.

Transition state analogs are competitive inhibitors which mimic the transition state of an enzyme catalyzed reaction. Enzyme catalysis occurs due to a lowering of the energy of the transition state, therefore, transition state binding is favored over substrate binding.

Multisubstrate Analogs

For a reaction involving two or more substrates, a competitive inhibitor or transition state analog can be designed which contains structural characteristics resembling two or more of the substrates.

Irreversible enzyme inhibitors: drive the equilibrium between the unbound enzyme and inhibitor and enzyme inhibitor complex (E+I<--->E-1) all the way to the right with a covalent bond (~100 kcal/mole), making the inhibition irreversible.

Affinity Labeling Agents

Active-site directed irreversible inhibitors (competitive irreversible inhibitor) are recognized by the enzyme (reversible, specific binding) followed by covalent bond formation, and are structurally similar to substrate, transition state or product allowing for specific interaction between drug and target enzyme, and contain reactive functional group (e.g. a nucleophile, —COCH$_2$Br) allowing for covalent bond formation.

The reaction scheme below describes an active-site directed reagent with its target enzyme where $K_D$ is the dissociation constant and $k_{inactivation}$ is the rate of covalent bond formation.

Mechanism-based enzyme inactivators (also called suicide inhibitors) are active-site directed reagents (unreactive) which binds to the enzyme active site where it is transformed to a reactive form (activated) by the enzyme's catalytic capabilities. Once activated, a covalent bond between the inhibitor and the enzyme is formed.

The reaction scheme below shows the mechanism of action of a mechanism based enzyme inactivator, where $K_D$ is the dissociation complex, $k_2$ is the rate of activation of the inhibitor once bound to the enzyme, $k_3$ is the rate of dissociation of the activated inhibitor, P, from the enzyme (product can still be reactive) from the enzyme and $k_4$ is the rate of covalent bond formation between the activated inhibitor and the enzyme.

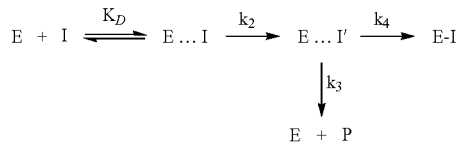

Inactivation (covalent bond formation, $k_4$) must occur prior to dissociation ($k_3$) otherwise the now reactive inhibitor is released into the environment. Partition ratio, $k_3/k_4$: ratio of released product to inactivation should be minimized for efficient inactivation of the system and minimal undesirable side reactions.

A large partition ratio (favors dissocation) leads to nonspecific reactions.

Uncompetitive enzyme inhibitors: From the definition of uncompetitive inhibitor (an inhibitor which binds only to ES complexes) the following equilibria can be written:

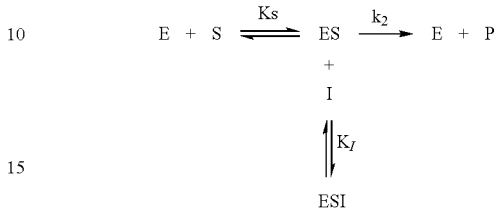

The ES complex dissociates the substrate with a dissociation constant equal to Ks, whereas the ESI complex does not dissociate it (i.e has a Ks value equal to zero). The $K_m$'s of Michaelis-Menten type enzymes are expected to be reduced. Increasing substrate concentration leads to increasing ESI concentration (a complex incapable of progressing to reaction products), therefore the inhibition can not be removed.

Preferred according to the present invention are competitive enzyme inhibitors.

Most preferred are competitive reversible enzyme inhibitors.

The terms "$k_i$" or "$K_I$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

Preferred according to the present invention are inhibitors of the enzymes exhibiting glutaminyl Cyclase activity. More preferably, the inhibitors of the enzymes exhibiting glutaminyl cyclase activity are competitive inhibitors. Even more preferred according to the present invention are competitive inhibitors of the enzymes exhibiting glutaminyl cyclase activity, which are small molecules. Especially preferred are small-molecule inhibitors of the enzymes exhibiting glutaminyl yclase activity, which bind to the active-site metal ion of glutaminyl cyclase.

The term "QC" as used herein comprises glutaminyl cyclase (QC, QPCT) and QC-like (QPCTL) enzymes. QC and QC-like enzymes have identical or similar enzymatic activity, further defined as QC activity. In this regard, QC-like enzymes can fundamentally differ in their molecular structure from QC.

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

Scheme 1: Cyclization of glutamine by QC

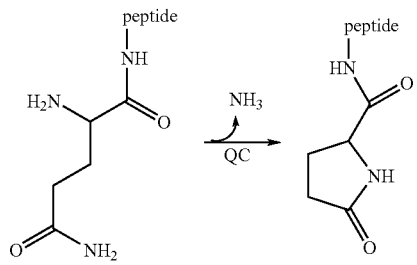

Scheme 2: Cyclization of L-homoglutamine by QC

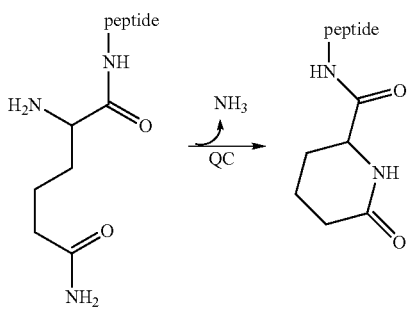

The term "EC" as used herein comprises the side activity of QC and QC-like enzymes as glutamate cyclase (EC), further defined as EC activity.

The term "EC activity" as used herein is defined as intramolecular cyclization of N-terminal glutamate residues into pyroglutamic acid (pGlu*) by QC. See therefore scheme 3.

Scheme 3: N-terminal cyclization of uncharged glutamyl peptides by QC (EC)

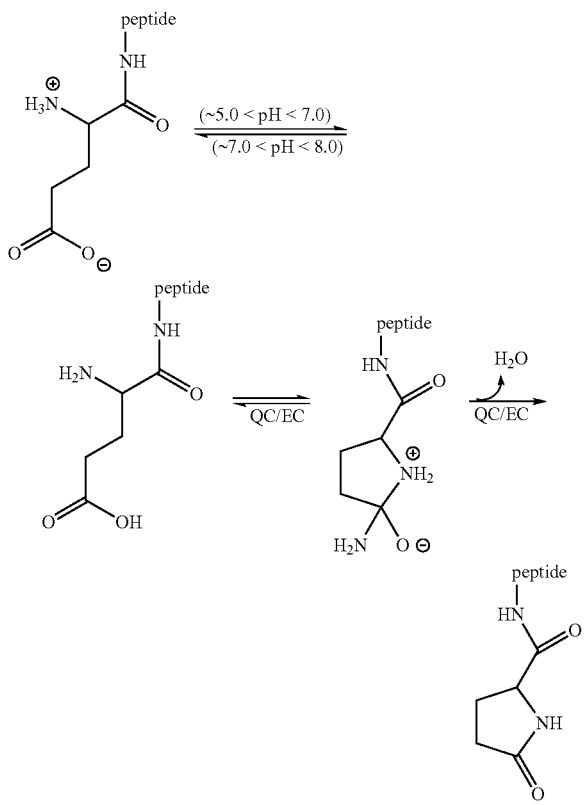

The term "QC-inhibitor" "glutaminyl cyclase inhibitor" is generally known to a person skilled in the art and means enzyme inhibitors, which inhibit the catalytic activity of glutaminyl cyclase (QC) or its glutamyl cyclase (EC) activity.

Potency of Glutaminyl Cyclase Inhibitors

In light of the correlation with QC inhibition, in preferred embodiments, the subject method and medical use utilize an agent with a $K_i$ for QC inhibition of 10 µM or less, more preferably of 1 µM or less, even more preferably of 0.1 µM or less or 0.01 µM or less, or most preferably 0.001 µM or less. Indeed, inhibitors with $K_i$ values in the lower micromolar, preferably the nanomolar and even more preferably the picomolar range are contemplated. Thus, while the active agents are described herein, for convience, as "QC inhibitors", it will be understood that such nomenclature is not intending to limit the subject of the invention to a particular mechanism of action.

Molecular Weight of QC Inhibitors

In general, the QC inhibitors of the subject method or medical use will be small molecules, e.g., with molecular weights of 1000 g/mole or less, 500 g/mole or less, preferably of 400 g/mole or less, and even more preferably of 350 g/mole or less and even of 300 g/mole or less.

Peptides

If peptides or amino acids are mentioned in the present invention, each amino acid residue is represented by a one-letter or a three-letter designation, corresponding to the trivial name of the amino acid, in accordance with the following conventional list:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The term "Aβ-peptide" as used herein refers to Aβ-peptides selected from Aβ3E-42 of SEQ ID No: 1, AβN3Q-42 of SEQ ID No: 2, Aβ(N3pGlu-42), Aβ3E-40 of SEQ ID No: 3, AβN3Q-40 of SEQ ID No: 4 and Aβ(N3pGlu-42).

The term "Aβ-peptide-related disease" as used herein refers to all those diseases, disorders or conditions that are characterized and/or mediated by Aβ-peptide.

Assays and Identification of Therapeutic Agents

The methods and compositions of the present invention are particularly useful in the evaluation of effectors of Aβ-peptide and for the development of drugs and therapeutic agents for the treatment and prevention of amyloid-associated diseases such as Mild Cognitive Impairment, Alzheimer's disease, neurodegeneration in Down Syndrome, Familial Danish Dementia and Familial British Dementia.

The transgenic animal or the cells of the transgenic animal of the invention can be used in a variety of screening assays. For example, any of a variety of potential agents suspected of affecting Aβ-peptide accumulation, as well as the appropriate antagonists and blocking therapeutic agents, can be screened by administration to the transgenic animal and assessing the effect of these agents upon the function and phenotype of the cells and on the (neurological) phenotype of the transgenic animals.

Behavioural studies may also be used to test potential therapeutic agents, such as those studies designed to assess motor skills, learning and memory deficits. An example of such a test is the Morris Water maze (Morris (1981) Learn Motivat 12:239-260). Additionally, behavioral studies may include evaluations of locomotor activity such as with the rotor-rod and the open field.

The methods of the invention can advantageously use cells isolated from a homozygous or heterozygous Aβ-peptide mutant non-human mammal, to study amyloid accumulation as well as to test potential therapeutic compounds. The methods of the invention can also be used with cells expressing Aβ-peptide such as a transfected cell line.

A cell overexpressing Aβ-peptide can be used in an in vitro method to screen compounds as potential therapeutic agents for treating Aβ associated disease. In such a method, a compound is contacted with a cell overexpressing Aβ-peptide, a transfected cell or a cell derived from a Aβ-peptide mutant non-human animal, and screened for alterations in a phenotype associated with expression of Aβ-peptide. The changes in Aβ production in the cellular assay and the transgenic animal can be assessed by methods well known to those skilled in the art.

An Aβ-fusion polypeptide such as Aβ-peptide can be particularly useful for such screening methods since the expression of Aβ-peptide can be monitored by fluorescence intensity. Other exemplary fusion polypeptides include other fluorescent proteins, or modifications thereof, glutathione S transferase (GST), maltose binding protein, poly His, FLAG, and the like, or any type of epitope tag. Such fusion polypeptides can be detected, for example, using antibodies specific to the fusion polypeptides. The fusion polypeptides can be an entire polypeptide or a functional portion thereof so long as the functional portion retains desired properties, for example, antibody binding activity or fluorescence activity.

The invention further provides a method of identifying a potential therapeutic agent for use in treating the diseases as mentioned above. The method includes the steps of contacting a cell containing a DNA construct comprising polynucleotides encoding an Aβ-peptide with a compound and screening the cell for decreased Aβ-peptide production, thereby identifying a potential therapeutic agent for use in treating Aβ-peptide-related diseases. The cell can be isolated from a transgenic non-human mammal having nucleated cells containing the Aβ-peptide DNA construct. Alternatively, the cell can contain a DNA construct comprising a nucleic acid encoding a green fluorescent protein fusion, or other fusion polypeptide, with an Aβ-peptide.

Additionally, cells expressing an Aβ-peptide can be used in a preliminary screen to identify compounds as potential therapeutic agents having activity that alters a phenotype associated with Aβ-peptide expression. As with in vivo screens using Aβ-peptide mutant non-human mammals, an appropriate control cell can be used to compare the results of the screen. The effectiveness of compounds identified by an initial in vitro screen using cells expressing Aβ-peptide can be further tested in vivo using the invention Aβ-peptide mutant non-human mammals, if desired. Thus, the invention provides methods of screening a large number of compounds using a cell-based assay, for example, using high throughput screening, as well as methods of further testing compounds as therapeutic agents in an animal model of Aβ-related disorders.

QC is involved in the formation of pyroglutamic acid that favors the aggregation of amyloid β-peptides. Thus, an inhibition of QC leads to a prevention of the precipitation of the plaque-forming [pGlu$^3$]Aβ3-40/42/43 or [pGlu$^{11}$]Aβ11-40/42/43, causing the onset and progression of Alzheimer's disease and Down Syndrome, independently of the mechanism by which cyclization occurs.

Glutamate is found in positions 3, 11 and 22 of the amyloid β-peptide. Among them the mutation from glutamic acid (E) to glutamine (Q) in position 22 (corresponds to amino acid 693 of the amyloid precursor protein APP770, Swissprot entry: P05067) has been described as the so-called Dutch type cerebroarterial amyloidosis mutation.

The β-amyloid peptides with a pyroglutamic acid residue in position 3 and 11 have been described to be more cytotoxic and hydrophobic than Aβ1-40/4243 (Saido T. C. 2000 Medical Hypotheses 54(3): 427-429).

The multiple N-terminal variations can be generated by the β-secretase enzyme β-site amyloid precursor protein-cleaving enzyme (BACE) at different sites (Huse J. T. et al. 2002 Biol. Chem. 277 (18): 16278-16284), and/or by aminopeptidase processing.

There had been no experimental evidence supporting the enzymatic conversion of Glu$^1$-peptides into pGlu-peptides by an unknown glutamyl cyclase (EC) (Garden, R. W., Moroz, T. P., Gleeson, J. M., Floyd, P. D., Li, L. J., Rubakhin, S. S., and Sweedler, J. V. (1999) J Neurochem 72, 676-681; Hosoda R. et al. (1998) J Neuropathol Exp Neurol. 57, 1089-1095). No such enzyme activity had been identified, capable of cyclizing Glu$^1$-peptides, which are protonated N-terminally and possess a negatively charged Glu$^1$ γ-carboxylate moiety under mildly alkaline or neutral pH-conditions.

QC-activity against Gln$^1$-substrates is dramatically reduced below pH 7.0. In contrast, it appears that Glu$^1$-conversion can occur at acidic reaction conditions (e.g. Iwatsubo, T., Saido, T. C., Mann, D. M., Lee, V. M., and Trojanowski, J. Q. (1996) Am J Pathol 149, 1823-1830).

Earlier, it was investigated whether QC is able to recognize and to turnover amyloid-β derived peptides under mildly acidic conditions (WO 2004/098625). Therefore, the peptides [Gln$^3$]Aβ1-11a, Aβ3-11a, [Gln$^3$]Aβ3-11a, Aβ3-21a, [Gln$^3$]Aβ3-21a and [Gln$^3$]Aβ3-40 as potential substrates of the enzyme were synthesized and investigated. These sequences were chosen for mimicking natural N-terminally and C-terminally truncated [Glu$^3$]Aβ peptides and [Gln$^3$]Aβ peptides which could occur due to posttranslational Glu-amidation.

It was shown that papaya and human QC catalyze both glutaminyl and glutamyl cyclization. Apparently, the primary physiological function of QC is to finish hormone maturation in endocrine cells by glutamine cyclization prior or during the hormone secretion process. Such secretory vesicles are known to be acidic in pH. Thus, a side activity of the enzyme in the narrow pH-range from 5.0 to 7.0 could be its newly discovered glutamyl cyclase activity cyclizing also Glu-Aβ peptides. However, due to the much slower occurring Glu-cyclization compared to Gln-conversion, it is questionable whether the glutamyl cyclization plays a significant physiological role. In the pathology of neurodegenerative disorders, however, the glutamyl cyclization is of relevance.

Investigating the pH-dependency of this enzymatic reaction, it has been shown that the unprotonated N-terminus was essential for the cyclization of Gln$^1$-peptides and accordingly that the pKa-value of the substrate was identical to the pKa-value for QC-catalysis. Thus, QC stabilizes the intramolecular nucleophilic attack of the unprotonated α-amino moiety on the γ-carbonyl carbon.

In contrast to the monovalent charge present on N-terminal glutamine containing peptides, the N-terminal Glu-residue in Glu-containing peptides is predominantly bivalently charged at neutral pH. Glutamate exhibits pK$_a$-values of about 4.2 and 7.5 for the 7-carboxylic and for the α-amino moiety, respectively, i.e. at neutral pH and above, although the α-amino nitrogen is in part or fully unprotonated and nucleophilic, the γ-carboxylic group is unprotonated, and so exercising no electrophilic carbonyl activity. Hence, intramolecular cyclization is impossible.

However, in the pH-range of about 5.2-6.5, between their respective $pK_a$-values, the two functional groups are present both in non-ionized forms, in concentrations of about 1-10% (—$NH_2$) or 10-1% (—COOH) of total N-terminal Glu-containing peptide. As a result, over a mildly acidic pH-range species of N-terminal Glu-peptides are present which carry both groups uncharged, and, therefore, it is possible that QC could stabilize the intermediate of intramolecular cyclization into the pGlu-peptide, i.e. if the γ-carboxylic group is protonated, the carbonyl carbon is electrophilic enough to allow nucleophilic attack by the unprotonated α-amino group. At this pH the hydroxyl ion functions as a leaving group. These assumptions are corroborated by the pH-dependence data obtained for the QC catalyzed conversion of Glu-βNA. In contrast to glutamine conversion of Gln-βNA by QC, the pH-optimum of catalysis shifts to the acidic range around pH 6.0, i.e. the pH-range, in which substrate molecule species are simultaneously abundant carrying a protonated γ-carboxyl and unprotonated α-amino group. Furthermore, the kinetically determined pKa-value of 7.55+/−0.02 is in excellent agreement with that of the α-amino group of Glu-β3NA, determined by titration (7.57±0.05).

Physiologically, at pH 6.0 the second-order rate constant (or specificity constant, $k_{cat}/K_M$) of the QC-catalyzed glutamate cyclization might be in the range of $1*10^5-1*10^6$ fold slower than the one for glutamine cyclization. However, the nonenzymatic turnover of both model substrates Glu-βNA and Gln-βNA is negligible, being conform with the observed negligible pGlu-peptide formation. Hence, for the pGlu-formation by QC an acceleration of at least $10^8$ can be estimated from the ratio of the enzymatic versus non-enzymatic rate constants (comparing the second-order rate constants for the enzyme catalysis with the respective nonenzymatic cyclization first-order rate constants the catalytic proficiency factor is $10^9$-$10^{10}$ $M^{-1}$ for the Gln- and the Glu-conversion, respectively). The conclusion from these data is, that in vivo only an enzymatic path resulting pGlu-formations seems conceivable.

Since QC is highly abundant in the brain and taking into account the high turnover rate of 0.9 $min^{-1}$ recently found for the maturation of 30 μM of (Gln-)TRH-like peptide (Prokal, L., Prokai-Tatrai, K., Ouyang, X., Kim, H. S., Wu, W. M., Zharikova, A., and Bodor, N. (1999) J Med Chem 42, 4563-4571), one can predict a cyclization half-life of about 100 hours for an appropriate glutamate-substrate, if similar reaction conditions are provided. Moreover, given compartmentalization and localization of brain QC/EC in the secretory pathway, the actual in vivo enzyme and substrate concentrations and reaction conditions might be even more favorable for the enzymatic cyclization in the intact cell. And, if N-terminal Glu is transformed to Gln a much more rapid pGlu-formation mediated by QC could be expected. In vitro, both reactions were suppressed by applying inhibitors of QC/EC-activity.

In summary, it was shown that human QC, which is highly abundant in the brain, is likely a catalyst of the formation of the amyloidogenic pGlu-Aβ peptides from Glu-Aβ and Gln-Aβ precursors, which make up more than 50% of the plaque deposits found in Alzheimer's disease. These findings identify QC/EC as a player in senile plaque formation and thus as a novel drug target in the treatment of Alzheimer's disease, neurodegeneration in Down Sydrome, Famlilial Danish Dementia and Familial British Dementia.

Figure 4:
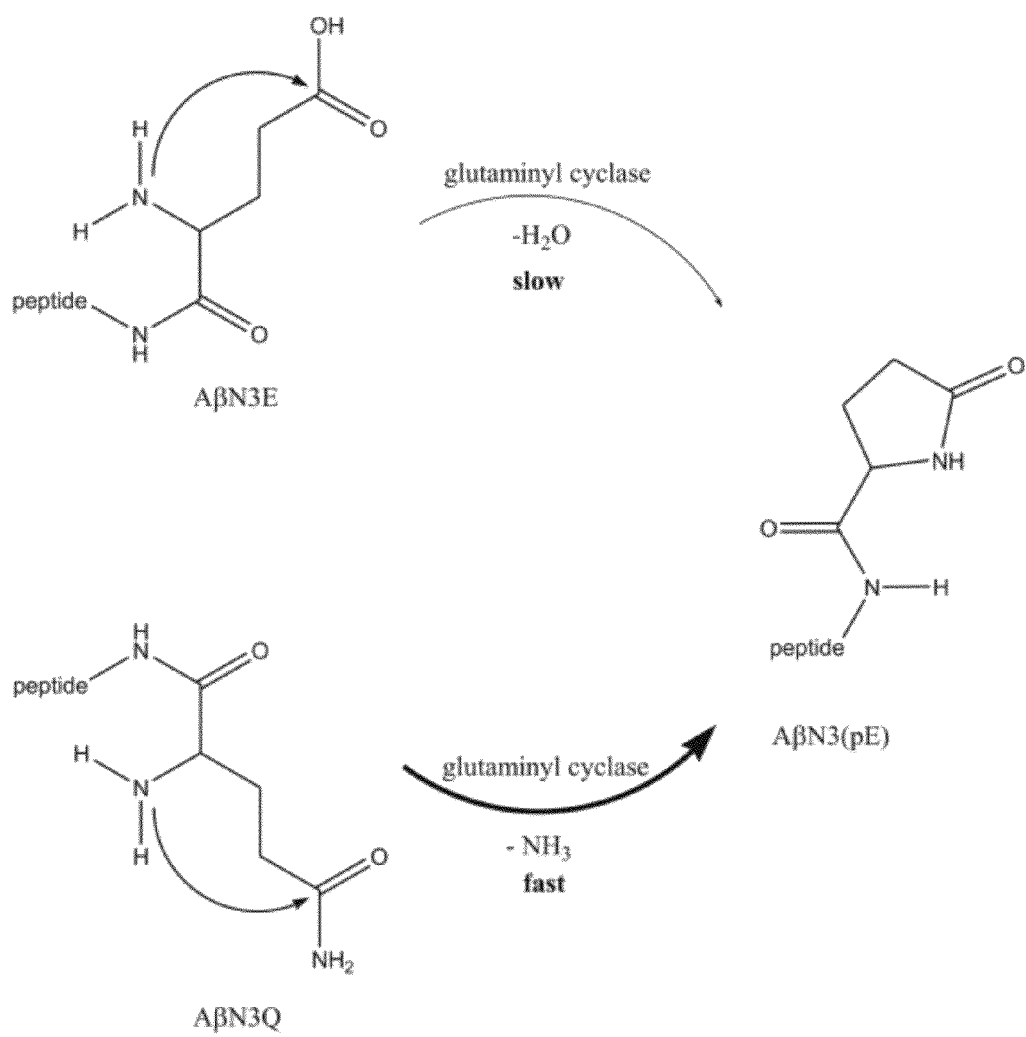
FIG. 4 Formation of Aβ starting at position 3 with pyroglutamate (AβN3(pE)) is catalyzed by glutaminyl cyclase (QC). The Aβ N-terminus starting with glutamate (AβN3E) or glutamine (AβN3Q) at position 3 can both serve as substrate for QC to generate AβN3(pE). It has been shown in vitro that conversion of pyroglutamate from N-terminal glutamate is slow, in contrast to pyroglutamate formation from glutamine which is a fast enzymatic process (Schilling, S., Hoffmann, T., Manhart, S., Hoffmann, M. & Demuth, H. U. Glutaminyl cyclases unfold glutamyl cyclase activity under mild acid conditions. FEBS Lett 563, 191-196 (2004)). This observation has also been verified in cell culture (Cynis, H., et al. Inhibition of glutaminyl cyclase alters pyroglutamate formation in mammalian cells. Biochim Biophys Acta 1764, 1618-1625 (2006)) and to occur in brain in vivo according to the present invention. Moreover, pharmacological inhibition of QC in cell culture leads to reduced AβN3(pE) levels (Cynis, H., et al. Inhibition of glutaminyl cyclase alters pyroglutamate formation in mammalian cells. Biochim Biophys Acta 1764, 1618-1625 (2006)).

Apart from Aβ starting with aspartate at position 1 (AβN1D), the majority of amyloid-β peptides in AD brain elicit a large heterogeneity at their N-terminus. As mentioned above, the dominant species starts at position 3 with pyroglutamate (AβN3(pGlu)). The pGlu residue originates from cyclization of N-terminal glutamate by the enzyme Glutaminyl Cyclase (QC). However, the conversion of N-glutamate residues into pGlu is rather slow, since QC naturally converts N-glutamine substrates (FIG. 1, and FIG. 4). Aβ(N3E-42) in tgN3E-42 and Aβ (N3Q-42) in tgN3Q-42 transgenic mice were expressed as fusion proteins with the pre-pro-sequence of murine thyrotropin-releasing hormone (mTRH) (FIG. 1 b), to be transported via the secretory pathway (Cynis, H., et al. Inhibition of glutaminyl cyclase alters pyroglutamate formation in mammalian cells, Biochim Biophys Acta 1764, 1618-1625 (2006)). ELISA quantification of Aβ(x-42) and Aβ(N3pGlu-42) of brain lysates of wildtype (WT), QC, tgN3E-42, tgN3E-42-QC double-transgenic, and tgN3Q-42 mice revealed significant differences (FIG. 1 c-e). While WT and QC transgenic mice generated low amounts of endogeneous Aβ(x-42) (WT, 1.29±0.91; QC, 1.36±0.61 pg/mg w.w.), tgN3E-42 mice elicited 32.57±2.27 Apx-42 (pg/mg w.w.), which was significantly higher compared to WT mice (P<0.0001). A trend of increased Aβ(x-42) was detected in tgN3E-42-QC double-transgenic mice with 53.29±10.13 (pg/mg w.w.). TgN3Q-42 showed a 12-fold elevation of Aβ(x-42) (410.2±21.52 pg/mg w.w) compared to tgN3E-42 (P<0.0001) and to tgN3E-42-QC double-transgenic mice (P<0.0001) (FIG. 1 c). In WT and QC mice AβN3(pGlu) was undetectable by ELISA (FIG. 1 d). Interestingly, there was a significant difference between tgN3E-42 (1.89±0.16 pg/mg w.w.), and tgN3E-42-QC double-transgenic mice (2.34±0.14 pg/mg w.w.). The tgN3E-42-QC double-transgenic mice elicited a 1.2-fold increased amount of Aβ(N3pGlu-42) (P<0.05). This substantiates recent findings of a QC-catalyzed N-glutamate formation (Cynis, H., et al. Inhibition of glutaminyl cyclase alters pyroglutamate formation in mammalian cells, Biochim Biophys Acta 1764, 1618-1625 (2006)). The tgN3Q-42 mice showed significantly higher Aβ(N3pGlu-42) levels (53.23±4.59 pg/mg w.w) than tgN3E-42 (28-fold more; P<0.0001). The ratios of Aβ (N3pGlu-42) to total Aβ(x-42) revealed similar results. TgN3E-42 mice had a ratio of 0.06±0.005 compared to tgN3E-42-QC double-transgenic mice with 0.05±0.005 (P=0.25). TgN3Q-42 mice showed a remarkable increased ratio of 0.11±0.015 (P<0.0001) (FIG. 1 e).

Figure 2:
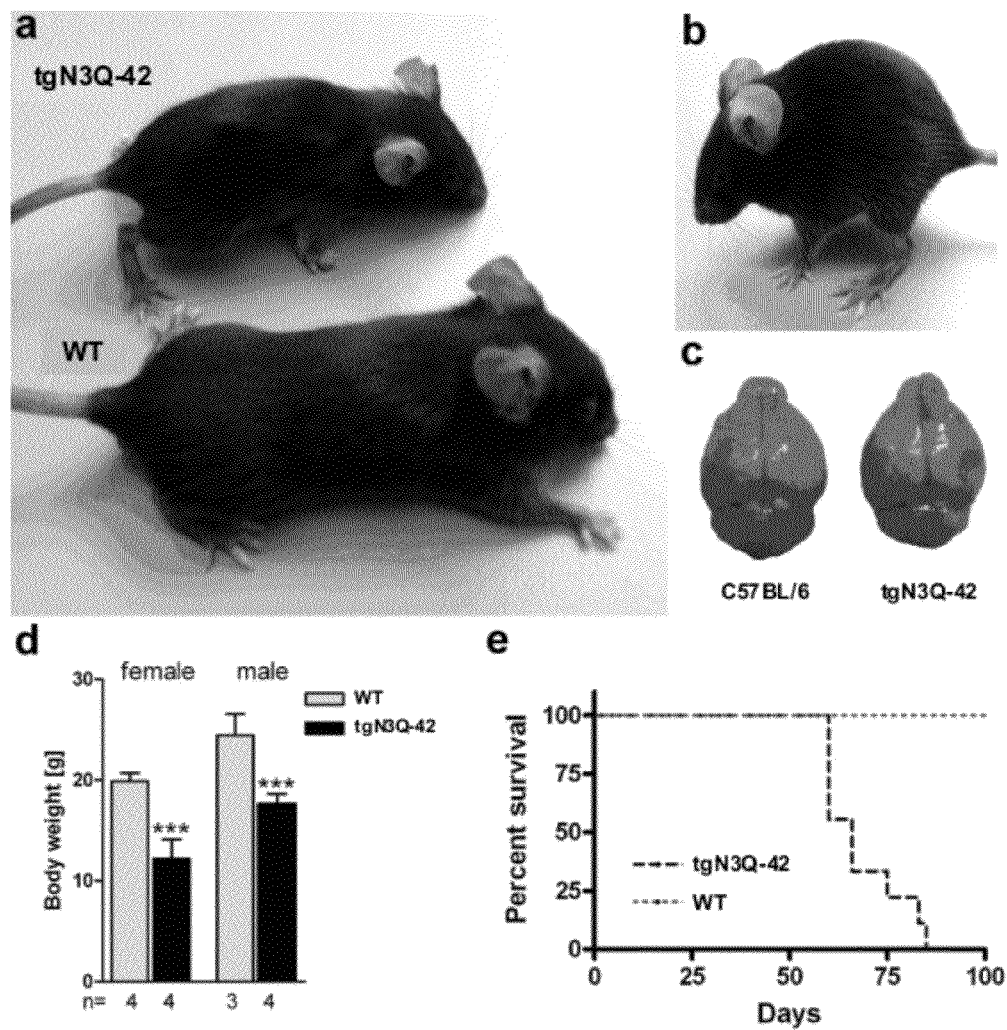
FIG. 2 Characterization of tgN3Q-42 transgenic mice. (a), (b) Picture of wildtype (WT) and tgN3Q-42 mice showing that tgN3Q-42 mice are generally smaller and that they display a crooked posture (b). (c) Macroscopic inspection of tgN3Q-42 brains revealed an atrophic cerebellum as compared to age-matched WT littermates (2 months-old mice). (d) Both, female and male tgN3Q-42 mice showed a reduced body weight compared to their age-matched WT littermates (2 months-old mice) (unpaired t-test). (e) tgN3Q-42 mice displayed a significantly reduced survival rate compared to WT littermates (P=0.0002; Logrank Test). Values are given as means±s.e.m., ***P<0.001.
Figure 3A:
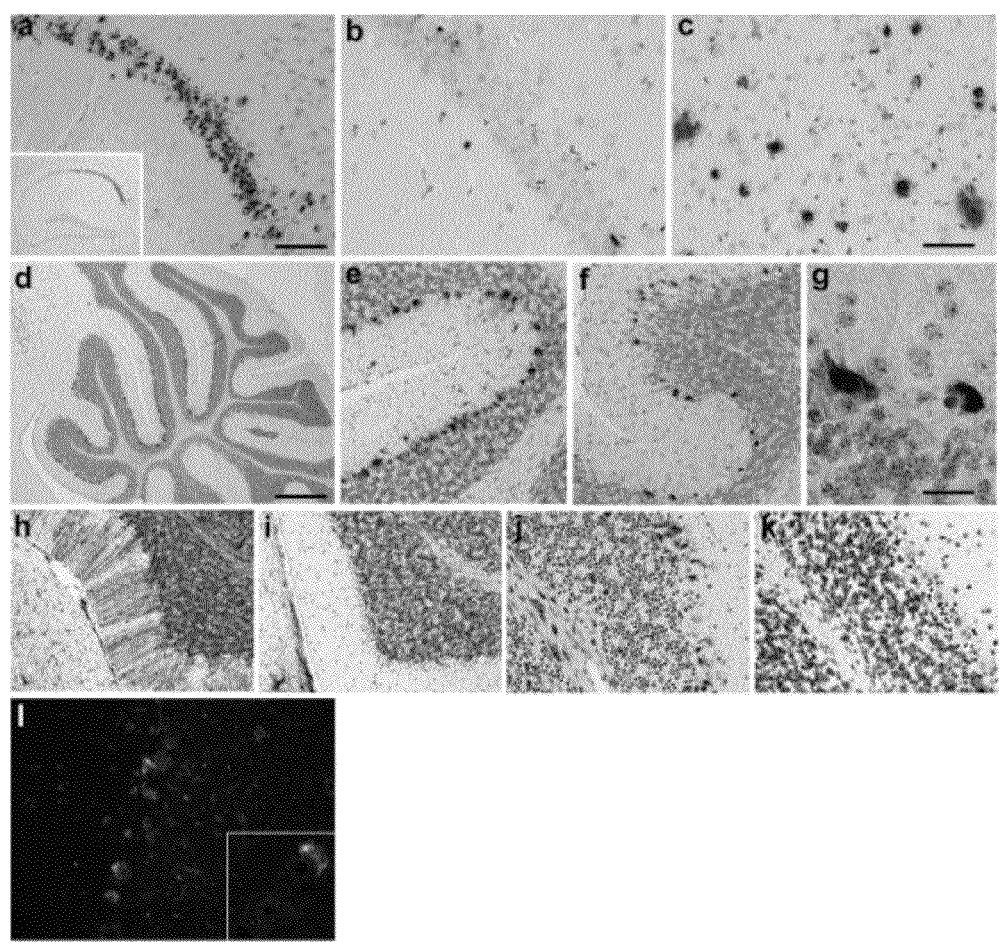
FIG. 3A Immunohistochemical staining of tgN3Q-42 mice. (a) Immunostaining with antibody 4G8 revealed strong A accumulation in the CA1 pyramidal layer of the hippocampus (inset shows a hippocampus overview at low magnification), whereas only a limited immunoreactivity was detected with an antibody against Aβ(N3pGlu) (b). (c) Extracellular diffuse A deposition in the thalamus shown by 4G8 staining. (d-e) Aβ staining (4G8) in the cerebellum is restricted to Purkinje cells. (f-g) Most Purkinje cells accumulated N-truncated Aβ starting with pyroglutamate as shown by an antibody against Aβ(N3pGlu). (h) GFAP staining revealed prominent staining of Bergmann glia in tgN3Q-42 mice, whereas wildtype animals (i) were consistently negative. The microglia marker Iba1 revealed microglia clusters surrounding Purkinje cells and in white matter tracts in tgN3Q-42 mice (j) but not in wildtype littermates (k). (l) Double-staining of Purkinje cells with 4G8 and against ubiquitin. Note abundant ubiquitin immunoreactivity, a marker for degeneration, in 4G8-positive Purkinje cells.
Figure 5:
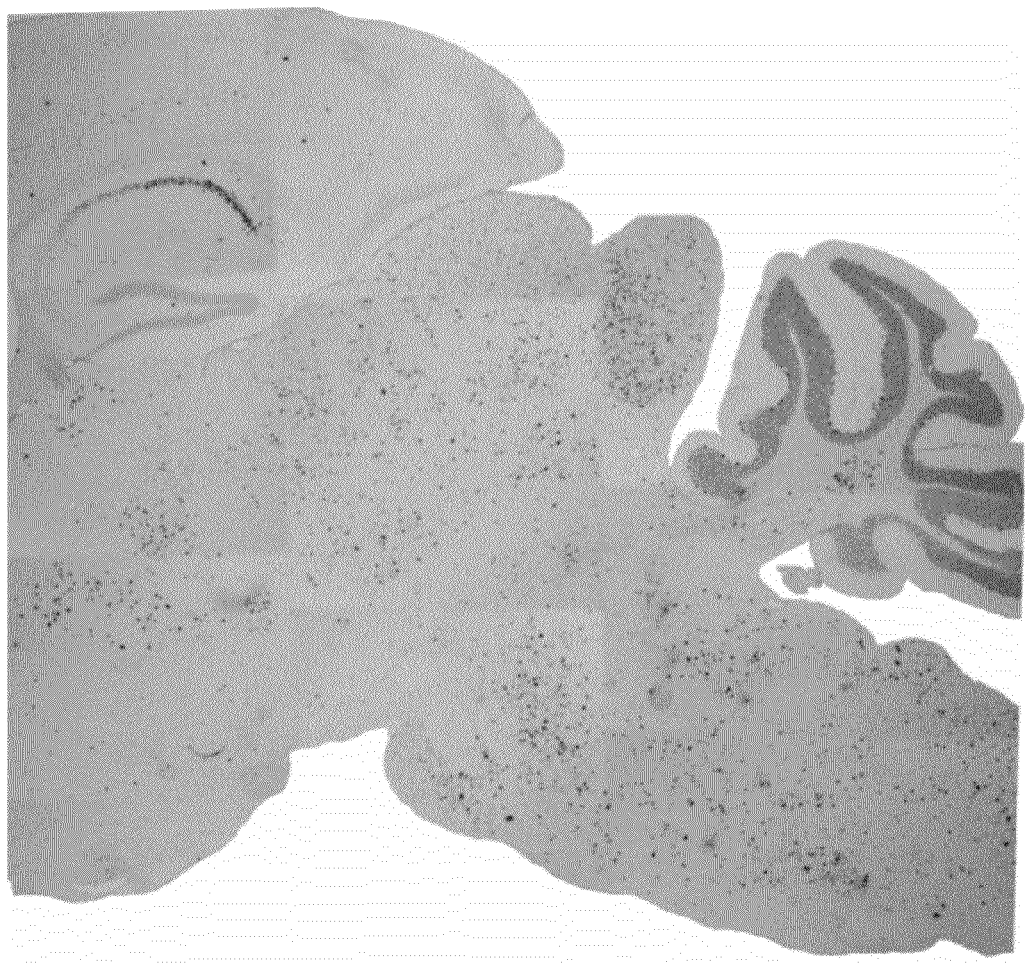
FIG. 5 illustrates an overview of immunohistochemical staining using Aβ antibody 4G8 in a 2 months-old tgN3Q-42 mouse brain section. Abundant staining is observed in hippocampal CA1 neurons, cerebellar Purkinje cells, cortex and subcortical areas.

Interestingly, tgN3Q-42 transgenic mice revealed obvious macroscopic abnormalities, including growth retardation, cerebellar atrophy, a premature death phenotype (FIG. 2) and a striking neurological deficiency characterized by loss of motor coordination and ataxia. The body weight at 2 months of age was significantly reduced in tgN3Q-42 mice (females, 12.20±0.95 g; males, 17.60±0.51 g), compared to controls (females, 19.90±0.40 g; males, 24.43±1.23 g; both significant: P<0.001). The neurological phenotype resembles that of mouse models with Purkinje cell degeneration. TgN3Q-42 brain sections showed strong immunoreactivity using antibody 4G8 against Aβ (epitope: amino acids 17-24) predominantly in CA1 pyramidal neurons and in Purkinje cells (FIGS. 3 and 5). Neurons in other brain areas were also positive, but less abundant. Extracellular Aβ deposition was not the most prominent staining pattern, but occurred also as diffuse plaques in cortex, hippocampus, cerebellum, thalamus and other subcortical areas. No plaques were detected in the cerebellar molecular, piriform and granular layers, instead Aβ immunoreactivity was exclusively found within Purkinje cells (FIG. 3 e, f). Most, if not all Purkinje cells were also positive for Aβ(N3pGlu) (FIG. 3 f, g). Neuropathological analysis of tgN3Q-42 mice verified neurodegeneration of Purkinje cells, which were positive for ubiquitin, a marker for protein degradation (FIG. 3l), and accompanied abundant micro- and astrogliosis in the cerebellar molecular layer and white matter tracts (FIG. 3 h-k). This correlates well with the age-dependent motor impairment and cerebellar atrophy (FIG. 2 c).

Figure 3B:
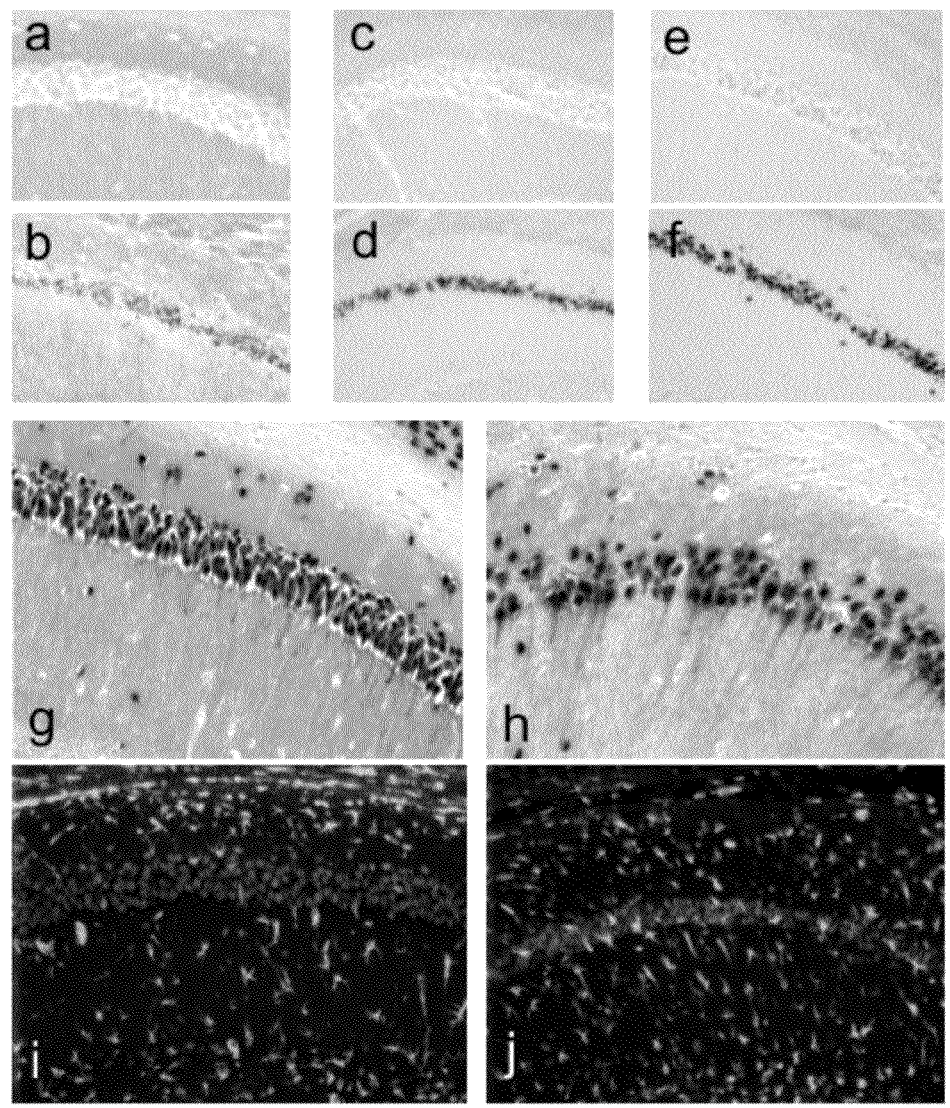
FIG. 3B Immunohistochemical and immunofluorescent staining of homozygous tgN3E-42 expressing mice. (a)-(d): 4G8 staining of the hippocampal CA1 region shows Aβ accumulation in the CA1 layer of transgenic mice only (a) and (c), wild-type mice, (b), (d) tgN3E-42 homozygous mice). (e), (f): An antibody against Aβ(N3pGlu) revealed strong Aβ accumulation in the CA1 pyramidal layer of the hippocampus in transgenic mice only (e), tgN3E-42 homozygous mice; (f), wild-type mice). A comparison of CA1 morphology in tgN3E-42 hom and wt mice indicates profound neuronal loss in this region (g), (h) in transgenic mice (g), wild-type mice; (h), tgN3E-42 homozygous transgenic mice). Double immunofluorescent staining show massively increased glia numbers in CA1 of tgN3E-42 hom vs wt (i), (j).
Figure 11:
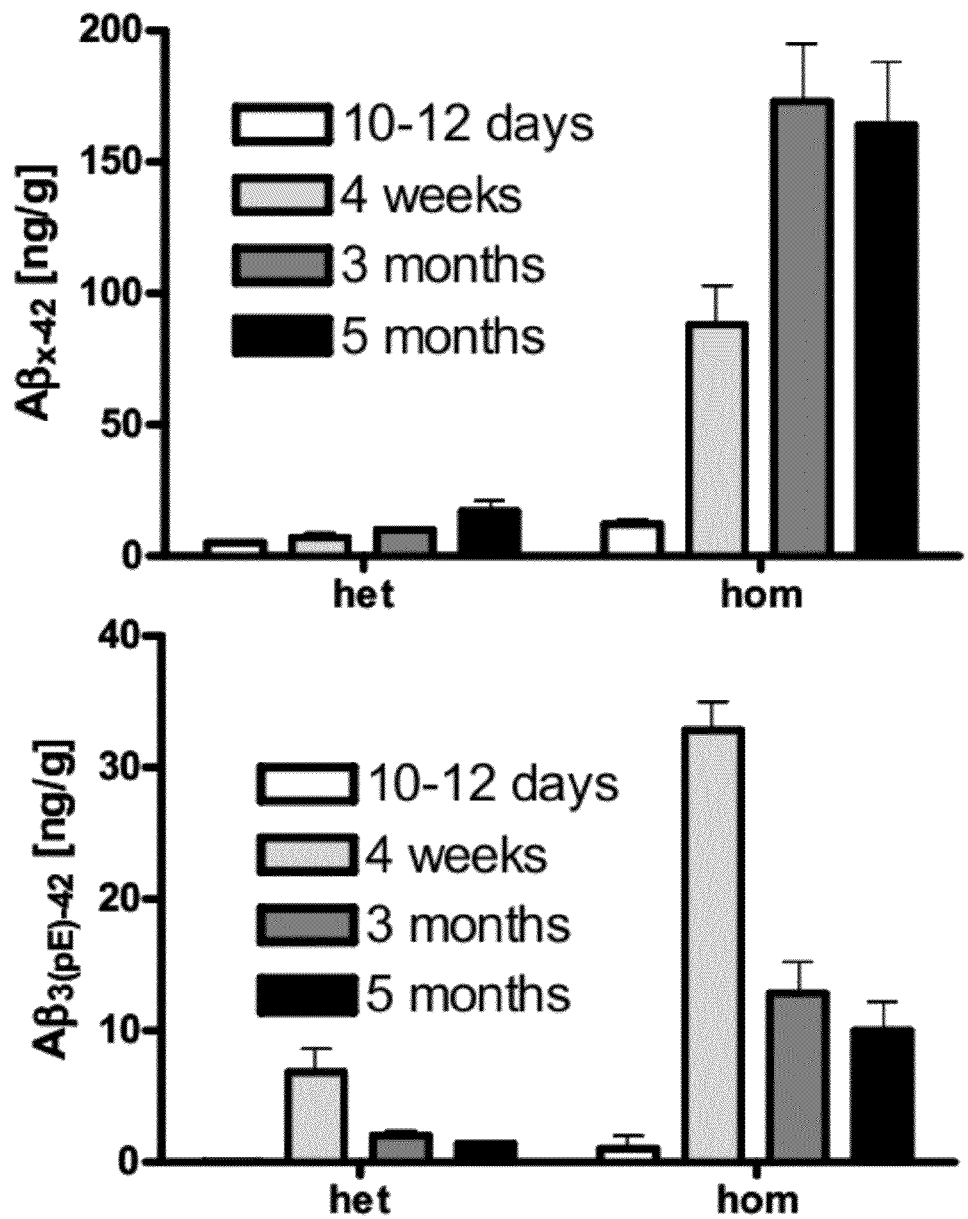
FIG. 11 shows the Aβ(x-42) (upper diagram) and the pGlu-Aβ(3-42) (lower diagram) load in brains of heterozygous and homozygous tgN3E-42 mice. After extraction from the brain, the Aβ concentrations were determined in SDS— and formic acid fractions by ELISA. The total amount of Aβ was calculated and normalized to the brain wet weight. Only male animals were analyzed (N=2-6). The homozygous animals accumulate significantly higher concentrations of pGlu-Aβ, which is accompanied by neuronal loss, memory and behavioral impairments.

Homozygous tgN3E-42 animals (tgN3E-42 hom) were generated from heterozygous tgN3E-42 (tgN3E-42 het) in order to increase the expression of the transgene. In fact, tgN3E-42 hom mice accumulate significantly higher amounts of pGlu-Aβ(3-42) compared to tgN3E-42 het. The accumulation and deposition of Aβ is most prominent in the hippocampal CA1 layer (FIG. 3B). At an age of 4 weeks, the pGlu-Aβ formation reaches a maximum according to quantification by ELISA, afterwards decreasing to lower concentrations (FIG. 11). The total Aβ concentration increases, in contrast, up to an age of 3 months. The formation of Aβ(N3pGlu) thus accelerates the deposition of other Aβ species. Accordingly, a staining of the CA1 layer was observed applying an antibody for rodent A. The increased generation of pGlu-Aβ results in cognitive decline as observed in the behavioral assays described in example 2 and illustrated in FIGS. 8, 9A, FIG. 9B and FIG. 9C. Thus, the tgN3E-42 hom represent a mouse model which is superior to investigate the role of pGlu-modified amyloid peptides formed by QC and for evaluation of treatment strategies aiming at reducing Aβ(N3pGlu), e.g. by QC inhibition.

Figure 12:
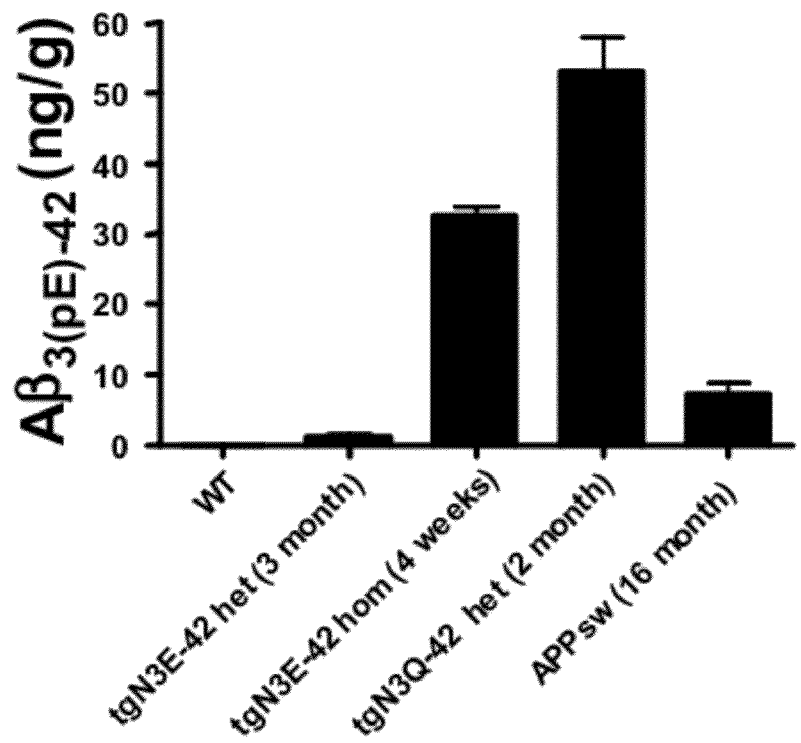
FIG. 12 shows the pGlu-Aβ(3-42) (upper diagram) and Aβx-42 (lower diagram) load in brains of heterozygous and homozygous tgN3E-42 mice, tgN3Q-42 and APPsw mice. After extraction from the brain, the Aβ concentrations were determined in SDS- and formic acid fractions by ELISA. The total amount of Aβ was calculated and normalized to the brain wet weight. The homozygous tgN3E-42 and the heterozygous tgN3Q-42 animals accumulate significantly higher concentrations of pGlu-Aβ, which is accompanied by neuronal loss, memory and behavioral impairments.
Figure 12:
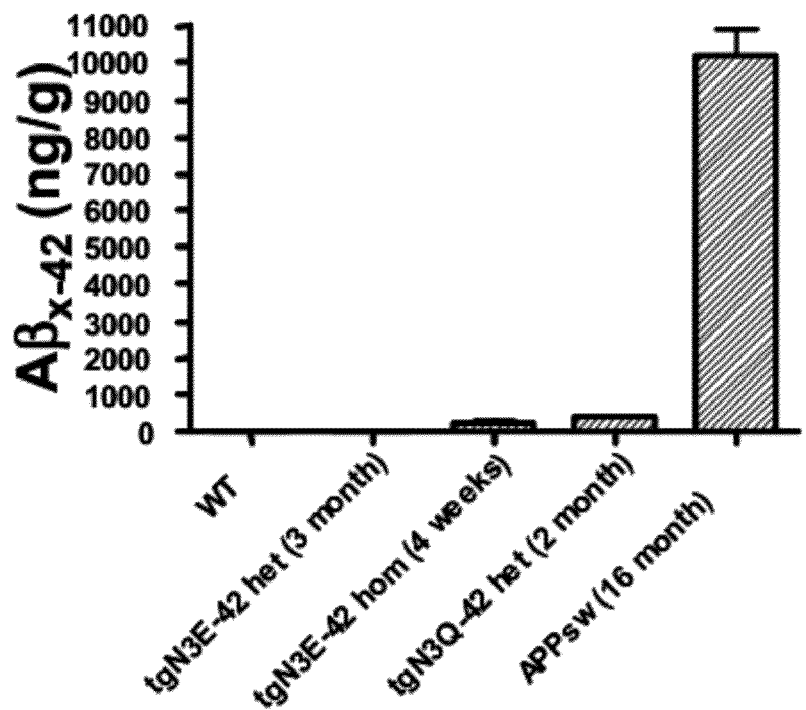

A comparison of the pGlu-Aβ content in brains of tgN3E-42 het, tgN3E-42 hom and tgN3Q-42 het mice reveals a significant difference. In homozygous tgN3E-42 and heterozygous tgN3Q-42 mice, a rapid formation of $A\beta_{3(pE)-42}$ was observed in the first weeks of their life, in contrast to tgN3E-42 het and transgenic mice which overexpress the Amyloid Precursor Protein carrying the Swedish Mutation (APPsw mice) (FIG. 12). The comparison shows another important and unique feature of the tgN3E-42 and tgN3Q-42 lines: The pGlu-Aβ content in brain reaches in several weeks an amount, which is never achieved in other mouse models, which are state of the art, e.g. APPsw mice. For instance, in 16 months old APPsw mice, the Aβ(N3pGlu) in the brain is approximately 4-5 times lower than in 1-2 month old tgN3Q-42 or tgN3E-42 hom mice. The total Aβ load in these APPsw mice, however, exceeds that of tgN3E-42 hom and tgN3Q-42 by a factor of more than 100 (FIG. 12).

This example proves, that the transgenic strategy offers a superior chance to investigate the role of distinct Aβ peptides, e.g. Aβ(N3pGlu), in AD pathology. Therefore, by adaptation of the transgenes, it is possible to express also other N- and C-terminal Aβ species neuron-specifically and to investigate their neurotoxic potential.

The tgN3E-42 and tgN3Q-42 mice prove finally the neurotoxicity of pGlu-modified Aβ peptides, because the accumulation of pGlu-Aβ(3-42) is accompanied by neuronal loss, impairments in long-term potentiation and cognition. These combined features are unique to these animal models, thus representing a major advance in rodent models with Alzheimer's-like pathology.

Figure 13:
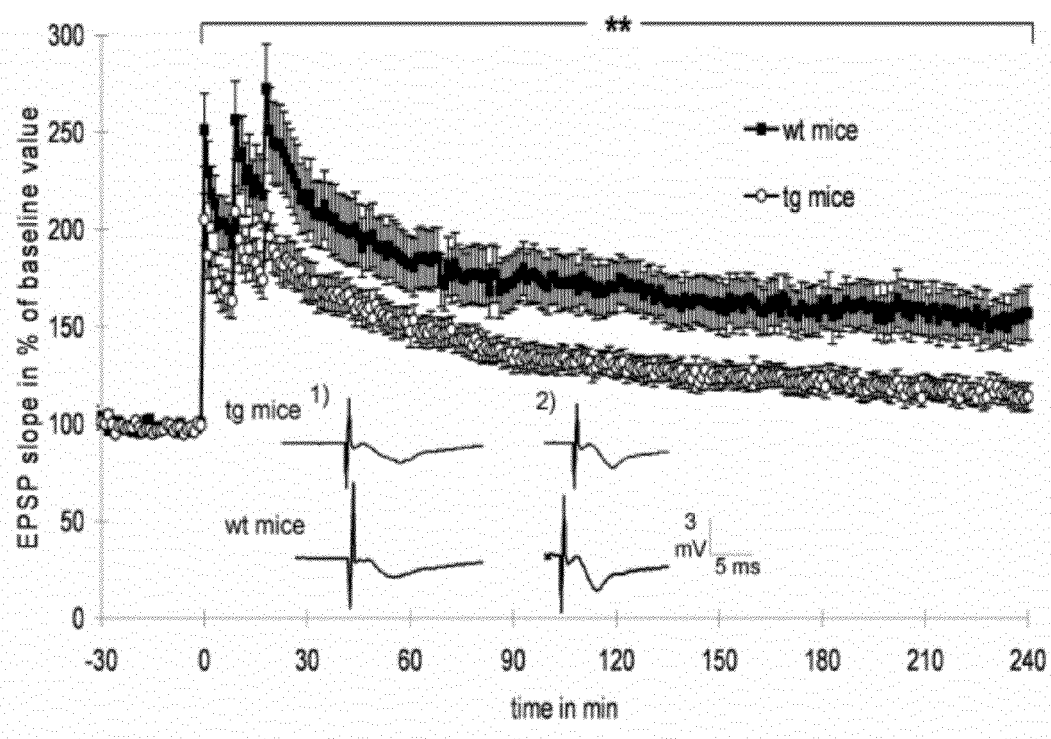
FIG. 13 shows the long-term potentiation of EPSP after application of strong tetanus (time point 0). The LTP of tgN3E-42 homozygous mice was significantly diminished compared to WT mice (WT mice vs. tg mice: $p=0.007$; tg mice: n=18; WT: n=12; ANOVA with repeated measures). Analog traces represent typical recordings of single experiments taken 10 minutes before tetanisation (1) and 240 minutes after tetanisation (2).

Hippocampal long-term potentiation (LTP) was assessed in homozygous tgN3E-42 mice and wild-type littermates, in order to investigate the physiological basis of the behavioral impairments. At an age of 5 months, tgN3E-42 homozygous and wild-type littermates were sacrificed and hippocampal slices prepared for the measurements of LTP ex vivo. The LTP was significantly reduced in slices from tgN3E-42 homozygous mice (FIG. 13). Shortly after application of the first tetanus train, the fEPSP-slope was significantly diminished (205.3±13.2% at time point 1) compared to fEPSP-slope of wt mice (251.4±18.8% at time point 1). The impaired potentiation of fEPSPs from tg mice persisted over the time and remained significantly reduced after 4 h of LTP measurement (tgN3E-42 mice: 114.0±6.8%; WT mice: 157.1±14.0% at time point 240). Analyzing the relation between the stimulation intensity and the resulting signal size (fEPSP-slope) revealed a significant decreased EPSP slope in tgN3E-42 mice, compared to wt mice (max. EPSP slope of tgN3E-42 hom mice: 3.7±0.4 mV/ms; max. EPSP slope of WT mice: 5.6±0.5 mV/ms, both at 3 mV stimulation strength). Values of Input-output-curve are given as mean±S.E.M.

The data indicate that the genetic modification of the tgN3E-42 mice impaired both baseline synaptic transmission and thus normal neuronal function and also synaptic plasticity (LTP). The LTP disruption contributes to an impaired hippocampus-dependent memory function, as the cellular correlative of learning and memory is disturbed in that area of the mouse brain. The reduced EPSP amplitude reflects a loss of synapses, which clearly coincides with the neuronal degeneration observed in tgN3E-42 homozygous mice.

Long-standing evidence shows that progressive cerebral deposition of Aβ plays a seminal role in the pathogenesis of AD. There is great interest, therefore, in understanding the proteolytic processing of APP and its proteases responsible for cleaving at the N- and C-termini of the Aβ region. Ragged peptides with a major species beginning with phenylalanine at position 4 of Aβ have been reported already in 1985 by Masters et al. (Masters, C. L., et al. Amyloid plaque core protein in Alzheimer disease and Down syndrome, Proc Natl Acad Sci USA 82, 4245-4249 (1985)). This finding has been disputed, because no N-terminal sequence could be obtained from cores purified in a sodium dodecyl sulfate-containing buffer, which mounted in the suggestion that the N-terminus is blocked (Selkoe, D. J., Abraham, C. R., Podlisny, M. B. & Duffy, L. K. Isolation of Low-Molecular-Weight Proteins from Amyloid Plaque Fibers in Alzheimer's Disease, Journal of Neurochemistry 46, 1820-1834 (1986); Gorevic, P. D., et al. Isolation and partial characterization of neurofibrillary tangles and amyloid plaque core in Alzheimer's disease: immunohistological studies, J Neuropathol Exp Neurol 45, 647-664 (1986)). In 1992, Mori et al. first described the presence of Aβ (N3pGlu) using mass spectrometry of purified Aβ protein from AD brains, which explains the difficulties in sequencing the amino-terminus (Mori, H., Takio, K., Ogawara, M. & Selkoe, D. J. Mass spectrometry of purified amyloid beta protein in Alzheimer's disease. J Biol. Chem. 267, 17082-17086 (1992)). They reported that only 10-15% of the total Aβ isolated by this method begins at position 3 with Aβ(N3pGlu). Later it became clear that Aβ (N3pGlu) represents a dominant fraction of Aβ peptides in Aβ and Down's syndrome brain (Kuo, Y. M., Emmerling, M. R., Woods, A. S., Cotter, R. J. & Roher, A. E. Isolation, chemical characterization, and quantitation of Abeta 3-pyroglutamyl peptide from neuritic plaques and vascular amyloid deposits, Biochem Biophys Res Commun 237, 188-191. (1997); Saido, T. C., et al. Dominant and differential deposition of distinct beta-amyloid peptide species, Abeta N3(pE), in senile plaques, Neuron 14, 457-466 (1995); Piccini, A., et al. {beta}-Amyloid Is Different in Normal Aging and in Alzheimer Disease, J. Biol. Chem. 280, 34186-34192 (2005); Saido, T. C., Yamao-Harigaya, W., Iwatsubo, T. & Kawashima, S. Amino- and carboxyl-terminal heterogeneity of beta-amyloid peptides deposited in human brain, Neurosci Lett 215, 173-176 (1996); Kuo, Y. M., et al. Comparative analysis of amyloid-beta chemical structure and amyloid plaque morphology of transgenic mouse and Alzheimer's disease brains, J Biol Chem 276, 12991-12998 (2001); Hosoda, R., et al. Quantification of modified amyloid beta peptides in Alzheimer disease and Down syndrome brains, J Neuropathol Exp Neurol 57, 1089-1095 (1998); Harigaya, Y., et al. Amyloid beta protein starting pyroglutamate at position 3 is a major component of the amyloid deposits in the Alzheimer's disease brain, Biochem Biophys Res Commun 276, 422-427 (2000); Iwatsubo, T., Saido, T. C., Mann, D. M., Lee, V. M. & Trojanowski, J. Q., Full-length amyloid-beta (1-42 (43)) and amino-terminally modified and truncated amyloid-beta 42(43) deposit in diffuse plaques, Am J Pathol 149, 1823-1830 (1996); Miravalle, L., et al. Amino-Terminally Truncated Abeta Peptide Species Are the Main Component of Cotton Wool Plaques, Biochemistry 44, 10810-10821 (2005); Piccini, A., et al. Association of a Presenilin 1 S170F Mutation With a Novel Alzheimer Disease Molecular Phenotype, Arch Neurol. 64, 738-745. (2007); Russo, C., et al. Heterogeneity of water-soluble amyloid beta-peptide in Alzheimer's disease and Down's syndrome brains, FEBS Lett 409, 411-416. (1997); Guntert, A., Dobeli, H. & Bohrmann, B. High sensitivity analysis of amyloid-beta peptide composition in amyloid deposits from human and PS2APP mouse brain, Neuroscience, 143, 461-475 (2006); Tekirian, T. L., et al. N-terminal heterogeneity of parenchymal and cerebrovascular Abeta deposits, J Neuropathol Exp Neurol 57, 76-94 (1998)). N-terminal deletions in general enhance aggregation of β-amyloid peptides in vitro (Pike, C. J., Overman, M. J. & Cotman, C. W. Amino-terminal Deletions Enhance Aggregation of beta-Amyloid Peptides in Vitro, J. Biol. Chem. 270, 23895-23898 (1995)).

Therefore, the inventors generated Aβ3-42 transgenic mice that express Aβ(N3E-42) of SEQ ID No: 1 with the natural glutamate at the N-terminus (tgN3E-42) and mice that express Aβ(N3Q-42) of SEQ ID No: 2 starting with a glutamine (tgN3Q-42). Due to the replacement of N-terminal glutamate by glutamine the Aβ peptides are at least five orders of magnitude faster converted into pyroglutamate by QC activity (Schilling, S., Hoffmann, T., Manhart, S., Hoffmann, M. & Demuth, H. U. Glutaminyl cyclases unfold glutamyl cyclase activity under mild acid conditions. FEBS Lett 563, 191-196 (2004); Cynis, H., et al. Inhibition of glutaminyl cyclase alters pyroglutamate formation in mammalian cells, Biochim Biophys Acta 1764, 1618-1625 (2006)). Furthermore, cyclization of glutamate to pyroglutamate is a pH dependent process. The enzymatic glutamine conversion is favored at pH 7.5, while glutamate conversion occurs at an optimum at pH 6.5. This finding might be of importance for deciphering the events leading to deposition of highly toxic pyroglutamate peptides in AD. Clearly, along the axonal transport of Aβ peptides, QC and its substrate are co-localized within an acidic compartment favoring the cyclization of N-glutamate substrates. Furthermore, axonal transport has been shown to be impaired in AD brain, assisting the generation of neurotoxic Aβ(N3pGlu) species. In addition, pharmacological inhibition of QC activity by a QC-specific inhibitor significantly reduced the level of Aβ(N3pGlu) in vitro (Cynis, H., et al. Inhibition of glutaminyl cyclase alters pyroglutamate formation in mammalian cells, Biochim Biophys Acta 1764, 1618-1625 (2006)). In conclusion, the inventors have shown firstly that Aβ(N3pGlu) is a dominant peptide in the neurotoxic amyloid cascade inducing severe neurodegeneration, secondly that this toxicity is most likely caused by intraneuronal Aβ(N3pGlu) aggregation, and lastly that QC activity modulates Aβ(N3pGlu) formation in brain, which makes QC an ideal therapeutic target to prevent formation of harmful Aβ(N3pGlu) peptides in AD.

Figure 6:
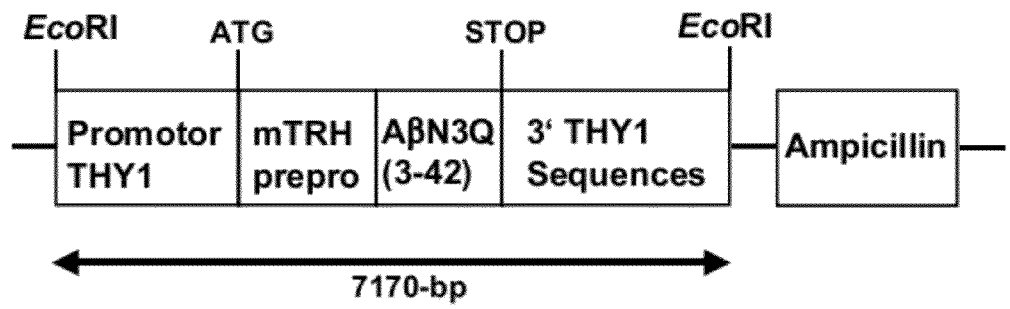
FIG. 6 shows the restriction strategy used to prepare the fragment for pronucleus injection. Schematic representation of tgN3Q-42 plasmid with location of EcoRI restriction sites used to generate the 7170-bp fragment containing the transgene (TRH-AβN3Q(3-42) or TRH-AβN3E(3-42) transgene+ Thy1 promoter). The figure is not depicted to scale.
Figure 6:
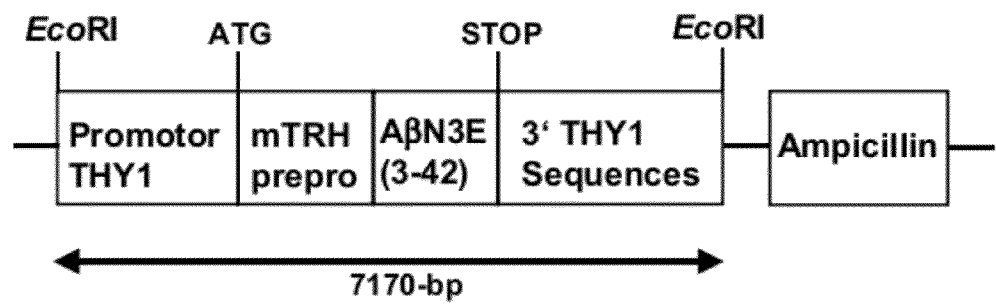
Figure 7:
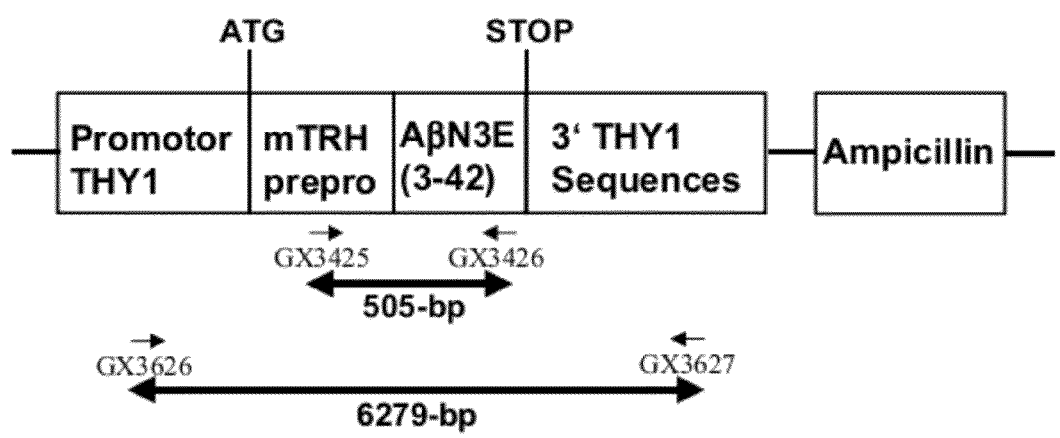
FIG. 7 shows the PCR genotyping methodology: Localisation of primers used for the detection of random integration and transgene integrity. The corresponding amplification product sizes are indicated. Bold line represents plasmid backbone sequences. Half arrows illustrate the primers' localisation. Figures are not depicted to scale. The TRH-AβN3E(3-42) transgene construct has the same structure.
Figure 8:
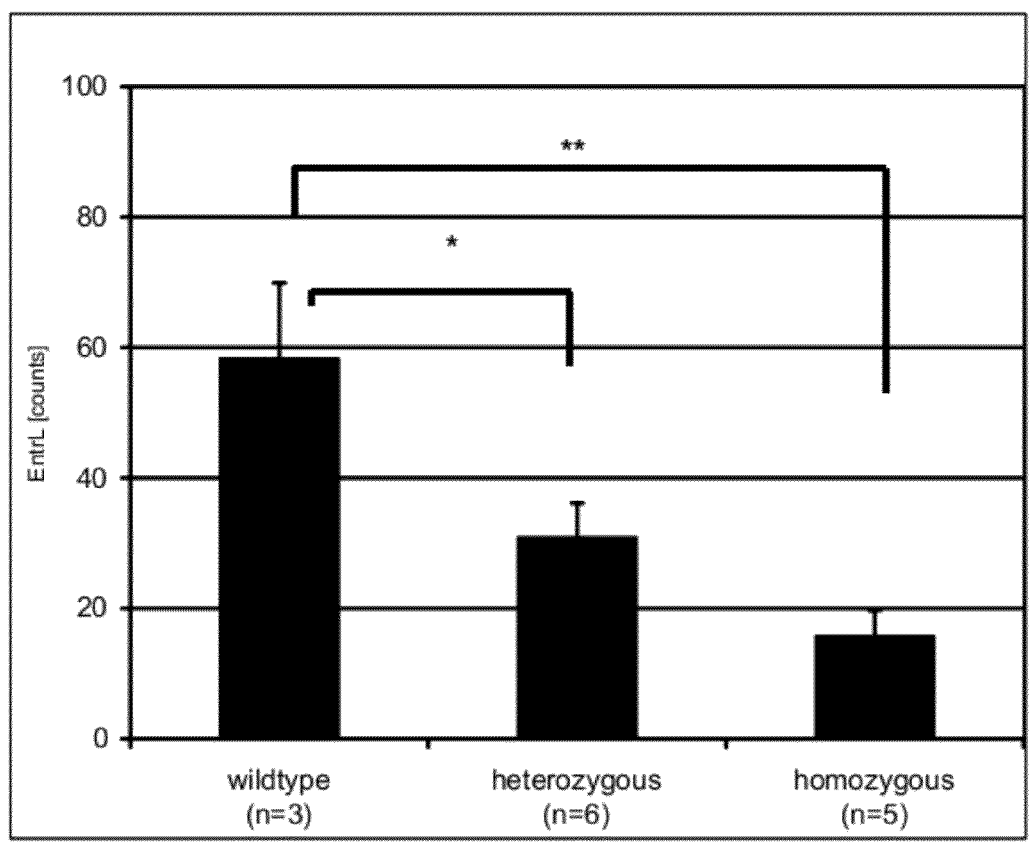
FIG. 8 illustrates the behavior of 7 weeks old tgN3E-42 mice in the dark light box device: tgN3E-42 mice show a significantly decreased number of entries into the light arena ($p<0.01$ heterozygous and $p<0.05$ homozygous mice) compared to wildtype littermates, indicating emotional changes in tgN3E-42.
Figure 9A:
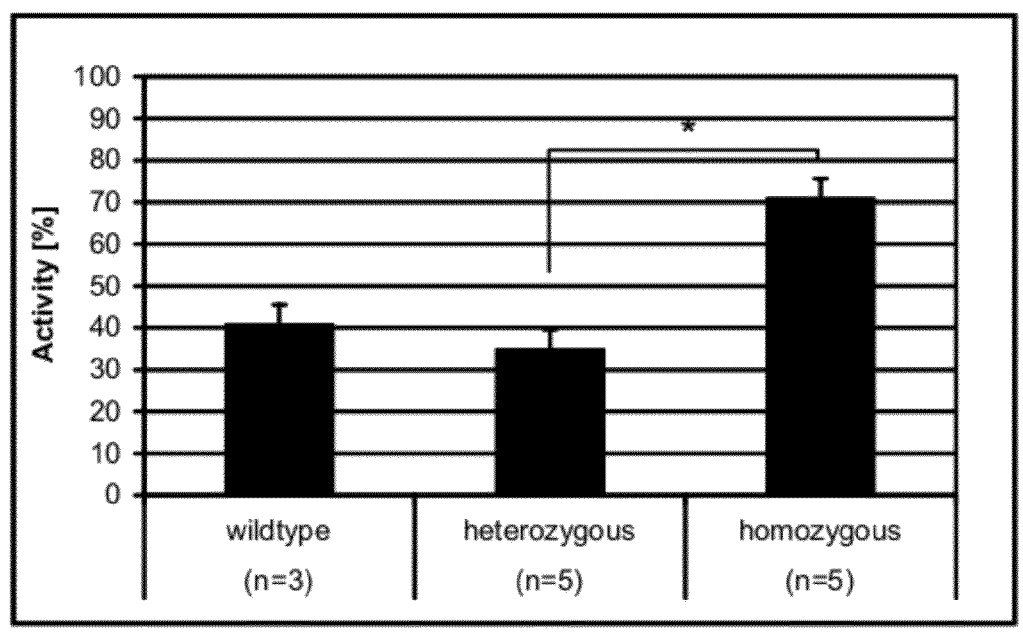
FIG. 9A shows the behavior of 3 months old tgN3E-42 mice in the fear conditioning device: homozygous mice react in the contextual fear with increased activity and reduced freezing behavior compared to heterozygous mice and wildtype littermates.
Figure 9B:
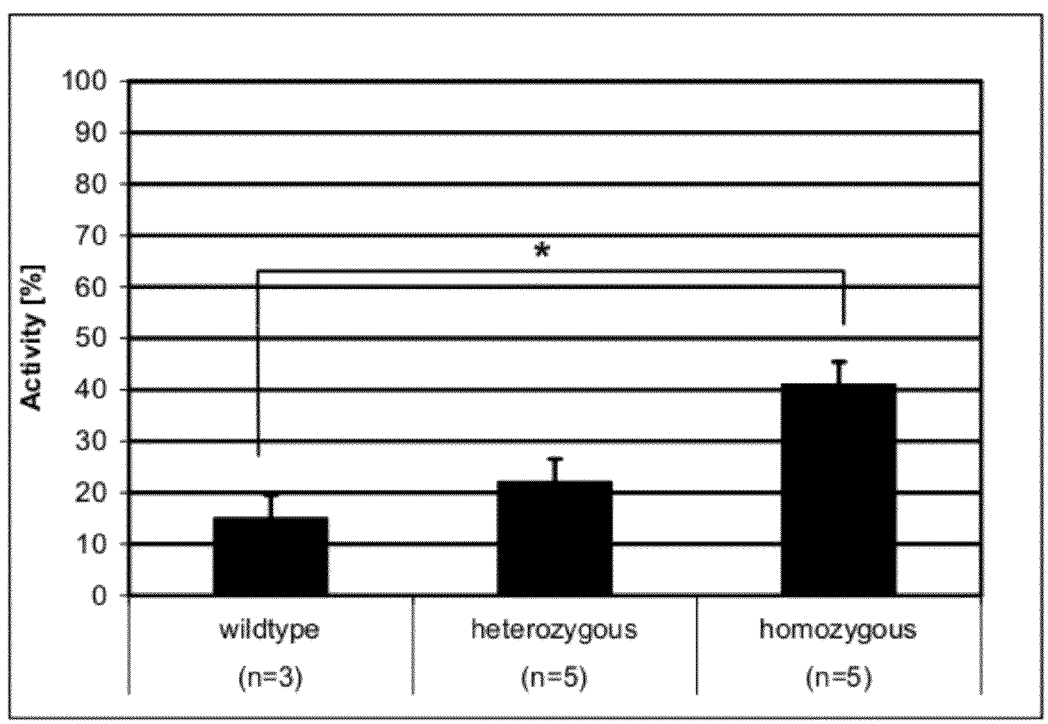
FIG. 9B shows the behavior of 3 months old tgN3E-42 mice in the fear conditioning device: Homozygous tgN3E-42 mice react in the cued fear conditioning with increased activity compared to littermates.
Figure 9C:
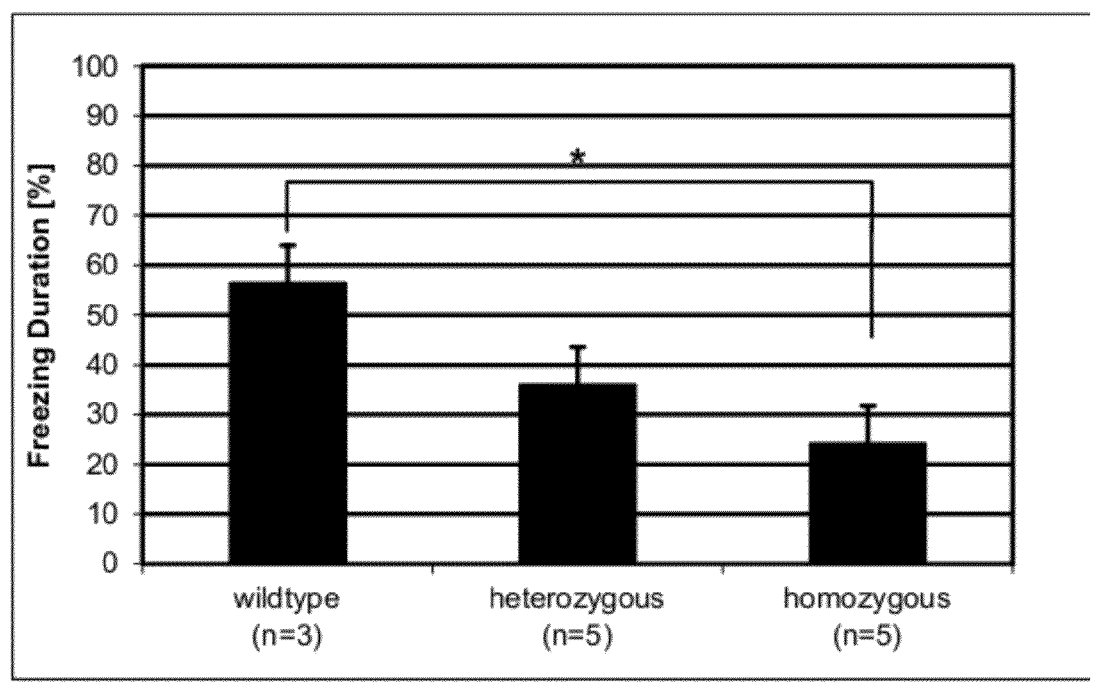
FIG. 9C shows the behavior of 3 months old tgN3E-42 mice in the fear conditioning device: Homozygous tgN3E-42 mice show in the context a significantly shortened freezing duration. The results of FIG. 9A, FIG. 9B and FIG. 9C prove a cognitive decline of transgenic tgN3E-42 mice.
Figure 10:
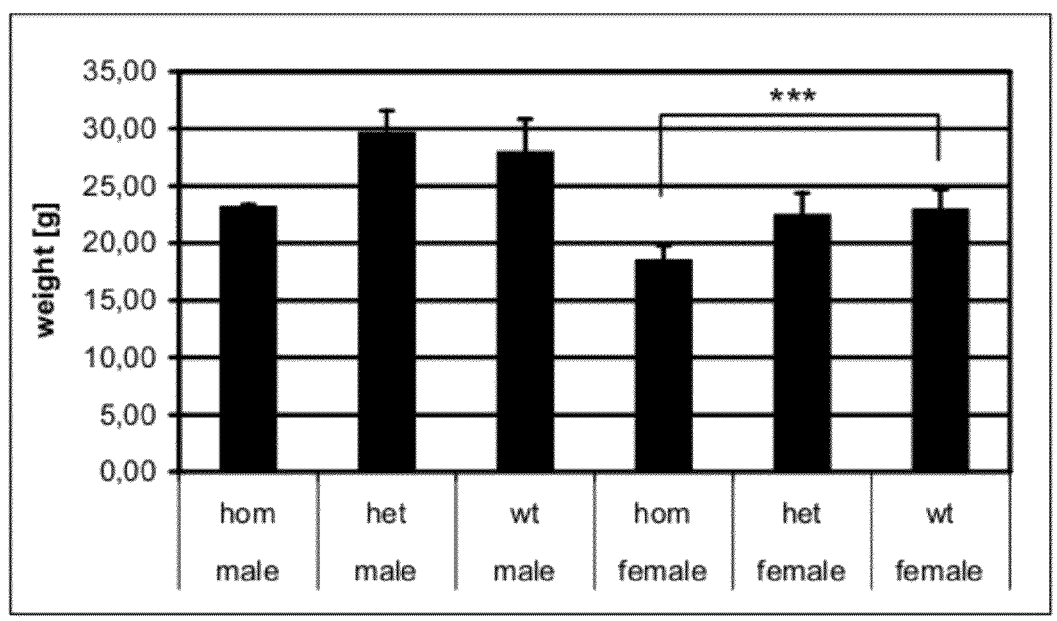
FIG. 10 shows the weight of tgN3E-42 mice at an age of 3 months. There was a reduced weight observed in heterozygous and homozygous mice, which reached statistical significance for the homozygous mice. The reduction in weight is caused by the motoric deficits of the homogeneous tgN3E-42 mice, which develops at young age due to accumulation of pGlu-Aβ3-42 and neuronal loss.

In this regard, the use of a prepropeptide expression strategy as depicted in FIG. 1 and FIG. 6 is completely novel in this field. Using the murine Thyrotropin releasing hormone preprosequence, it is possible to generate distinct Aβ species in a transgenic animal, as shown for Aβ3E-42 and Aβ3Q-42 and resulting pGlu-formation in the examples and figures of the present invention. The Aβ sequences might be exchanged by other sequences of amyloid peptides in order to characterize the pathophysiologic function of these peptides. During normal APP metabolism, a variety of Aβ peptides is formed caused by alternative β- and γ-secretase cleavages. According to the presented strategy, it is possible to develop further transgenic animals on basis of the preprotein processing strategy described here, which are models for Alzheimers disease, Familial British Dementia and Familial Danish Dementia by exchanging the TRH by the respective amyloid peptide sequences as depicted in FIGS. 1, 6 and 7.

In a further embodiment, the present invention comprises transgenic mouse lines expressing either Aβ3E-40 of SEQ ID No: 3 (tgN3E-40) or AβN3Q-40 of SEQ ID No: 4 (tg-N3Q-40), resulting in the formation of Aβ(N3pGlu-40).

Preferred according to the present invention are animal models, which comprise at least one nucleotide sequence selected from Aβ3E-42 (SEQ ID No: 9), Aβ3Q-42 (SEQ ID No: 10), Aβ3E-40 (SEQ ID No: 11) and Aβ3Q-40 (SEQ ID No: 12) in the expression constructs, more preferably at least one nucleotide sequence selected from Aβ3E-42 (SEQ ID No: 9) and Aβ3Q-42 (SEQ ID No: 10).

In a further preferred embodiment, the animal models according to the present invention comprise at least one nucleotide sequence selected from mTRH-Aβ3E-42 (SEQ ID No: 6) and mTRH-Aβ3Q-42 (SEQ ID No: 8).

In a further preferred embodiment, the animal models according to the present invention comprise at least one nucleotide sequence selected from Thy-1-mTRH-Aβ3E-42 (SEQ ID No: 5) and Thy-1-mTRH-Aβ3Q-42 (SEQ ID No: 7).

Preferred animal models are heterozygous for at least one nucleotide sequence selected from Thy-1-mTRH-Aβ3E-42 (SEQ ID No: 5), Thy-1-mTRH-Aβ3Q-42 (SEQ ID No: 7), mTRH-Aβ3E-42 (SEQ ID No: 6), mTRH-Aβ3Q-42 (SEQ ID No: 8), Aβ3E-42 (SEQ ID No: 9), Aβ3Q-42 (SEQ ID No: 10), Aβ3E-40 (SEQ ID No: 11) and Aβ3Q-40 (SEQ ID No: 12).

Especially preferred are animal models that are homozygous for at least one nucleotide sequence selected from Thy-1-mTRH-Aβ3E-42 (SEQ ID No: 5), Thy-1-mTRH-Aβ3Q-42 (SEQ ID No: 7), mTRH-Aβ3E-42 (SEQ ID No: 6), mTRH-Aβ3Q-42 (SEQ ID No: 8), Aβ3E-42 (SEQ ID No: 9), Aβ3Q-42 (SEQ ID No: 10), Aβ3E-40 (SEQ ID No: 11) and Aβ3Q-40 (SEQ ID No: 12).

Furthermore, the present invention comprises transgenic mouse lines expressing recombinant glutaminyl cyclase and at least one Aβ peptide selected from Aβ3E-42 of SEQ ID No: 1, AβN3Q-42 of SEQ ID No: 2, Aβ3E-40 of SEQ ID No: 4 or AβN3Q-40 of SEQ ID No: 4. Such animals can be obtained by crossbreeding of transgenic mouse lines, which express recombinant glutaminyl cyclase, with mouse lines, which express at least one Aβ peptide selected from Aβ3E-42 of SEQ ID No: 1, AβN3Q-42 of SEQ ID No: 2, Aβ3E-40 of SEQ ID No: 3 or AβN3Q-40 of SEQ ID No: 4.

Preferred cross-bred mouse lines express mammalian QC, in particular human or murine QC, or Papaya QC. Especially preferred is mammalian QC, since the effectors identified by these screening methods shall be used for the treatment of diseases in mammals, especially in humans.

Further preferred cross-bred mouse lines express an isoenzyme of QC.

These isoenzymes, displaying significant sequence homology to glutaminyl cyclase, are glutaminyl-peptide cyclotransferase-like proteins (QPCTLs) from human (further named as human isoQC) (GenBank accession no. NM_017659), mouse (GenBank accession no. NM_027455), *Macaca fascicularis* (GenBank accession no. AB168255), *Macaca mulatta* (GenBank accession no. XM_001110995), cat (GenBank accession no. XM_541552), rat (GenBank accession no. XM_001066591), cow (GenBank accession no. BT026254) or an analogue thereof having at least 50%/75% sequence identity/similarity, preferably 70%/85% sequence identity/similarity, most preferably 90%/95% sequence identity/similarity.

The sequences are given in SEQ. ID Nos: 13 to 23. Further disclosed are nucleic acid sequences coding for these QPCTLs (SEQ. ID Nos: 24 to 34).

Preferred according to the present invention are cross-bred mouse lines expressing QPCTLs selected from the group consisting of human QPCTLs including isoforms and spliceforms thereof, given in SEQ. ID Nos: 13 to 15, 22 and 23; rat (SEQ. ID No: 19) and mouse (SEQ. ID No: 20).

More preferred according to the present invention are cross-bred mouse lines expressing QPCTLs selected from the group consisting of human QPCTL including isoforms, given in SEQ. ID Nos: 13 to 15; and mouse (SEQ. ID No: 20).

Most preferred according to the present invention are cross-bred mouse lines expressing QPCTLs selected from the group consisting of human (SEQ. ID No: 13), and mouse (SEQ. ID No: 20).

In this regard, specific reference is made to U.S. 60/846,244 for specific further disclosure of the QPCTL-isoenzymes. This application is incorporated herein by reference.

Transgenic mouse lines, which express recombinant glutaminyl cyclase can be produced according to the procedures described in U.S. 60/885,649. This application is incorporated herein by reference in its entirety regarding the production and testing of transgenic mouse lines, which express recombinant glutaminyl cyclase.

In a preferred embodiment, the present invention provides the use of inhibitors of the effects of Aβ-peptide, as selected with use of the present inventive animal model, in Mild Cognitive Impairment, Alzheimer's disease, Down Syndrome, Familial Danish Dementia and Familial British Dementia.

In a further embodiment, the present invention provides the use of promoters of the effects of Aβ-peptide, as selected with use of the present inventive animal model, for the stimulation of gastrointestinal tract cell proliferation, especially gastric mucosal cell proliferation, epithelial cell proliferation, the differentiation of acid-producing parietal cells and histamine-secreting enterochromaffin-like (ECL) cells, and the expression of genes associated with histamine synthesis and storage in ECL cells, as well as for the stimulation of acute acid secretion in mammals by maintaining or increasing the concentration of active[pGlu$^1$]-gastrin.

In a further embodiment, the present invention provides the use of inhibitors of Aβ-peptide effects, as selected with use of the present inventive animal model, for the treatment of duodenal ulcer disease and gastric cancer with or without *Helicobacter pylori* in mammals by decreasing the conversion rate of inactive [Gln$^1$]Gastrin to active [pGlu$^1$]Gastrin.

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioural and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

In another embodiment, the present invention provides the use of promoters of Aβ-peptide effectors, as selected with use of the present inventive animal model, for the preparation of antipsychotic drugs and/or for the treatment of schizophrenia in mammals. The effectors of Aβ-peptide effects either maintain or increase the concentration of active [pGlu$^1$]neurotensin.

Fertilization promoting peptide (FPP), a tripeptide related to thyrotropin releasing hormone (TRH), is found in seminal plasma. Recent evidence obtained in vitro and in vivo showed that FPP plays an important role in regulating sperm fertility. Specifically, FPP initially stimulates nonfertilizing (incapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in incapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on", and others possibly being involved in the acrosome reaction itself. Calcitonin and angiotensin II, also found in seminal plasma, have similar effects in vitro on incapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

In a further embodiment, the present invention provides the use of inhibitors of Aβ peptide effects, as selected with the present inventive animal model, for the preparation of fertilization prohibitive drugs and/or to reduce the fertility in mammals. The inhibitors of Aβ peptide effects decrease the concentration of active [pGlu$^1$]FPP, leading to a prevention of sperm capacitation and deactivation of sperm cells. In contrast it could be shown that promotors of Aβ peptide effects are able to stimulate fertility in males and to treat infertility.

In another embodiment, the present invention provides the use of inhibitors/promoters of Aβ peptide effects, as selected with use of the present inventive animal model, for the preparation of a medicament for the treatment of pathophysiological conditions, such as suppression of proliferation of myeloid progenitor cells, neoplasia, inflammatory host responses, cancer, malign metastasis, melanoma, psoriasis, rheumatoid arthritis, atherosclerosis, restenosis, lung fibrosis, liver fibrosis, renal fibrosis, graft rejection, acquired immune deficiency syndrom, impaired humoral and cell-mediated immunity responses, leukocyte adhesion and migration processes at the endothelium.

In a further embodiment, the present invention provides the use of inhibitors/promoters of Aβ peptide effects, as selected with use of the present inventive animal model, for the preparation of a medicament for the treatment of impaired food intake and sleep-wakefulness, impaired homeostatic regulation of energy metabolism, impaired autonomic function, impaired hormonal balance and impaired regulation of body fluids.

Polyglutamine expansions in several proteins lead to neurodegenerative disorders, such as Chorea Huntington, Parkinson disease and Kennedy's disease. The mechanism therefore remains largely unknown. The biochemical properties of polyglutamine repeats suggest one possible explanation: endolytic cleavage at a glutaminyl-glutaminyl bond followed by pyroglutamate formation may contribute to the pathogenesis through augmenting the catabolic stability, hydrophobicity, amyloidogenicity, and neurotoxicity of the polyglutaminyl proteins (Saido, T. C.; Med Hypotheses (2000) March; 54(3):427-9).

In a further embodiment, the present invention therefore provides the use of inhibitors/promoters of Aβ peptide effectors, as selected with the present inventive animal model, for the preparation of a medicament for the treatment of Parkinson disease and Huntington's disease.

ADan and ABri are, like AβN3pE(3-42) pGlu-amyloidogenic peptides, which are deposited in brains of patients suffering from Familial Danish Dementia (FDD) or Familial British Dementia (FBD). These dementia are inherited disorders, which are based on a mutation in a stop codon in the Bri protein which is encoded on chromosome 13 (Vidal, R., Frangione, B., Rostagno, A., Mead, S., Revesz, T., Plant, G. & Ghiso, J. (1999) Nature 399, 776-781. Ghiso, J., Revesz, T., Holton, J., Rostagno, A., Lashley, T., Houlden, H., Gibb, G., Anderton, B., Bek, T., Bojsen-Moller, M. et al. (2001) Amyloid. 8, 277-284.) The pathological hallmarks of the diseases are very similar to Alzheimers Disease, including cerebral amyloid angiopathy and neuroinflammation (Rostagno, A., Revesz, T., Lashley, T., Tomidokoro, Y., Magnotti, L., Braendgaard, H., Plant, G., Bojsen-Moller, M., Holton, J., Frangione, B. et al. (2002) J Biol Chem 277, 49782-49790.). Importantly, the deposited amyloid peptides are N-terminally pGlu-modified and the plaques in FDD consist of pGlu-modified Adan and Aβ (Tomidokoro, Y., Lashley, T., Rostagno, A., Neubert, T. A., Bojsen-Moller, M., Braendgaard, H., Plant, G., Holton, J., Frangione, B., Revesz, T. et al. (2005) J. Biol. Chem. 280, 36883-36894.). The pGlu-Modification apparently speeds the aggregate formation, since soluble Adan has been described, which does not contain N-terminal pGlu (Tomidokoro, Y., Lashley, T., Rostagno, A., Neubert, T. A., Bojsen-Moller, M., Braendgaard, H., Plant, G., Holton, J., Frangione, B., Revesz, T. et al. (2005) J. Biol. Chem. 280, 36883-36894.).

In a further embodiment, the present invention provides the use of inhibitors/promoters of Aβ peptide effects, as selected with the present inventive animal model, for the preparation of a medicament for the treatment of Familial British dementia and/or Familial Danish Dementia.

Chemotactic cytokines (chemokines) are proteins that attract and activate leukocytes and are thought to play a fundamental role in inflammation. Chemokines are divided into four groups categorized by the appearance of N-terminal cysteine residues ("C"-; "CC"-; "CXC"- and "CX3C"- chemokines). "CXC"-chemokines preferentially act on neutrophils. In contrast, "CC"-chemokines attract preferentially monocytes to sites of inflammation. Monocyte infiltration is considered to be a key event in a number of disease conditions (Gerard, C. and Rollins, B. J. (2001) Nat. Immunol 2, 108-115; Bhatia, M., et al., (2005) Pancreatology. 5, 132-144; Kitamoto, S., Egashira, K., and Takeshita, A. (2003) J Pharmacol Sci. 91, 192-196). The MCP family, as one family of chemokines, consists of four members (MCP-1-4), displaying a preference for attracting monocytes but showing differences in their potential (Luini, W., et al., (1994) Cytokine 6, 28-31; Uguccioni, M., et al., (1995) Eur J Immunol 25, 64-68). In the following both cDNA as well as amino acid sequences of MCP-1-4 are indicated:

The mature forms of human and rodent MCP-1-4 are post-translationally modified by glutaminyl cyclase to possess an N-terminal pyroglutamyl (pGlu) residue. The N-terminal pGlu modification makes the proteins resistant against N-terminal degradation by aminopeptidases, which is of importance, since chemotactic potency of MCP-1-4 is mediated by its N-terminus (Van Damme, J., et al., (1999) Chem Immunol 72, 42-56).

In a further embodiment, the present invention provides the use of inhibitors/promoters of Aβ peptide effects, as selected with the present inventive animal model, for the preparation of a medicament for the treatment of diseases, which are mediated by MCP_1-4, preferably MCP-1, which diseases are for example chronic and acute inflammations, e.g. rheumatoid arthritis, atherosclerosis, restenosis or pancreatitis.

In another embodiment, the present invention provides a general way to reduce or inhibit the effects of Aβ peptide by using the test agent selected above.

Also provided are non-human transgenic animals wherein the transgene encodes at least one Aβ peptide selected from AβN3E-42 (SEQ ID No: 1), AβN3Q-42 (SEQ ID No: 2), AβN3E-40 (SEQ ID No: 3) and AβN3Q-40 (SEQ ID No: 4).

Also provided is a method for screening for a target compound that is influenced by Aβ-peptide production, wherein said method comprises the evaluation the effects of Aβ-peptide in vivo with the use of the inventive transgenic non-human animal or the inventive transgenic mouse on a possible target compound.

More preferably, said method for screening for therapeutic agents that inhibit or promote Aβ peptide effects comprises
(a) administering test agents to the transgenic mouse lines according to the present invention,
(b) evaluating the effects of the test agent on the neurological phenotype of the mouse, and
(c) selecting a test agent which inhibits or promotes Aβ peptide effects.

The invention further provides a method of the treatment or prevention of an Aβ peptide-related disease comprising
(d) administering the test agent selected in the aforementioned screening method; and
(e) monitoring the patient for a decreased clinical index for Aβ peptide-related diseases.

Preferred according to the present invention are test agents, which are identified as inhibitors of the Aβ peptide effects in the aforementioned screening and/or treatment methods.

The Aβ peptide-related disease is preferably Alzheimer's disease or neurodegeneration in Down Syndrome.

"Effects of Aβ-peptide" in the present context means all changes mediated directly or indirectly by Aβ-peptide or as a consequence of the presence of Aβ peptide. This includes in an exemplary, non-limiting fashion neuronal and neurological effect, toxicity or vaccinating effects.

The present transgenic non-human animals, in particular mice, can in a particular preferred embodiment also be used for determining differences between an Aβ peptide starting with an N-terminal Q or Aβ peptide starting with an N-terminal E. In view of AβN3Q being a better substrate for QC than AβN3E, this allows conclusions regarding the role of QC in Aβ peptide-related diseases in an advantageous fashion.

The agents selected by the above-described screening methods can work by decreasing the effects of Aβ peptide (negative effectors, inhibitors), or by increasing the effects of Aβ peptide (positive effectors, activators).

In one embodiment of the present invention, inhibitors of the effects of Aβ peptide are preferred.

The compounds of the present invention can be converted into acid addition salts, especially pharmaceutically acceptable acid addition salts.

The salts of the compounds of the invention may be in the form of inorganic or organic salts.

The compounds of the present invention can be converted into and used as acid addition salts, especially pharmaceutically acceptable acid addition salts. The pharmaceutically acceptable salt generally takes a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. All pharmaceutically acceptable acid addition salt forms of the compounds of the present invention are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

In a further embodiment, the present invention provides a method of preventing or treating a condition characterized or mediated by Aβ peptide in a subject in need thereof which comprises administering any of the compounds of the present invention or pharmaceutical compositions thereof in a quantity and dosing regimen therapeutically effective to treat the condition. Additionally, the present invention includes the use of the compounds of this invention, and their corresponding pharmaceutically acceptable acid addition salt forms, for the preparation of a medicament for the prevention or treatment of a condition characterized or mediated by Aβ peptide in a subject. The compound may be administered to a patient by any conventional route of administration, including, but not limited to, intravenous, oral, subcutaneous, intramuscular, intradermal, parenteral and combinations thereof.

In a further preferred form of implementation, the invention relates to pharmaceutical compositions, that is to say, medicaments, that contain at least one compound of the invention or salts thereof, optionally in combination with one or more pharmaceutically acceptable carriers and/or solvents.

The pharmaceutical compositions may, for example, be in the form of parenteral or enteral formulations and contain appropriate carriers, or they may be in the form of oral formulations that may contain appropriate carriers suitable for oral administration. Preferably, they are in the form of oral formulations.

The effectors administered according to the invention may be employed in pharmaceutically administrable formulations or formulation complexes as inhibitors or in combination with inhibitors, substrates, pseudosubstrates, inhibitors of QC expression, binding proteins or antibodies of those enzyme proteins that reduce the QC protein concentration in mammals. The compounds of the invention make it possible to adjust treatment individually to patients and diseases, it being possible, in particular, to avoid individual intolerances, allergies and side-effects.

The compounds also exhibit differing degrees of activity as a function of time. The physician providing treatment is thereby given the opportunity to respond differently to the individual situation of patients: he is able to adjust precisely, on the one hand, the speed of the onset of action and, on the other hand, the duration of action and especially the intensity of action.

A preferred treatment method according to the invention represents a new approach for the prevention or treatment of a condition characterized or mediated by Aβ peptide in mammals. It is advantageously simple, susceptible of commercial application and suitable for use, especially in the treatment of diseases that are based on unbalanced concentration of physiological active Aβ peptide in mammals and especially in human medicine.

The compounds may be advantageously administered, for example, in the form of pharmaceutical preparations that contain the active ingredient in combination with customary additives like diluents, excipients and/or carriers known from the prior art. For example, they can be administered parenterally (for example i.v. in physiological saline solution) or enterally (for example orally, formulated with customary carriers).

Depending on their endogenous stability and their bioavailability, one or more doses of the compounds can be given per day in order to achieve the desired normalisation of the blood glucose values. For example, such a dosage range in humans may be in the range of from about 0.01 mg to 250.0 mg per day, preferably in the range of about 0.01 to 100 mg of compound per kilogram of body weight.

By administering the effectors to a mammal it could be possible to prevent or alleviate or treat conditions selected from Mild Cognitive Impairment, Alzheimer's disease, Down Syndrome, Familial Danish Dementia, Familial British Dementia, Huntington's Disease, ulcer disease and gastric cancer with or w/o *Helicobacter pylori* infections, pathogenic psychotic conditions, schizophrenia, infertility, neoplasia, inflammatory host responses, cancer, psoriasis, rheumatoid arthritis, atherosclerosis, restenosis, lung fibrosis, liver fibrosis, renal fibrosis, graft rejection, acquired immune deficiency syndrome, impaired humoral and cell-mediated immune responses, leukocyte adhesion and migration processes in the endothelium, impaired food intake, sleep-wakefulness, impaired homeostatic regulation of energy metabolism, impaired autonomic function, impaired hormonal balance and impaired regulation of body fluids.

Further, by administering the effectors to a mammal it could be possible to stimulate gastrointestinal tract cell proliferation, preferably proliferation of gastric mucosal cells, epithelial cells, acute acid secretion and the differentiation of acid producing parietal cells and histamine-secreting enterochromaffin-like cells.

In addition, administration of the inhibitors to mammals may lead to a loss of sperm cell function thus suppressing male fertility. Thus, the present invention provides a method for the regulation and control of male fertility and the use of activity lowering effectors for the preparation of contraceptive medicaments for males.

Furthermore, by administering the effectors to a mammal it may be possible to suppress the proliferation of myeloid progenitor cells.

The compounds used according to the invention can accordingly be converted in a manner known per se into conventional formulations, such as, for example, tablets, capsules, dragées, pills, suppositories, granules, aerosols, syrups, liquid, solid and cream-like emulsions and suspensions and solutions, using inert, non-toxic, pharmaceutically suitable carriers and additives or solvents. In each of those formulations, the therapeutically effective compounds are preferably present in a concentration of approximately from 0.1 to 80% by weight, more preferably from 1 to 50% by weight, of the total mixture, that is to say, in amounts sufficient for the mentioned dosage latitude to be obtained.

The substances can be used as medicaments in the form of dragées, capsules, bitable capsules, tablets, drops, syrups or also as suppositories or as nasal sprays.

The formulations may be advantageously prepared, for example, by extending the active ingredient with solvents and/or carriers, optionally with the use of emulsifiers and/or dispersants, it being possible, for example, in the case where water is used as diluent, for organic solvents to be optionally used as auxiliary solvents.

Examples of excipients useful in connection with the present invention include: water, non-toxic organic solvents, such as paraffins (for example natural oil fractions), vegetable oils (for example rapeseed oil, groundnut oil, sesame oil), alcohols (for example ethyl alcohol, glycerol), glycols (for example propylene glycol, polyethylene glycol); solid carriers, such as, for example, natural powdered minerals (for example highly dispersed silica, silicates), sugars (for example raw sugar, lactose and dextrose); emulsifiers, such as non-ionic and anionic emulsifiers (for example polyoxyethylene fatty acid esters, polyoxyethylene fatty alcohol ethers, alkylsulphonates and arylsulphonates), dispersants (for example lignin, sulphite liquors, methylcellulose, starch and polyvinylpyrrolidone) and lubricants (for example magnesium stearate, talcum, stearic acid and sodium lauryl sulphate) and optionally flavourings.

Administration may be carried out in the usual manner, preferably enterally or parenterally, especially orally. In the case of enteral administration, tablets may contain in addition to the mentioned carriers further additives such as sodium citrate, calcium carbonate and calcium phosphate, together with various additives, such as starch, preferably potato starch, gelatine and the like. Furthermore, lubricants, such as magnesium stearate, sodium lauryl sulphate and talcum, can be used concomitantly for tabletting. In the case of aqueous suspensions and/or elixirs intended for oral administration, various taste correctives or colourings can be added to the active ingredients in addition to the above-mentioned excipients.

In the case of parenteral administration, solutions of the active ingredients using suitable liquid carriers can be employed. In general, it has been found advantageous to administer, in the case of intravenous administration, amounts of approximately from 0.01 to 2.0 mg/kg, preferably approximately from 0.01 to 1.0 mg/kg, of body weight per day to obtain effective results and, in the case of enteral administration, the dosage is approximately from 0.01 to 2 mg/kg, preferably approximately from 0.01 to 1 mg/kg, of body weight per day.

It may nevertheless be necessary in some cases to deviate from the stated amounts, depending upon the body weight of the experimental animal or the patient or upon the type of administration route, but also on the basis of the species of animal and its individual response to the medicament or the interval at which administration is carried out. Accordingly, it may be sufficient in some cases to use less than the above-mentioned minimum amount, while, in other cases, the mentioned upper limit will have to be exceeded. In cases where relatively large amounts are being administered, it may be advisable to divide those amounts into several single doses over the day. For administration in human medicine, the same dosage latitude is provided. The above remarks apply analogously in that case.

For examples of pharmaceutical formulations, specific reference is made to the examples of WO 2004/098625, pages 50-52, which are incorporated herein by reference in their entirety.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The above disclosure describes the present invention in general. A more complete understanding can be obtained by reference to the following examples. These examples are described solely for purposes of illustration and are not intended to limit the scope of the invention. Although specific terms have been employed herein, such terms are intended in a descriptive sense and not for purposes of limitation. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Reference Example 1

Preparation of Human and Papaya QC

Host Strains and Media

Pichia pastoris strain X33 (AOX1, AOX2), used for the expression of human QC was grown, transformed and analyzed according to the manufacturer's instructions (Invitrogen). The media required for P. pastoris, i.e. buffered glycerol (BMGY) complex or methanol (BMMY) complex medium, and the fermentation basal salts medium were prepared according to the manufacturer's recommendations.

Molecular Cloning of Plasmid Vectors Encoding the Human QC

All cloning procedures were done applying standard molecular biology techniques. For expression in yeast, the vector pPICZαB (Invitrogen) was used. The pQE-31 vector (Qiagen) was used to express the human QC in *E. coli*. The cDNA of the mature QC starting with codon 38 was fused in frame with the plasmid encoded 6x histidine tag. After amplification utilizing the primers pQCyc-1 and pQCyc-2 (WO 2004/098625) and subcloning, the fragment was inserted into the expression vector employing the restriction sites of SphI and HindIII.

Transformation of *P. pastoris* and mini-scale expression

Plasmid DNA was amplified in *E. coli* JM109 and purified according to the recommendations of the manufacturer (Qiagen). In the expression plasmid used, pPICZαB, three restriction sites are provided for linearization. Since SacI and BstXI cut within the QC cDNA, PmeI was chosen for linearization. 20-30 μg plasmid DNA was linearized with PmeI, precipitated by ethanol, and dissolved in sterile, deionized water. 10 μg of the DNA was then applied for transformation of competent *P. pastoris* cells by electroporation according to the manufacturer's instructions (BioRad). Selection was done an plates containing 150 μg/ml Zeocin. One transformation using the linearized plasmid yielded several hundred transformants.

In order to test the recombinant yeast clones for QC expression, recombinants were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h up to 72 h. Subsequently, QC activity in the supernatant was determined. The presence of the fusion protein was confirmed by western blot analysis using an antibody directed against the 6x histidine tag (Qiagen). Clones that displayed the highest QC activity were chosen for further experiments and fermentation.

Large-Scale Expression in a Fermenter

Expression of the QC was performed in a 5 l reactor (Biostat B, B. Braun biotech), essentially as described in the "*Pichia* fermentation process guidelines" (Invitrogen). Briefly, the cells were grown in the fermentation basal salts medium supplemented with trace salts, and with glycerol as the sole carbon source (pH 5.5). During an initial batch phase for about 24 h and a subsequent fed-batch phase for about 5 h, cell mass was accumulated. Once a cell wet weight of 200 g/l was achieved, induction of QC expression was performed using methanol applying a three-step feeding profile for an entire fermentation time of approximately 60 h. Subsequently, cells were removed from the QC-containing supernatant by centrifugation at 6000×g, 4° C. for 15 min. The pH was adjusted to 6.8 by addition of NaOH, and the resultant turbid solution was centrifuged again at 37000×g, 4° C. for 40 min. In cases of continued turbidity, an additional filtration step was applied using a cellulose membrane (pore width 0.45 μm).

Purification of 6x Histidine Tagged QC Expressed in *P. pastoris*

The His-tagged QC was first purified by immobilized metal affinity chromatography (IMAC). In a typical purification, 1000 ml of culture supernatant were applied to a $Ni^{2+}$-loaded Chelating Sepharose FF column (1.6×20 cm, Pharmacia), that was equilibrated with 50 mM phosphate buffer, pH 6.8, containing 750 mM NaCl, at a flow rate of 5 ml/min. After washing with 10 column volumes of equilibration buffer and 5 column volumes of equilibration buffer containing 5 mM histidine, the bound protein was eluted by a shift to 50 mM phosphate buffer, pH 6.8, containing 150 mM NaCl and 100 mM histidine. The resulting eluate was dialyzed against 20 mM Bis-Tris/HCl, pH 6.8, at 4° C. overnight. Subsequently, the QC was further purified by anion exchange chromatography an a Mono Q6 column (BioRad), equilibrated with dialysis buffer. The QC-containing fraction was loaded onto the column using a flow rate of 4 ml/min. The column was then washed with equilibration buffer containing 100 mM NaCl. The elution was performed by two gradients resulting in equilibration buffer containing 240 mM and 360 mM NaCl in 30 or 5 column volumes, respectively. Fractions of 6 ml were collected and the purity was analyzed by SDS-PAGE. Fractions containing homogenous QC were pooled and concentrated by ultrafiltration. For long-term storage (−20° C.), glycerol was added to a final concentration of 50%. Protein was quantified according to the methods of Bradford or Gill and von Hippel (Bradford, M. M. 1976 Anal Biochem 72, 248-254; Gill, S. C. and von Hippel, P.H.1989 Anal Biochem 182, 319-326.).

Expression and Purification of QC in *E. coli*

The construct encoding the QC was transformed into M15 cells (Qiagen) and grown an selective LB agar plates at 37° C. Protein expression was carried out in LB medium containing 1% glucose and 1% ethanol at room temperature. When the culture reached an $OD_{600}$ of approximately 0.8, expression was induced with 0.1 mM IPTG overnight. After one cycle of freezing and thawing, cells were lysed at 4° C. by addition of 2.5 mg/ml lysozyme in 50 mM phosphate buffer, pH 8.0, containing 300 mM NaCl and 2 mM histidine for approximately 30 min. The solution was clarified by centrifugation at 37000×g, 4° C. for 30 min, followed by a filtration applying a glass frit (DNA separation) and two additional filtration steps applying cellulose filters for crude and fine precipitates. The supernatant (approx. 500 ml) was applied onto a $Ni^{2+}$-affinity column (1.6×20 cm) at a flow rate of 1 ml/min. Elution of QC was carried out with 50 mM phosphate buffer containing 150 mM NaCl and 100 mM histidine. The QC-containing fraction was concentrated by ultrafiltration.

Purification of OC from Papaya Latex

QC from papaya latex was prepared using the BioCAD 700E (Perseptive Biosystems, Wiesbaden, Germany) with a modified version of a previously reported method (Zerhouni, S. et al. 1989 Biochim Biophys Acta 138, 275-290). 50 g latex was dissolved in water and centrifugated as described therein. Inactivation of proteases was performed with S-methyl methane thiosulfonate, and the resultant crude extract was dialyzed. After dialysis, the entire supernatant was loaded onto a (21×2.5 cm i.d.) SP Sepharose Fast Flow column, equilibrated with 100 mM sodium acetate buffer, pH 5.0 (flow rate 3 ml/min). Elution was performed in three steps by increasing sodium acetate buffer concentration at a flow rate of 2 ml/min. The first step was a linear gradient from 0.1 to 0.5 M acetate buffer in 0.5 column volumes. The second step was a linear increase in buffer concentration from 0.5 to 0.68 M in four column volumes. During the last elution step, one column volume of 0.85 M buffer was applied. Fractions (6 ml) containing the highest enzymatic activity were pooled. Concentration and buffer changes to 0.02 M Tris/HCl, pH 8.0 were performed via ultrafiltration (Amicon; molecular mass cut-off of the membrane 10 kDa).

Ammonium sulfate was added to the concentrated papaya enzyme, obtained from the ion exchange chromatography step to a final concentration of 2 M. This solution was applied onto a (21×2.5 cm i.d.) Butyl Sepharose 4 Fast Flow column (flow rate 1.3 ml/min), equilibrated with 2 M ammonium sulfate, 0.02 M Tris/HCl, pH 8.0. Elution was performed in three steps with decreasing concentrations of ammonium sulfate. During the first step a linear gradient from 2 to 0.6 M ammonium sulfate, 0.02 M Tris/HCl, pH 8.0 was applied for 0.5 column volumes at a flow rate of 1.3 ml/min. The second step was a linear gradient from 0.6 to 0 M ammonium sulfate, 0.02 M Tris/HCl, pH 8.0, in 5 column volumes at a flow rate of 1.5 ml/min. The last elution step was carried out by applying 0.02 M Tris/HCl at pH 8.0 for 2 column volumes at a flow rate of 1.5 ml/min. All fractions containing QC activity were pooled and concentrated by ultrafiltration. The resultant homogenous QC was stored at −70° C. Final protein concentrations were determined using the method of Bradford, compared to a standard curve obtained with bovine serum albumin.

Reference Example 2

Assays for Glutaminyl Cyclase Activity

Fluorometric Assays

Measurements were performed with a BioAssay Reader HTS-7000Plus (Perkin Eimer) or a Novo Star (BMG Labtechnologies) reader for microplates at 30° C. QC activity was evaluated fluorometrically using H-Gln-PNA. The samples consisted of 0.2 mM fluorogenic substrate, 0.25 U pyroglutamyl aminopeptidase (Unizyme, Horsholm, Denmark) in 0.2 M Tris/HCl, pH 8.0 containing up to 20 mM EDTA and an appropriately diluted aliquot of QC in a final volume of 250 µl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 µmol pGlu-PNA from H-Gln-PNA per minute under the described conditions.

In a second fluorometric assay, QC was activity was determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit software.

Spectrophotometric Assay of QC

This novel assay was used to determine the kinetic parameters for most of the QC substrates. QC activity was analyzed spectrophotometrically using a continuous method, that was derived by adapting a previous discontinuous assay (Bateman, R. C. J. 1989 J Neurosci Methods 30, 23-28) utilizing glutamate dehydrogenase as auxiliary enzyme. Samples consisted of the respective QC substrate, 0.3 mM NADH, 14 mM α-ketoglutaric acid and 30 U/ml glutamate dehydrogenase in a final volume of 250 µl. Reactions were started by addition of QC and pursued by monitoring of the decrease in absorbance at 340 nm for 8-15 min.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except for the putative inhibitory compound added. For a rapid test of QC-inhibition, samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Reference Example 3

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals were recorded and filtered using LeCroy 9350M digital storage oscilloscope linked to a personal computer. Samples (5 µl) were mixed with equal volumes of the matrix solution. For matrix solution we used DHAP/DAHC, prepared by solving 30 mg 2′,6′-dihydroxyacetophenone (Aldrich) and 44 mg diammonium hydrogen citrate (Fluka) in 1 ml acetonitrile/ 0.1% TFA in water (1/1, v/v). A small volume (≈1 µl) of the matrix-analyte-mixture was transferred to a probe tip and immediately evaporated in a vacuum chamber (Hewlett-Packard G2024A sample prep accessory) to ensure rapid and homogeneous sample crystallization.

For long-term testing of $Glu^1$-cyclization, Aβ-derived peptides were incubated in 100 µl 0.1 M sodium acetate buffer, pH 5.2 or 0.1 M Bis-Tris buffer, pH 6.5 at 30° C. Peptides were applied in 0.5 mM [Aβ3-11 a] or 0.15 mM [Aβ3-21a] concentrations, and 0.2 U QC was added all 24 hours. In case of Aβ3-21a, the assays contained 1% DMSO. At different times, samples were removed from the assay tube, peptides extracted using ZipTips (Millipore) according to the manufacturer's recommendations, mixed with matrix solution (1:1 v/v) and subsequently the mass spectra recorded. Negative controls contained either no QC or heat deactivated enzyme. For the inhibitor studies the sample composition was the same as described above, with exception of the inhibitory compound added (5 mM benzimidazole or 2 mM 1,10-phenanthroline).

Reference Example 4

Murine QPCT

Cloning of Murine QC

The primers for isolation of the open reading frame of mQC were designed using PubMed nucleotide entry AK017598, encoding the putative mQC. The primer sequences were as follows: sense 5 ATATGCATGCATG-GCAGGCAGCGAAGACAAGC (SEQ ID No:35); antisense, and 5 ATATAAGCTTTTACAAGTGAAGATATTC-CAACACAAAGAC (SEQ ID No:36). Total RNA was isolated from murine insulinoma cell line β-TC 3 cells using the RNeasy Mini Kit (Qiagen) and reversely transcribed by SuperScriptII (Invitrogen). Subsequently, mQC cDNA was amplified on a 1:12.5 dilution of generated product in a 50 µl reaction with Herculase Enhanced DNA-Polymerase (Stratagene), inserted into the PCR Script CAM Cloning vector (Stratagene) and verified by sequencing. The cDNA fragment encoding the mature mQC was amplified using the primers 5 ATACTCGAGAAAAGAGCCTGGACGCAGGAGAAG (SEQ ID No:37) (XhoI, sense) and 5 ATATCTAGATTA- CAAGTGAAGATATTCCAAC (SEQ ID No:38) (XbaI, antisense). The digested fragment was ligated into the vector pPICZαB, propagated in E. coli and verified by sequencing of the sense and antisense strand. Finally, the expression plasmid was linearized using PmeI, precipitated, and stored at −20° C.

Transformation of P. pastoris and Mini-Scale Expression of Murine QC 1-2 μg of plasmid DNA were applied for transformation of competent P. pastoris cells by electroporation according to the manufacturer's instructions (BioRad). Selection was done on plates containing 100 μg/ml Zeocin. In order to test the recombinant yeast clones upon mQC expression, recombinants were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h for about 72 h. Subsequently, QC activity in the supernatant was determined. Clones that displayed the highest activity were chosen for further experiments and fermentation.

Large Scale Expression and Purification of Murine QC

The expression of mQC was performed in a 5 L reactor (Biostad B, B. Braun biotech, Melsungen, Germany). Fermentation was carried out in basal salts medium supplemented with trace salts at pH 5.5. Initially, biomass was accumulated in a batch and a fed batch phase with glycerol as the sole carbon source for about 28 h. Expression of mQC was initiated by methanol feeding according to a three-step profile recommended by Invitrogen for an entire fermentation time of approximately 65 h. Subsequently, cells and turbidity were removed from the mQC-containing supernatant by two sequential centrifugation steps at 6000×g and 38000×g for 15 min and 4 h, respectively. For purification, the fermentation broth was diluted with water to a conductivity of about 5 mS/cm and applied in reversed flow direction (15 mL/min) onto a Streamline SP XL column (2.5×100 cm), equilibrated with 0.05 M phosphate buffer, pH 6.4. After a washing step in reversed flow direction with equilibration buffer for 2 column volumes, proteins were eluted at a flow rate of 8 mL/min using 0.15 M Tris buffer, pH 7.6, containing 1.5 M NaCl in forward direction. QC-containing fractions were pooled and ammonium sulfate added to a final concentration of 1 M. The resulting solution was applied onto a Butyl Sepharose FF column (1.6×13 cm) at a flow rate of 4 mL/min. Bound mQC was washed with 0.05 M phosphate buffer, pH 6.8 containing 0.75 M ammonium sulfate for 5 column volumes and eluted in reversed flow direction with 0.05 M phosphate buffer, pH 6.8. The fractions containing mQC were pooled and desalted overnight by dialysis against 0.025 M Tris, pH 7.5. Afterwards, the pH was adjusted to 8.0 by addition of NaOH and applied (4.0 mL/min) onto an Uno Q column (Bio Rad), equilibrated with 0.02 M Tris, pH 8.1. After a washing step using equilibration buffer, mQC was eluted using the same buffer containing 0.18 M NaCl. Fractions exhibiting QC activity were pooled and the pH adjusted to 7.4 by addition of 1 M Bis-Tris buffer, pH 6.0. mQC was stable at 4° C. for up to 1 month. For long-term storage at −20° C., 50% glycerol was added.

Example 1

Production of Transgenic Mice

Transgenic Mice

The generation of murine thyrotropin-releasing hormone—Aβ fusion proteins mTRH-Aβ(N3E-42) and mTRH (N3Q-42) was essentially as described elsewhere (Cynis, H., et al. Inhibition of glutaminyl cyclase alters pyroglutamate formation in mammalian cells, Biochim Biophys Acta 1764, 1618-1625 (2006)). The respective cDNAs were inserted into vector pUC18 containing the murine Thy-1 sequence applying standard molecular biology techniques. Murine QC was isolated from insulinoma cell line β-TC 3. The mQC cDNA was cloned into vector pTG-CAG. All constructs were verified by sequencing. The transgenic mice were generated by male pronuclear injection of fertilized C57B16 oocytes (PNI, generated by genoway, Lyon, France). The injected oocytes were then implanted into foster mothers for full term development. The resulting offspring (3 founders of each line) were further characterized for transgene integration by PCR analysis and after crossing to C57B16 wildtype mice for transgene expression by RT-PCR (n=3-5 each line). The line with highest transgene mRNA expression was selected for further breeding and cross-breeding experiments (named tgN3E-42×QC mice). tgN3E-42×QC transgenic appeared healthy and showed no evidence for neurological abnormalities. Only 1 of the 3 founders of the tgN3Q-42 PNI gave birth to offspring (tgN3Q-42 mouse model). However, one of the infertile founders showed neuron loss and neuronal immunoreactivity for Aβ(N3pGlu) at 7 months of age within the hippocampal CA1 layer, which was also observed with the offspring of other founder. The observation of the identical phenotype in the this founder and in the offspring of the other founder clearly suggests that the observed phenotype is not due to an integration effect. All animals were handled according to German guidelines for animal care.

Preparation of the DNA Construct

The quality of the cDNA construct was verified and confirmed by running an aliquot on an agarose gel and no trace of degradation was observed. Finally, restriction analysis using diagnostic BglI, EcoRI, and HindIII restriction enzymes yielded the expected restriction profiles. The TBA-Tg plasmids were digested by EcoRI and the 7170-bp fragment containing the transgene was isolated from the vector backbone. The 7.1 kb transgenic construct fragment was further purified and diluted before injection into fertilized oocytes. The purity and concentration of the isolated transgene were verified by agarose gel electrophoresis.

PCR Genotyping Strategy

The screening for detection of the random integration of the transgene was achieved by PCR amplification. Two PCRs were designed (see FIG. 7):

PCR1 is designed to efficiently detect the transgene random integration event. The selected primer pair allows the amplification of a short DNA sequence within the transgene sequence, yielding a specific 505-bp PCR product.

PCR2 is designed to assess the integrity of the transgene integration event. The selected primer pair allows the amplification of a DNA sequence extending from 5' region of promoter and 3' region of Thy1 gene yielding a specific 6279-bp PCR product. As the Thy1 promoter cassette is derived from mouse genomic sequence, the PCR screen, used to investigate the integrity of the transgene integrity, also lead to the amplification of a 7413-bp product from the endogenous Thy1 gene.

TABLE 1

PCR genotyping tgN3E-42 and tgN3Q-42 transgenic mice

| Primer name | Primer sequence 5'-3' | expected PCR size |
|---|---|---|
| GX3425 | 5'-AGTAATGAAGTCACCCAGCAGGGAGG-3' (SEQ ID No: 39) | 505 bp |
| GX3426 | 5'-TGATCCAGGAATCTAAGGCAGCACC-3' (SEQ ID No: 40) | |

These tests were performed to monitor the specificity of the primers and the sensitivity of the PCR reaction. Once established, these PCR conditions were used to screen the F0 generation (founder animals).

TABLE 2

Protocol for genotyping tgN3E-42 and tgN3Q-42 transgenic mice by PCR

| Reaction mix | | Reaction step | Temp/time | cycles |
|---|---|---|---|---|
| Genomic mouse DNA | 10 ng | | | |
| Primer | 2.5 pmol | denaturing | 94° C./180 s | 1x |
| dNTPs | 20 µM | denaturing | 94° C./45 s | 35x |
| 10 x Reaction buffer | 1 µl | annealing | 58°/60 s | 35x |
| MgCl₂ | 2 mM | extension | 72° C./60 s | 35x |
| Taq polymerase | 0.5 U | completion | 72° C./300 s | 1x |
| Reaction volume | 10 µl | | | |

Protocol for the Determination of the Relative Transgene Copy Numbers

TABLE 3

Real-Time PCR to determine the relative transgene copy numbers in tgN3E-42 and tgN3Q-42 transgenic mice

| Primer name | Primer sequence 5'-3' | expected PCR size |
|---|---|---|
| A(3-42-for | 5'-TTGAGGAAAGACCTCCAGC-3' (SEQ ID No: 43) | 168 bp |
| A(3-42-rev | 5'-CATGAGTCCAATGATTGCACC-3' (SEQ ID No: 44) | |

Equimolar amounts of chromosomal DNA from the analyzed transgenic animals were used as template and Real-Time PCR was performed using the fluorescent dye SYBR-Green I according to the following protocol:

TABLE 4

Protocol for Real-Time PCR in tgN3E-42 and tgN3Q-42 transgenic mice

| Reaction mix | | Reaction step | Temp/time | Cycles |
|---|---|---|---|---|
| genomic DNA | 20 ng | | | |
| Primer | 15 pmol | denaturing | 95° C./600 s | 1x |
| 2x Reaction Mix | 12.5 µl | denaturing | 94° C./15 s | 40x |
| SYBR-Green I | 0.5 µl | annealing | 55°/30 s | 40x |
| H2O | 8 µl | extension | 72° C./30 s | 40x |
| Reaction volume | 25 µl | Melting Curve | 55° C.-95° C./30 s | 1x |

TABLE 5

PCR for genotyping transgenic mice expressing mQC

| Primer name | Primer sequence 5'-3' | expected PCR size |
|---|---|---|
| mQC3 | 5'-GCCACGGATTCAGCTGTGTGC-3' (SEQ ID No: 41) | 302 bp |
| mQC4 | 5'-GAATGTTGGATTTGCTGCTC-3' (SEQ ID No: 42) | |

These tests were performed to monitor the specificity of the primers and the sensitivity of the PCR reaction. Once established, these PCR conditions were used to screen the F0 generation (founder animals).

TABLE 6

Protocol for genotyping transgenic mice expressing mQC by PCR

| Reaction mix | | Reaction step | | |
|---|---|---|---|---|
| Genomic mouse DNA | 10 ng | | | |
| Primer | 10 pmol | denaturing | 94° C./180 s | 1x |
| dNTPs | 20 µM | denaturing | 94° C./45 s | 35x |
| 10 x Reaction buffer | 0.1 vol | annealing | 58°/60 s | 35x |
| MgCl₂ | 2 mM | extension | 72° C./60 s | 35x |
| Taq polymerase | 0.5 U | completion | 72° C./300 s | 1x |
| Reaction volume | 10 µl | | | |

Protocol for mRNA Quantification by RT-PCR

TABLE 7

Real-Time PCR for mRNA quantification in tgN3E-42 and tgN3Q-42 transgenic mice

| Primer name | Primer sequence 5'-3' | expected PCR size |
|---|---|---|
| Aβ3-42-for | 5'-TTGAGGAAAGACCTCCAGC-3' (SEQ ID No: 43) | 168 bp |
| Aβ3-42-rev | 5'-CATGAGTCCAATGATTGCACC-3' (SEQ ID No: 44) | |

1 µg of total RNA was reverse transcribed and Real-Time PCR was performed using the fluorescent dye SYBR-Green I according to the following protocol:

TABLE 8

Protocol for Real-Time PCR in tgN3E-42 and tgN3Q-42 transgenic mice

| Reaction mix | | Reaction step | Temp/time | Cycles |
|---|---|---|---|---|
| cDNA | 1 µl (1:5 Dilution) | | | |
| Primer | 15 pmol | denaturing | 95° C./600 s | 1x |
| 2x Reaction Mix | 12.5 µl | denaturing | 94° C./15 s | 40x |
| SYBR-Green I | 0.5 µl | annealing | 55°/30 s | 40x |
| H₂O | 8 µl | extension | 72° C./30 s | 40x |
| Reaction volume | 25 µl | Melting Curve | 55° C.-95° C./30 s | 1x |

Immunohistochemistry and Histology

Mice were anaesthetized and transcardially perfused with ice-cold phosphate-buffered saline (PBS) followed by 4% paraformaldehyde. Brain samples were carefully dissected and post-fixed in 4% phosphate-buffered formalin at 4° C. Immunohistochemistry was performed on 4 µm paraffin sections. The following antibodies were used: 4G8 (A1317-24, Signet), GFAP (Chemicon), Iba1 (Waco), ubiquitin (DAKO) and against Aβ with pyroglutamate at position 3 (Saido, T. C., et al. Dominant and differential deposition of distinct beta-amyloid peptide species, Abeta N3(pE), in senile plaques, Neuron 14, 457-466 (1995)). Biotinylated secondary anti-rabbit and anti-mouse antibodies (1:200) were purchased from DAKO. Staining was visualized using the ABC method, with a Vectastain kit (Vector Laboratories) and diaminobenzidine as chromogen. Counterstaining was carried out with hematoxylin. For fluorescent stainings AlexaFluor488- and AlexaFluor594-conjugated antibodies (Molecular Probes) were used.

For the analysis of tgN3E-42 mice additionally the following antibodies were used for immunohistochemical characterization: Aβ/4G8 (Acris), Aβ/6E10 (Calbiochem), Aβ-N3pGlu-42(clone6), GFAP (DAKO), NeuN (Chemicon). Biotinylated secondary anti-rabbit and anti-mouse antibodies (1:250) were purchased from Vector Laboratories. Staining was visualized using the ABC method, with a Vectastain kit (Vector Laboratories) and diaminobenzidine as chromogen. For fluorescent stainings Cy2- and Cy3-conjugated secondary antibodies (Dianova) were used. DAPI nucleic acid staining (Molecular Probes) was performed on fluorescent immunostainings.

Quantification of Aβ (x-42) and Aβ(N3pGlu-42) by ELISA

Brains were weighed in a frozen state and directly homogenized in a Dounce-homogenizer in 2.5 ml 2% SDS, containing complete protease inhibitor (Roche). Homogenates were sonified for 30 s and subsequently centrifuged at 80.000 g for 1 min at 4° C. Supernatants were taken and directly frozen at −80° C. The resulting pellets were resuspended in 0.5 ml 70% formic acid (FA) and sonified for 30 s. Formic acid was neutralized with 9.5 ml 1 M and aliquots were directly frozen at −80° C. SDS lysates were used in a 10-fold dilution for both Aβ(x-42) and Aβ(N3pGlu) ELISA measurements. Formic acid lysates were used in a 10× dilution for the Aβ(x-42) measurement. For Aβ(N3pGlu-42) measurements undiluted FA lysates were applied. ELISA measurements were performed according to the protocol of the manufacturer (IBL Co., Ltd. Japan). For statistical analyses, Aβ (x-42) and Aβ (N3pGlu) concentrations resulting from SDS— and FA-extractions were cumulated.

Western Blot Analysis Aβ (x-42) and Aβ(N3pGlu-42)

The electrophoretic separation of N-terminally modified Aβ peptides was performed applying 15% urea-PAGE gel as described elsewhere (Klafki, H. W., Wiltfang, J. & Staufenbiel, M. (1996) Anal. Biochem. 237, 24-29).

Proteins were transferred to a nitrocellulose membrane (Roth) under semi-dry conditions. Subsequently, the membrane was blocked using 3% (w/v) dry milk in TBS-T (20 mM Tris/HCl; pH 7.5; 500 mM NaCl, 0.05% (v/v) Tween20). Aβ peptides were detected using the monoclonal anti-Aβ(1-16) antibody 6E10 (Chemicon). For visualization, blot membranes were incubated with secondary anti-mouse antibody, conjugated to horseradish peroxidase (Cell Signaling) in TBS-T containing 5% (w/v) dry milk and subsequently developed using the SuperSignal West Pico System (Pierce) according to the manufacturer's protocol.

Statistical Analysis

Differences between groups were tested with one-way analysis of variance (ANOVA) followed by unpaired t-tests. All data were given as means±s.e.m. Significance levels of unpaired t-tests were given as follows: *$P<0.001$; $P<0.01$; *$P<0.05$. Survival rate was calculated by the Logrank Test. All calculations were performed using GraphPad Prism version 4.03 for Windows (GraphPad Software, San Diego, Calif., USA).

Example 2

Behavioural Tests

Primary screen: The primary screen utilizes standard methods to provide a behavioral and functional profile by observational assessment (Rogers D. C. et al., 1997. Behavioral and functional analysis of mouse phenotype: SHIRPA, a proposed protocol for comprehensive phenotype assessment. *Mamm Genome*, 8:711-713). Using a modified SHIRPA protocol general health and specific functions that could interfere with further behavioral testing (muscle and lower motor neurone functions, spinocerebellar, sensory, neuropsychiatric and autonomic functions) were examined in a high throughput screen.

The assessment began with observing social behavior in the home cage ("home cage observation") and subsequently undisturbed behavior of single animals in a clear Plexiglas arena for 90 seconds ("individual observation"). This monitoring of mouse behavior was followed by a battery of short tests for further characterisation: acoustic startle reflex, hanging behavior, visual placing, falling behavior, righting reflex, postural reflex, negative geotaxis, hanging wire, ear twitch, whiskers twitch and eye blink. At last the animal was grasped in the neck and examined for dysmorphological abnormalities. To complete the assessment the animal was weighed and then transferred back into its home cage.

Fear Conditioning:

To study contextual and cued fear reflexes in mice the commercialized, computer-controlled "Fear Conditioning System (FCS)" (TSE Systems, Bad Homburg, Germany) was used.

The experimental settings were chosen following the protocol of Oliver Stiedl (Stiedl O. et al., 2004 Behavioral and autonomic dynamics during contextual fear conditioning in mice. Auton Neurosci. Basic and Clinical 115(1-2):15-27). Investigations in the FCS were performed on two consecutive days and were divided into three phases:

Phase 1 (training/conditioning trial): Training was performed in a clear acrylic compartment within a constantly illuminated (~300 lx) fear conditioning box. A loudspeaker provided a constant, white background noise (68 db SPL). After a pause of 270 s the mouse was given an auditory cue (10 kHz, 75 dB SPL) for 30 s (conditioned stimulus). The 2 s footshock (0.7 mA, constant current; unconditioned stimulus) was administered for the final 2 s of the sound. Mice were returned to their home cages 30 s after shock termination.

Phase 2 (contextual retention): 24 h after training (Phase 1) animals were re-exposed to the original context and behavior was monitored for 270 s.

Phase 3 (tone-dependent retention): Memory for the conditioned stimulus (sound) was tested 1 h after Phase 2 in a novel context (similarly sized black acrylic box, reduced light intensity due to the black color, plane floor plate instead of shock grid). After 270 s of free exploration in novel context the same sound as in Phase 1 was applied for 180 s and behavior was automatically recorded by the FCS.

Dark Light Box:

Automated assessment of exploratory activity in the dark <-> light exploration model (Crawley J. N. (2007) What's Wrong With My Mouse: Anxiety-Related Behaviors. Wiley, Second Edition, 240-241) was conducted with dark-light-box insert modules for the PhenoMaster apparatus (TSE Systems, Bad Homburg, Germany). Insert modules consisted of a Plexiglas chamber unequally divided into two compartments (one-third to two-thirds of the chamber) by a black Plexiglas box containing a small alleyway. The larger compartment was open and brightly illuminated, while the small compartment was closed and dark. Animals were placed individually in the brightly lit compartment and were allowed to freely explore the two compartments for 10 minutes. A grid of photocells automatically detected activity of the mouse (number of transitions between the two compartments, time spend in each compartment, distance moved in each compartment).

Analysis of Learning and Memory

Y-Maze: Spontaneous alternation rates were assessed using a triangular Y-shaped maze constructed from black plastic material with arm sizes of 30 cm×8 cm. During 20 min test sessions, each mouse was randomly placed in one arm and allowed to move freely through the maze (Frenois, F., Cador, M., Caille, S., Stinus, L. & Le Moine, C. (2002) Neural correlates of the motivational and somatic components of naloxone-precipitated morphine withdrawal. Eur J Neurosci., 16, 1377-1389). Alternation was defined as successive entries into the three arms in overlapping triplet sets. An entry was defined to be successive as soon as a mouse enters an arm with all four paws. The percent alternation was calculated as the ratio of actual to possible alternations. In order to diminish odor cues, the maze was cleaned with a solution containing 30% ethanol, 60% water and 10% odorless soap.

Cross-Maze: The Cross-Maze consists of black plastic material (arm sizes: 30.0 cm length, 8.0 cm breadth, wall height 15.0 cm). Adjacent arms are in a 90° position. The four arms extend from a central space measuring 8.0 cm in square. Thus, the animals visit the arms via a central space. During 20.0 min test sessions, each mouse is initially randomly placed in one arm and allowed to traverse freely through the maze. Individual arms are signed 1-4. An alternation is defined as entry into four different arms on consecutive entries on overlapping quadruple sets (for example 2, 3, 4, 1 or 4, 2, 3, 1 but not 1, 2, 3, 2). An entry was defined to be successive as soon as a mouse enters an arm with all four paws. The percent alternation is calculated as the ratio of actual to overall performed alternations during the period of observation. In order to diminish odor cues, the maze was cleaned with a solution containing 30% ethanol, 60% water and 10% odorless soap after each trial. The test is being performed under modest white light conditions. Shorter timeframes for the test, i.e. 10 min, are possible.

T-maze continuous alternation task (T-CAT): A T-maze was used according to the measures provided by Gerlai (Gerlai, R. (1998) A new continuous alternation task in T-maze detects hippocampal dysfunction in mice. A strain comparison and lesion study. Behav Brain Res., 95, 91-101). The apparatus was made of black plastic material with a black floor and guillotine doors. Testing of the mice consisted of one single session, which started with 1 forced-choice trial, followed by 14 free-choice trials. (i) Forced-choice trial: in the first trial, one of the two goal arms is blocked by lowering the guillotine door. After the mouse is released from the start arm, it will explore the maze, enter the open arm and return to the start position. As soon as the mouse returned to the start arm, the guillotine door was lowered and the animal was confined for 5 seconds. (ii) Free-choice trials: After opening the door of the start arm, the animal is free to choose between both goal arms, as all guillotine doors are open. Once the mouse entered a goal arm, the other goal arm is closed. When the mouse returned to the start arm, the next free-choice trial started after 5 s confinement in the start arm. A test session was terminated after 30 min or after 14 free-choice trials were carried out. The animals were never handled during the task and the experimenter was not aware of the genotype of the tested animals. An alternation ratio was calculated for each animal by dividing the number of alternating choices by the number of total choices. Animals performing less than 8 choices in the given time frame were excluded from the analysis.

Morris Water Maze: In the typical paradigm, a mouse is placed into a small pool of water back-end first to avoid stress, and facing the pool-side to avoid bias, which contains an escape platform hidden a few millimeters below the water surface. Visual cues, such as colored shapes, are placed around the pool in plain sight of the animal. The pool is usually 4 to 6 feet in diameter and 2 feet deep. A sidewall above the waterline prevents the mouse from being distracted by laboratory activity. When released, the mouse swims around the pool in search of an exit while various parameters are recorded, including the time spent in each quadrant of the pool, the time taken to reach the platform (latency), and total distance traveled. The mouse's escape from the water reinforces its desire to quickly find the platform, and on subsequent trials (with the platform in the same position) the mouse is able to locate the platform more rapidly. This improvement in performance occurs because the mouse has learned where the hidden platform is located relative to the conspicuous visual cues. After enough practice, a capable mouse can swim directly from any release point to the platform.

Analysis of Motor Performance

Clasping Test: To test clasping behavior, mice were suspended by the tail for 30 sec and the hindlimb-clasping time was scored. A duration of 0 sec clasping was given a score of 0, 1-10 sec a score of 1, 10-20 sec a score of 2 and a clasping of more than 20 sec a score of 3 (Nguyen, T., Hamby, A. & Massa, S. M. (2005) Clioquinol down-regulates mutant huntingtin expression in vitro and mitigates pathology in a Huntington's disease mouse model. Proc Natl Acad Sci USA., 102, 11840-11845).

Footprint analysis: To obtain footprints, the hindpaws were labeled with blue nontoxic ink. The animals were placed at one end of a dark tunnel (30 cm×7 cm diameter), which ends in an enclosed box. The floor of the tunnel was lined with white paper. Animals were allowed to walk to the other end of the tunnel, where they were retrieved and placed in their home cage. A minimum of two nonstop passes was required. Stride length was determined by measuring the distance between each step and average stride length was calculated (Barlow, C., Hirotsune, S., Paylor, R., Liyanage, M., Eckhaus, M., Collins, F., Shiloh, Y., Crawley, J. N., Ried, T., Tagle, D. & Wynshaw-Boris, A. (1996) Atm-deficient mice: a paradigm of ataxia telangiectasia. Cell., 86, 159-171).

Balance Beam: Balance and general motor function were assessed using the balance beam task. A 1 cm dowel beam is attached to two support columns 44 cm above a padded surface. At either end of the 50 cm long beam a 9×15 cm escape platform is attached. The animal is placed on the center of the beam and released. Each animal is given three trials during a single day of testing. The time the animal remained on the beam is recorded and the resulting latencies to fall of all three trials are averaged. If an animal remains on the beam for whole 60-sec trial or escapes to one of the platforms, the maximum time of 60 sec is recorded (Arendash, G. W., Gordon, M. N., Diamond, D. M., Austin, L. A., Hatcher, J. M., Jantzen, P., DiCarlo, G., Wilcock, D. & Morgan, D. (2001) Behavioral assessment of Alzheimer's transgenic mice following long-term Abeta vaccination: task specificity and correlations between Abeta deposition and spatial memory. DNA Cell Biol., 20, 737-744).

String Suspension Task: As a test of agility and grip strength, a 3 mm cotton string is suspended 35 cm above a padded surface in the beam apparatus. The animals are permitted to grasp the string by their forepaws and are released. A rating system from 0 to 5 is used during the single 60-sec trial to assess each animals' performance in this task: 0=unable to remain on the string; 1=hangs only by fore- or hindpaws; 2=as for 1, but attempts to climb onto string; 3=sits on string and is able to hold balance; 4=four paws and tail around string with lateral movement; 5=escape (Moran, P. M., Higgins, L. S., Cordell, B. & Moser, P. C. (1995) Age-related learning deficits in transgenic mice expressing the 751-amino acid isoform of human beta-amyloid precursor protein. Proc Natl Acad Sci USA, 92, 5341-5345).

Vertical Grip Hanging Task. Animals were tested for neuromuscular abnormalities (balance and muscle strength) by suspending them from wire bars (40×20 cm area with 1 mm wires 1 cm apart). Latency to fall within 60 sec was measured after a mouse was placed on the bars and turned upside down (height 30 cm) (Erbel-Sieler, C., Dudley, C., Zhou, Y., Wu, X., Estill, S. J., Han, T., Diaz-Arrastia, R., Brunskill, E. W., Potter, S. S. & McKnight, S. L. (2004) Behavioral and regulatory abnormalities in mice deficient in the NPAS1 and NPAS3 transcription factors. Proc Natl Acad Sci USA., 101, 13648-13653).

Rotarod: Motor learning and coordination were tested by the use of an accelerating rotarod (TSE-Systems, Germany). The rotating rod had an axis diameter of 3.5 cm and a black rubber surface. Each mouse was given six daily trials for two consecutive days. The mice were placed on top of the beam facing away from the experimenters view. They had to move forward on the drum (which rotates with increasing speed around the vertical axis), being forced to continuously adjust their timing of movements. At the beginning of each trial, mice were placed on the inactive drum, which was accelerated to a speed of 48 rpm over a trial period of 360 sec. The time until the animal fell off the rod was recorded with a cut-off after 360 sec (Dere, E., De Souza-Silva, M. A., Frisch, C., Teubner, B., Sohl, G., Willecke, K. & Huston, J. P. (2003) Connexin30-deficient mice show increased emotionality and decreased rearing activity in the open-field along with neurochemical changes. Eur J Neurosci., 18, 629-638). Analysis was carried out using a two-way ANOVA (genotype x training day), followed by Bonferroni post hoc tests.

Forced Swimming Test: The forced swimming test is performed identical to a probe test in the Morris Water Maze (Spittaels, K., Van den Haute, C., Van Dorpe, J., Bruynseels, K., Vandezande, K., Laenen, I., Geerts, H., Mercken, M., Sciot, R., Van Lommel, A., Loos, R. & Van Leuven, F. (1999) Prominent axonopathy in the brain and spinal cord of transgenic mice overexpressing four-repeat human tau protein. Am J Pathol, 155, 2153-2165). In brief, a pool with a diameter of 110 cm is filled with opaque water to a height of 20 cm and is kept at 22° C. The mice were placed in the middle of the pool for one 60-sec single trial and total swimming distance and swimming speed were measured using a computer automated tracking system (VideoMot2, TSE-Systems).

Open Field: The open field test was used to assess both exploratory behavior and locomotor activity. The mice were tested using an open field box made of gray plastic with 50×50 cm surface area and 38 cm-high walls. Monitoring was done by an automated tracking system equipped with a rearing indicator consisting of 32 infrared sensors to detect vertical activity (VideoMot2, TSE-Systems, Germany). The behavioral parameters registered during 5-min sessions were (i) running speed and total traveled distance (ii) the ratio of time spent in the central part (20×20 cm) versus total time (iii) rearing episodes: the number of times an animal stood upon its hind legs with forelegs in the air or against the wall (measure of vertical activity) (Dere, E., De Souza-Silva, M. A., Frisch, C., Teubner, B., Sohl, G., Willecke, K. & Huston, J. P. (2003) Connexin30-deficient mice show increased emotionality and decreased rearing activity in the open-field along with neurochemical changes. Eur J Neurosci., 18, 629-638).

Elevated Plus-Maze. Apparatus: The Elevated Plus-Maze was built according to the description of Lister (1987). It had a black Plexiglas floor with a 5×5 cm central square platform, from which radiated two 45×5 cm open arms with 0.25 cm high edges and two 45×5 cm closed arms with 40 cm high walls made of clear Plexiglas. A white line was drawn half way along each of the four arms so as to measure locomotion. The apparatus was raised to 45 cm above the floor on a plus-shaped plywood base. The apparatus was located in a 2×5 m laboratory room that was illuminated with a 60-watt red light bulb.

Procedure: Mice were carried into the test room in their home cages. Mice were handled by the base of their tails at all times. Mice were placed, one at a time, in the central square of the Plus-Maze facing an open arm. The mice were then allowed to explore the apparatus for 5 minutes. An observer sitting quietly about 1 m from the apparatus recorded the behaviour of the animals on the maze. A video camcorder located 150 cm above the center of the maze also recorded behaviour. Behaviours were scored using Limelight. After 5 minutes, mice were removed from the maze by the base of their tails and returned to their home cage. The maze was then cleaned with a solution of 70% ethyl alcohol and permitted to dry between tests.

Behaviours Scored Included:
1. Open arms entries: Frequency with which the animal entered the open arms. All four of the mouse's paws were required to be in the arm to be counted as an entry.
2. Closed arm entries: Frequency with which the animal entered the closed arms. All four of the mouse's paws were required to be in the arm to be counted as an entry.
3. Open arm duration: Length of time the animal spent in the open arms.
4. Closed arm duration: Length of time the animal spent in the closed arms.
5. Center square entries: Frequency with which the animal entered the central square with all four paws.
6. Central square duration: Length of time the animal spent in the central square.
7. Head dipping: Frequency with which the animal lowered the head over the sides of the open arm toward the floor.
8. Stretch attend postures: Frequency with which the animal demonstrates forward elongation of head and shoulders followed by retraction to original position.
9. Rearing: Frequency with which the animal stands on hind legs or leans against walls of the maze with front paws.
10. Nonexploratory behaviour: Grooming or any time the mouse is not moving.
11. Urination: Number of puddles or streaks of urine.
12. Defecation: Number of fecal boli produced.
13. Locomotion: Number of times the animal crossed a line drawn on the open and closed arms.

From these results the percentage of entries into the open arms and closed arms based on the total arms entries were calculated for each animal. The percentage of time spent in the open arms and the closed arms was calculated over the 5 minute test. The index of open arm avoidance (Trullas, R., & Skolnick, P. 1993. Differences in fear motivated behaviors among inbred mouse strains. *Psychopharmacology,* 111, 323-331) was calculated as [100−(% time on open arms+% entries into the open arms)\2].

---

What is claimed is:

1. A transgenic non-human animal whose genome comprises: a DNA transgene encoding at least one Aβ peptide consisting of AβN3E-42 (SEQ ID NO: 1), AβN3Q-42 (SEQ ID NO: 2), AβN3E-40 (SEQ ID NO: 3) or AβN3Q-40 (SEQ ID NO: 4).

2. The transgenic non-human animal of claim 1, wherein the animal is heterozygous for the transgene.

3. The transgenic non-human animal of claim 1, wherein the animal is homozygous for the transgene.

4. The transgenic non-human animal of claim 1, wherein the animal is a mouse.

5. The transgenic non-human animal of claim 1, wherein the transgene is of murine origin.

6. The transgenic non-human animal of claim 1, wherein the transgene is of human origin.

7. The transgenic non-human animal of claim 1, wherein the DNA transgene encodes a chimeric or humanized polypeptide.

8. The transgenic non-human animal of claim 1, wherein the transgene encodes at least one Aβ peptide consisting of AβN3E-42 (SEQ ID NO: 1) or AβN3Q-42 (SEQ ID NO: 2).

9. The transgenic non-human animal according to claim 1, wherein the transgene is operably linked to a tissue-specific promoter.

10. A method for screening for biologically active agents that inhibit or promote Aβ peptide effects in vivo, comprising:
    a) administering a test agent to the transgenic non-human animal of claim 1; and
    b) determining the effect of the agent on the effect of Aβ peptide produced.

11. The method of claim 10, wherein the transgenic non-human animal is heterozygous for the transgene.

12. The method of claim 10, wherein the transgenic non-human animal is homozygous for the transgene.

13. The method of claim 10, wherein the animal is a mouse.

14. The method of claim 10, wherein the transgene is of murine origin.

15. The method of claim 10, wherein the transgene is of human origin.

16. The method of claim 10, wherein the transgene encodes a chimeric or humanized polypeptide.

17. The method of claim 10, wherein the transgene encodes AβN3E-42 (SEQ ID No: 1), AβN3Q-42 (SEQ ID No: 2), AβN3E-40 (SEQ ID No: 3) and/or AβN3Q-40 (SEQ ID No: 4).

18. The method of claim 10, wherein the transgene encodes AβN3E-42 (SEQ ID No: 1) and/or AβN3Q-42 (SEQ ID No: 2).

19. A method for screening for a target compound that is influenced by Aβ peptide production, wherein said method comprises the evaluation of the effects of Aβ peptide in vivo with the use of the transgenic non-human animal of claim 1 on a possible target compound.

20. A cell or cell line derived from the transgenic non-human animal of claim 1.

21. A transgenic mouse comprising:
    a transgenic nucleotide sequence encoding Aβ peptide operably linked to a promoter integrated into the genome of the mouse,
    wherein,
    the transgene encodes a peptide consisting of AβN3E-42 (SEQ ID NO: 1), AβN3Q-42 (SEQ ID NO: 2), AβN3E-40 (SEQ ID NO: 3) or AβN3Q-40 (SEQ ID NO: 4); and
    the mouse demonstrates a phenotype that can be reversed or ameliorated with an Aβ peptide inhibitor of Aβ peptide effects.

22. The mouse of claim 21, wherein the mouse overexpresses Aβ peptide.

23. The mouse of claim 21, wherein the mouse is heterozygous for Aβ peptide.

24. The mouse of claim 21, wherein the mouse is homozygous for Aβ peptide.

25. The mouse of claim 21, wherein the transgenic sequence encodes murine Aβ peptide.

26. The mouse of claim 21, wherein the transgenic sequence encodes human Aβ peptide.

27. The mouse of claim 21, wherein the transgene encodes AβN3E-42 (SEQ ID No: 1) and/or AβN3Q-42 (SEQ ID No: 2).

28. A method for screening for therapeutic agents that inhibit or promote Aβ peptide effects comprising:
    a) administering test agents to the transgenic mouse of claim 21;
    b) evaluating the effects of the test agent on the neurological phenotype of the mouse; and
    c) selecting a test agent which inhibits or promotes Aβ peptide effects.

29. A method for screening for a target compound that is influenced by Aβ peptide production, wherein said method comprises the evaluation of the effects of Aβ peptide in vivo with the use of the transgenic mouse of claim 21 on a possible target compound.

* * * * *